(12) United States Patent
Fujiwara et al.

(10) Patent No.: US 10,393,765 B2
(45) Date of Patent: Aug. 27, 2019

(54) MEASUREMENT APPARATUS AND MEASUREMENT METHOD

(71) Applicant: Sysmex Corporation, Kobe-shi, Hyogo (JP)

(72) Inventors: Takao Fujiwara, Kobe (JP); Kazuyoshi Horii, Kobe (JP); Tatsuya Kosako, Kobe (JP); Tomoyuki Nose, Kobe (JP); Sayuri Tomoda, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 15/637,992

(22) Filed: Jun. 29, 2017

(65) Prior Publication Data

US 2018/0003732 A1    Jan. 4, 2018

(30) Foreign Application Priority Data

Jun. 30, 2016  (JP) .................................. 2016-130099
Sep. 13, 2016  (JP) .................................. 2016-179030

(51) Int. Cl.
*G01N 21/00* (2006.01)
*G01N 35/10* (2006.01)
(Continued)

(52) U.S. Cl.
CPC ..... *G01N 35/1081* (2013.01); *G01N 21/0303* (2013.01); *G01N 21/07* (2013.01);
(Continued)

(58) Field of Classification Search
CPC .. G01N 21/253; G01N 21/0303; G01N 21/05; G01N 21/03; G01N 30/74
(Continued)

(56) References Cited

U.S. PATENT DOCUMENTS 6,632,399 B1   10/2003   Kellogg et al.
6,714,297 B1   3/2004   Ruckstuhl et al.
(Continued)

FOREIGN PATENT DOCUMENTS

JP   2005-300292   10/2005
JP   2012-255738   12/2012
(Continued)

*Primary Examiner* — Md M Rahman
(74) *Attorney, Agent, or Firm* — Brinks Gilson & Lione

(57) ABSTRACT

Disclosed is a measurement apparatus including: a support mechanism configured to support a cartridge in which a chamber is formed, the chamber being configured to store a measurement sample that generates light an intensity of which varies depending on an amount of a test substance; a photodetector configured to detect the light generated from the measurement sample stored in the chamber; and a reflection member provided between the photodetector and the cartridge supported by the support mechanism, the reflection member having an inner face, the reflection member being configured to reflect, at the inner face, the light generated from the measurement sample stored in the chamber, and guide the light to the photodetector, wherein the reflection member is configured to have an area surrounded by the inner face, the area decreasing from a side where the cartridge supported by the support mechanism is provided toward a side where the photodetector is provided.

20 Claims, 36 Drawing Sheets

(51) Int. Cl.
*G01N 21/03* (2006.01)
*G01N 21/53* (2006.01)
*G01N 21/64* (2006.01)
*G01N 35/00* (2006.01)
*G01N 21/07* (2006.01)
*B01L 3/00* (2006.01)

(52) U.S. Cl.
CPC ....... *G01N 21/532* (2013.01); *G01N 21/6456* (2013.01); *G01N 35/00069* (2013.01); *B01L 3/5027* (2013.01); *B01L 2300/0654* (2013.01)

(58) Field of Classification Search
USPC .......................................................... 356/440
See application file for complete search history.

(56) References Cited

U.S. PATENT DOCUMENTS

| | | |
|---|---|---|
| 7,989,163 B2 | 8/2011 | Takahashi |
| 9,897,596 B2 | 2/2018 | Kellogg et al. |
| 2004/0017761 A1* | 1/2004 | Aoyama .............. G02B 5/3083 369/112.17 |
| 2005/0136545 A1 | 6/2005 | Schmid et al. |
| 2013/0164175 A1* | 6/2013 | Kim ................... G01N 35/1081 422/64 |
| 2014/0154152 A1 | 6/2014 | Chumanov et al. |
| 2014/0242721 A1 | 8/2014 | Kellogg et al. |
| 2017/0138972 A1 | 5/2017 | Johno et al. |

FOREIGN PATENT DOCUMENTS

| | | |
|---|---|---|
| JP | 2014-518374 | 7/2014 |
| WO | WO 2016/002729 | 1/2016 |

\* cited by examiner

FIG. 10B  CROSS-SECTION C1-C2

FIG. 10C  CROSS-SECTION C1-C2

| WITHOUT ND | WITH ND OD1.0 | WITH ND OD2.0 |
|---|---|---|
|  1446980 |  123393 |  10225 |
|  1421126 |  128287 |  10597 |
|  1434384 |  125730 |  10467 |
|  1468876 |  125076 |  10822 |

<ROTATION POSITION A>   <ROTATION POSITION B>

SHIFT: -15 mm

SHIFT: -20 mm

SHIFT: -25 mm

PHOTODETECTOR 144a

PHOTODETECTOR 144a

MEASUREMENT APPARATUS AND MEASUREMENT METHOD

CROSS REFERENCE TO RELATED APPLICATIONS

This application claims priority from prior Japanese Patent Application No. 2016-130099, filed on Jun. 30, 2016, entitled "MEASUREMENT APPARATUS AND MEASUREMENT METHOD", and prior Japanese Patent Application No. 2016-179030, filed on Sep. 13, 2016, entitled "MEASUREMENT APPARATUS AND MEASUREMENT METHOD' the entire contents of which are incorporated herein by reference.

FIELD OF THE INVENTION

The present invention relates to a measurement apparatus and a measurement method for performing measurement of a test substance by using a cartridge.

BACKGROUND

US Patent Application Publication No. 2013/0164175 discloses a measurement apparatus configured to measure a specimen such as blood by using a disk-shaped cartridge 610, as shown in FIG. 36. In this measurement apparatus, the cartridge 610, in which a chamber 620 for storing a measurement sample therein is formed, is used. In addition, the measurement apparatus is provided with: a rotator 630 that supports and rotates the cartridge 610; a light emitter 640 that applies light to the measurement sample in the chamber 620; and a photodetector 650 that detects light having passed through the measurement sample. In this measurement apparatus, a camera is used as the photodetector 650. An image of the light having passed through the measurement sample in the chamber 620 is taken by the camera, and the measurement sample is analyzed on the basis of change and/or density of the color of the taken image.

In a measurement apparatus as described above, when a plurality of chambers are provided in a cartridge and a reaction between a specimen and a reagent is promoted while transferring a measurement sample between the chambers, the position of the measurement sample transferred to each chamber is not always the same. In this case, for example, the measurement sample may be positioned at the center of the chamber or may be positioned at the edge of the chamber. Such a displacement of the measurement sample in the chamber may cause variation in the position of the measurement sample with respect to the photodetector.

SUMMARY OF THE INVENTION

The present inventors have newly found that, when measurement of a test substance is performed with higher sensitivity by, for example, using a chemiluminescence method of detecting a test substance labeled with a chemiluminescent substance, the aforementioned variation in the position of a measurement sample with respect to a photodetector greatly affects the measurement results.

The present invention is directed to improvement of accuracy of measuring a test substance in a measurement apparatus that performs measurement of the test substance by using a cartridge.

The scope of the present invention is defined solely by the appended claims, and is not affected to any degree by the statements within this summary.

A first mode of the present invention relates to a measurement apparatus. The measurement apparatus according to this mode includes: a support mechanism configured to support a cartridge in which a chamber is formed, the chamber being configured to store a measurement sample that generates light an intensity of which varies depending on an amount of a test substance; a photodetector configured to detect the light generated from the measurement sample stored in the chamber; and a reflection member provided between the photodetector and the cartridge supported by the support mechanism, the reflection member having an inner face, the reflection member being configured to reflect, at the inner face, the light generated from the measurement sample stored in the chamber, and guide the light to the photodetector. The reflection member is configured to have an area surrounded by the inner face, the area decreasing from a side where the cartridge supported by the support mechanism is provided toward a side where the photodetector is provided.

In the measurement apparatus according to this mode, the cartridge is an exchangeable component in which functions required for detection of light generated from a measurement sample are combined. The chamber is a container provided in the cartridge to store a measurement sample prepared from a test substance and a predetermined reagent. The chamber does not necessarily have to store liquid all the time, and only has to have a spatial expanse for storing liquid.

A second mode of the present invention relates to a measurement method for measuring a test substance by using a cartridge in which a chamber is formed, the chamber being configured to store a measurement sample that generates light an intensity of which varies depending on an amount of a test substance. In the measurement method according to this mode, when light generated from the measurement sample stored in the chamber is caused to be reflected at an inner face of the reflection member and guided to the photodetector, a part of the light taken into the reflection member is reflected to a direction in which the light is not received by the photodetector, thereby to reduce the amount of light received by the photodetector. In the case where the measurement sample is positioned near a center of a region surrounded by the inner face of the reflection member, a larger amount of light, with respect to the light taken into the reflection member, is reflected to the direction in which the light is not received by the photodetector, than in the case where the measurement sample is positioned near an edge of the region surrounded by the inner face of the reflection member.

BRIEF DESCRIPTION OF THE DRAWINGS

FIGS. 10B and 10C are each a schematic diagram showing a cross-section of the structure of the pressing unit according to Embodiment 1 as viewed from the side thereof;

DETAILED DESCRIPTION OF THE PREFERRED EMBODIMENTS

Embodiment 1

Figure 1A:
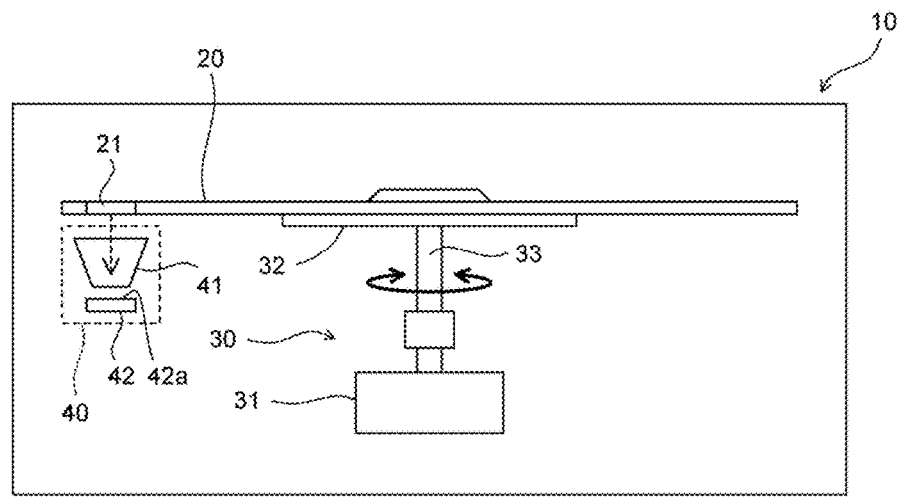
FIG. 1A is a schematic diagram showing a structure of a measurement apparatus according to an outline of Embodiment 1.
Figure 1B:
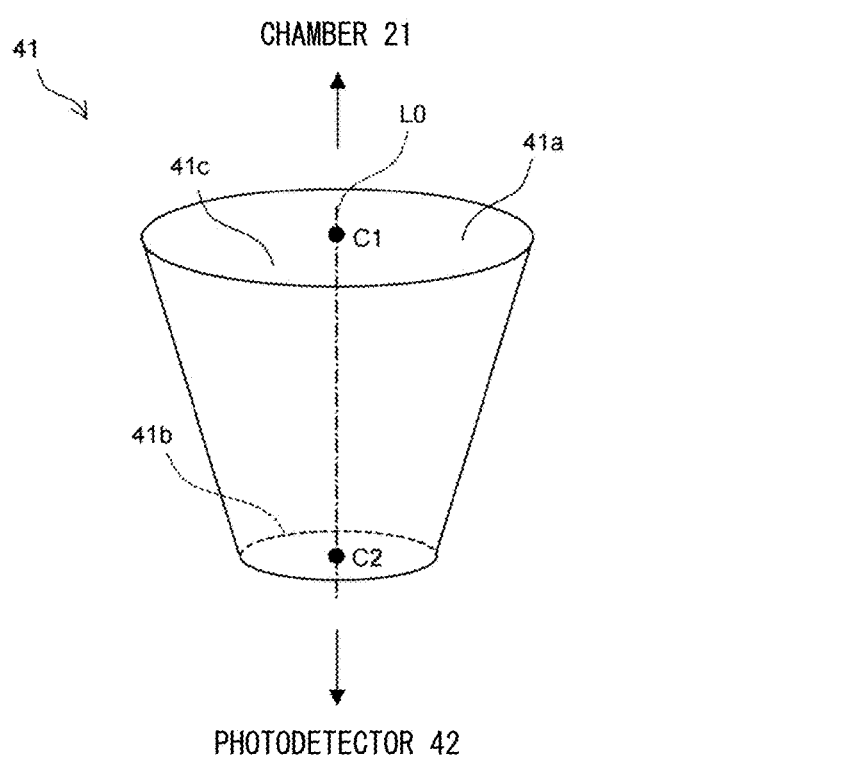
FIG. 1B is a schematic diagram showing a structure of a reflection member according to the outline of Embodiment 1.

With reference to FIGS. 1A and 1B, overviews of a measurement apparatus and a cartridge according to Embodiment 1 are described. In FIG. 1A, XYZ axes are orthogonal to one another. An X-axis positive direction is a rearward direction, a Y-axis positive direction is a leftward direction, and a Z-axis positive direction is a vertically downward direction.

As shown in FIG. 1A, a measurement apparatus 10 is a measurement apparatus that measures a test substance contained in a specimen by using a cartridge 20. The measurement apparatus 10 includes a support mechanism 30 and a detection unit 40.

The support mechanism 30 supports the cartridge 20, and locates a chamber 21 at a position opposed to the detection unit 40. The support mechanism 30 includes a motor 31 and a support member 32. The support mechanism 30 drives the motor 31 to rotate the cartridge 20 around a rotation shaft 33.

The support mechanism 30 may not necessarily include a structure to rotate the cartridge 20. For example, the support mechanism 30 may be configured to linearly move the cartridge 20. In this case, by linearly moving the cartridge 20 supported by the support mechanism 30, the chamber 21 is located at a detection position opposed to the detection unit 40. Alternatively, the support mechanism 30 may be configured to simply support the cartridge 20. In this case, when the cartridge 20 is placed on the support mechanism 30, the chamber 21 is positioned at the detection position.

The cartridge 20 is, for example, a plate-shaped disk. The cartridge 20 may have a shape other than the disk shape. The chamber 21 stores a complex in which a test substance contained in a specimen is bound to a substance that emits light. For example, a reagent that reacts with this substance to generate light is stored in the chamber 21. The detection unit 40 detects the light generated during the reaction process in the chamber 21.

The complex may be formed through binding of the test substance to a substance in which fluorescence is excited when light having a specific wavelength is applied to the substance. In this case, a light source for applying light to the chamber 21 is provided. The detection unit 40 detects the fluorescence that is excited, from the substance bound to the complex, by the light emitted from the light source.

The detection unit 40 includes a reflection member 41 and a photodetector 42. As shown in FIG. 1B, the reflection member 41 includes: a first opening 41a positioned on a side opposed to the chamber 21; a second opening 41b positioned on a side opposed to a detection face 42a of the photodetector 42, and having a smaller area than the first opening 41a; and a cylindrical inner face 41c connecting the first opening 41a and the second opening 41b. The first opening 41a is located at a position spaced apart, in the Z-axis positive direction, from a plane including a support face of the support mechanism 30 supporting the cartridge 20, that is, a plane including an upper face of the support member 32.

The first opening 41a and the second opening 41b each have a round shape, and the inner face 41c has a conical shape. The first opening 41a and the second opening 41b are coaxially arranged. When viewed from the photodetector 42 side, the first opening 41a has a size including the chamber 21 located at the detection position. The first opening 41a is located at a position spaced apart from a plane including the support face of the support mechanism 30 supporting the cartridge 20, that is, the upper face of the support member 32. The inner face 41c has an axially symmetrical shape. The inner face 41c is formed of, for example, a mirror-finished face that reflects light by substantially 100%. The inner face 41c is linear at a cross-section taken along an axis L0 connecting a center C1 of the first opening 41a and a center C2 of the second opening 41b.

The first opening 41a and the second opening 41b each may have a shape other than a round shape. For example, when the chamber 21 has an elliptic shape, the first opening 41a may have an elliptic shape. The first opening 41a and the second opening 41b may be arranged so that the centers thereof are displaced from each other in a plan view. The inner face 41c may not have an axially symmetrical shape. The inner face 41c may have a curved portion that protrudes toward the opposite side from the axis L0 or may have a curved portion that protrudes toward the axis L0, at the cross-section taken along the axis L0 connecting the center C1 of the first opening 41a and the center C2 of the second opening 41b.

The reflection member 41 takes in light generated in the chamber 21, causes the light having been taken in to be reflected at the inner face 41c, and guides the reflected light to the detection face 42a of the photodetector 42. At this time, in the measurement apparatus 10 configured as described above, the chamber 21 could be displaced from the detection position opposed to the first opening 41a due to, for example, braking error of the motor 31. The displaced chamber 21 could cause a region of the reagent stored in the chamber 21, that is, a light emitting region, to be displaced from the center C1 of the first opening 41a. Further, in the case where the amount of the reagent stored in the chamber 21 is less than the full capacity of the chamber 21 as described above, the reagent storage position in the chamber 21 may vary from detection to detection. Such a displacement of the reagent storage position also causes the light emitting region to be displaced from the center C1 of the first opening 41a.

As described above, when the light emitting region is displaced from the center C1 of the first opening 41a, the light taken into the reflection member 41 is reduced. However, on the other hand, a part of the light taken in from the chamber 21 into the reflection member 41 is reflected at the inner face 41c once or a plurality of times, and thereby, before reaching the photodetector 42, is directed to the first opening 41a and guided to the outside from the first opening 41a. By adjusting inclination of the inner face 41c, the amount of light to be guided to the outside when a sample, i.e., the light emitting region, is positioned near the edge of the first opening 41a can be reduced, compared with that when the sample is positioned near the center of the first opening 41a.

Therefore, by guiding the light generated in the chamber 21 to the detection face 42a of the photodetector 42 by using the reflection member 41, it is possible to reduce the difference between the amount of light that reaches the detection face 42a of the photodetector 42 in the case where the sample stored in the chamber 21 is displaced from the center C1 of the first opening 41a, and the amount of light that reaches the detection face 42a of the photodetector 42 in the case where the sample is positioned at the center of the first opening 41a. Thereby, variation in the amount of detected light, which is based on displacement of the sample, can be inhibited, whereby high analysis accuracy can be maintained. This effect is described later with reference to FIG. 18A to FIG. 28C.

<Examples of Specific Structures>

Hereinafter, specific structures of an analyzer and a cartridge according to Embodiment 1 are described.

An analyzer 100 corresponds to the measurement apparatus 10 shown in FIG. 1A. A mechanism including a motor 171, a support member 177, a rotation shaft 311, and a fixing member 312 corresponds to the support mechanism 30 shown in FIG. 1A. The motor 171, the support member 177, and the rotation shaft 311 correspond to the motor 31, the support member 32, and the rotation shaft 33 shown in FIG. 1A, respectively. A detection unit 140 corresponds to the detection unit 40 shown in FIG. 1A. A reflection member 142 and a photodetector 144a correspond to the reflection member 41 and the photodetector 42 shown in FIG. 1A, respectively. A first opening 142c, a second opening 142d, and an inner face 142f correspond to the first opening 41a, the second opening 41b, and the inner face 41c shown in FIG. 1B, respectively. A cartridge 200 corresponds to the cartridge 20 shown in FIG. 1B. A chamber 216 corresponds to the chamber 21 shown in FIG. 1A.

Figure 2A:
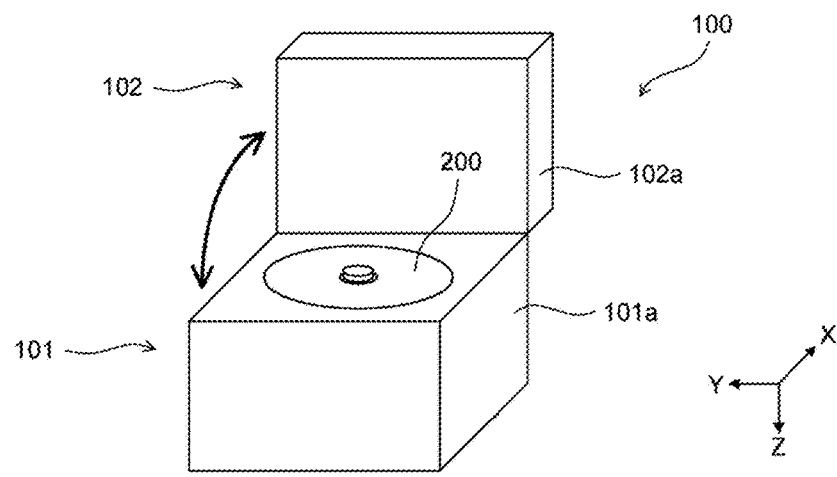
FIG. 2A is a schematic diagram showing an external structure of an analyzer according to Embodiment 1.

As shown in FIG. 2A, the analyzer 100 is an immune analyzer that measures a test substance in a specimen by utilizing antigen-antibody reaction, and analyzes the test substance on the basis of the measurement results. The analyzer 100 includes a body 101 and a lid 102. The body 101, except a portion thereof opposed to the lid 102, is covered with a casing 101a. The lid 102, except a portion thereof opposed to the body 101, is covered with a casing 102a. The body 101 supports the lid 102 so that the lid 102 is openable/closable with respect to the body 101. When the cartridge 200 is mounted or demounted, the lid 102 is opened as shown in FIG. 2A. The cartridge 200 is placed on an upper portion of the body 101.

Figure 2B:
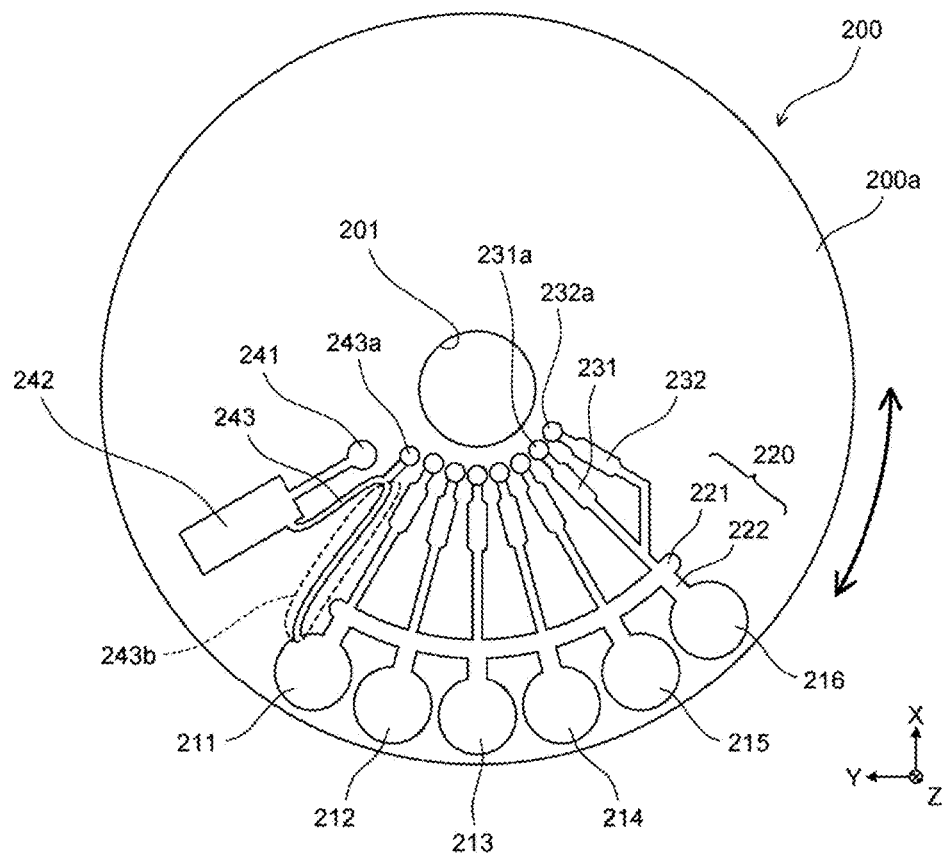
FIG. 2B is a schematic diagram showing a structure of a cartridge according to Embodiment 1 as viewed from above.

As shown in FIG. 2B, the cartridge 200 is an exchangeable component in which functions required for detection of a test substance are combined. The cartridge 200 is formed of a flat and disk-shaped substrate 200a. Portions in the cartridge 200 are formed by bonding a film (not shown) to the entire surface of the substrate 200a so as to cover recesses formed in the substrate 200a. The substrate 200a and the film bonded to the substrate 200a are made of a translucent material. The substrate 200a has a thickness that facilitates temperature control for the cartridge 200 by later-described heaters 321 and 322. For example, the thickness of the substrate 200a is a few millimeters, and specifically 1.2 mm.

The substrate 200a is provided with a hole 201, chambers 211 to 216, a channel 220, six liquid storage portions 231, a liquid storage portion 232, an opening 241, a separator 242, and a channel 243. The hole 201 penetrates the substrate 200a at the center of the substrate 200a. The cartridge 200 is placed on the analyzer 100 so that the center of the hole 201 is aligned with the rotation shaft 311 described later. Hereinafter, a radial direction and a circumferential direction, of a circle around the rotation shaft 311, are simply referred to as "radial direction" and "circumferential direction", respectively. The chambers 211 and 216 are arranged side by side in the circumferential direction, near the outer circumference of the substrate 200a.

The channel 220 includes an arc-shaped region 221 extending in the circumferential direction, and six regions 222 extending in the radial direction. The region 221 is connected to the six regions 222. The six regions 222 are connected to the chambers 211 to 216, respectively. The six liquid storage portions 231 are connected to the channel 220 via flow paths, and are present on extensions of the regions 222 connected to the chambers 211 to 216, respectively. The liquid storage portion 232 is connected, via a flow path, to a flow path that connects the region 222 connected to the chamber 216 with the liquid storage portion 231 on an extension of the region 222 connected to the chamber 216.

The chambers 211 to 216 are containers provided in the cartridge 200 to store a measurement sample prepared from a test substance and a predetermined reagent. Each of the chambers 211 to 216 does not necessarily have to store liquid all the time, and only has to have a spatial expanse for storing liquid. The channel 220 is a path provided in the cartridge 200 to transfer magnetic particles.

Each liquid storage portion 231 stores a reagent, and is provided with a seal 231a at an upper face thereof on the inner side in the radial direction. The seal 231a is configured to be opened when being pressed from above by a pressing unit 195 described later. Before the seal 231a is opened, the reagent in the liquid storage portion 231 does not flow into the channel 220. When the seal 231a is opened, the liquid storage portion 231 is communicated with the channel 220, whereby the reagent in the liquid storage portion 231 flows into the channel 220. Specifically, when the seal 231a is opened, the inside of the liquid storage portion 231 is communicated with the outside of the cartridge 200 at the position of the seal 231a.

Likewise, the liquid storage portion 232 stores a reagent, and is provided with a seal 232a at an upper face thereof on the inner side in the radial direction. The seal 232a is configured to be opened when being pressed from above by the pressing unit 195. Before the seal 232a is opened, the reagent in the liquid storage portion 232 does not flow into the channel 220. When the seal 232a is opened, the liquid storage portion 232 is communicated with the channel 220, whereby the reagent in the liquid storage portion 232 flows into the channel 220. Specifically, when the seal 232a is opened, the inside of the liquid storage portion 232 is communicated with the outside of the cartridge 200 at the position of the seal 232a.

The seals 231a and 232a each may be integrally formed in the substrate 200a, or may be formed of a film or the like bonded to an opening formed in the substrate 200a.

A whole blood specimen collected from a subject is injected to the separator 242 via the opening 241. The separator 242 separates the injected blood specimen into blood cells and plasma. The plasma separated through the separator 242 is moved to the channel 243. A hole 243a is provided at an upper face of the channel 243 on the inner side in the radial direction. The plasma, which is positioned in a region 243b in the channel 243, is moved to the chamber 211 due to a centrifugal force when the cartridge 200 is rotated. Thus, a predetermined amount of plasma is transferred to the chamber 211.

The components of the substrate 200a are formed only in one-third area of the substrate 200a as shown in FIG. 2B. However, these components may be formed in remaining two-third area of the substrate 200a. That is, three sets of the components may be formed in the substrate 200a.

Next, the internal structure of the analyzer 100 is described with reference to FIG. 3 to FIG. 12B.

A mounting member 110 has holes 111 to 114. The holes 111 to 114 penetrate the mounting member 110. In the hole 111, the rotation shaft 311 described later is positioned. The hole 112 has an elongated shape in the radial direction. A movement mechanism 130 is mounted on a lower face of the mounting member 110 via a member 131. In a horizontal plane, a hole 131a of the member 131 is located at the same position as the hole 112 of the mounting member 110. The detection unit 140 is mounted on the lower face of the mounting member 110 via a member 141. In a horizontal plane, the reflection member 142 of the detection unit 140 is located at the same position as the hole 113 of the mounting member 110. In the hole 114, a temperature sensor 178 described later is provided. At an upper face of the mounting member 110, closed-loop-shaped protruding portions 115 and 116 are formed. The protruding portions 115 and 116 protrude upward along the circumferential direction.

A housing 150 includes an upper face 151, housing portions 152 and 153, and an outer face 154. At the center of the upper face 151, a hole 155 is formed which penetrates the housing 150 in the vertical direction from the upper face 151 to the outer face 154. The hole 155 allows the rotation shaft 311 described later to pass therethrough. The housing portions 152 and 153 are configured as recesses protruding downward from the upper face 151. The mounting member 110 on which the movement mechanism 130 and the detection unit 140 are mounted is set in the housing 150. When the mounting member 110 is set in the housing 150, an outer periphery lower face of the mounting member 110 is joined to an outer periphery upper face of the housing 150. When the mounting member 110 is set in the housing 150, the movement mechanism 130 is housed in the housing portion 152 and the detection unit 140 is housed in the housing portion 153.

The mounting member 110 and the housing 150 are made of a light-shielding resin, and the color of the mounting member 110 and the housing 150 is set to black in order to enhance the light-shielding effect. Further, a predetermined elastic member (not shown) is provided between the outer periphery lower face of the mounting member 110 and the outer periphery upper face of the housing 150. The predetermined elastic member is made of, for example, light-shielding chloroprene rubber or a light-shielding polyurethane resin, and the color of the predetermined elastic member is set to black in order to enhance the light-shielding effect.

Figure 4A:
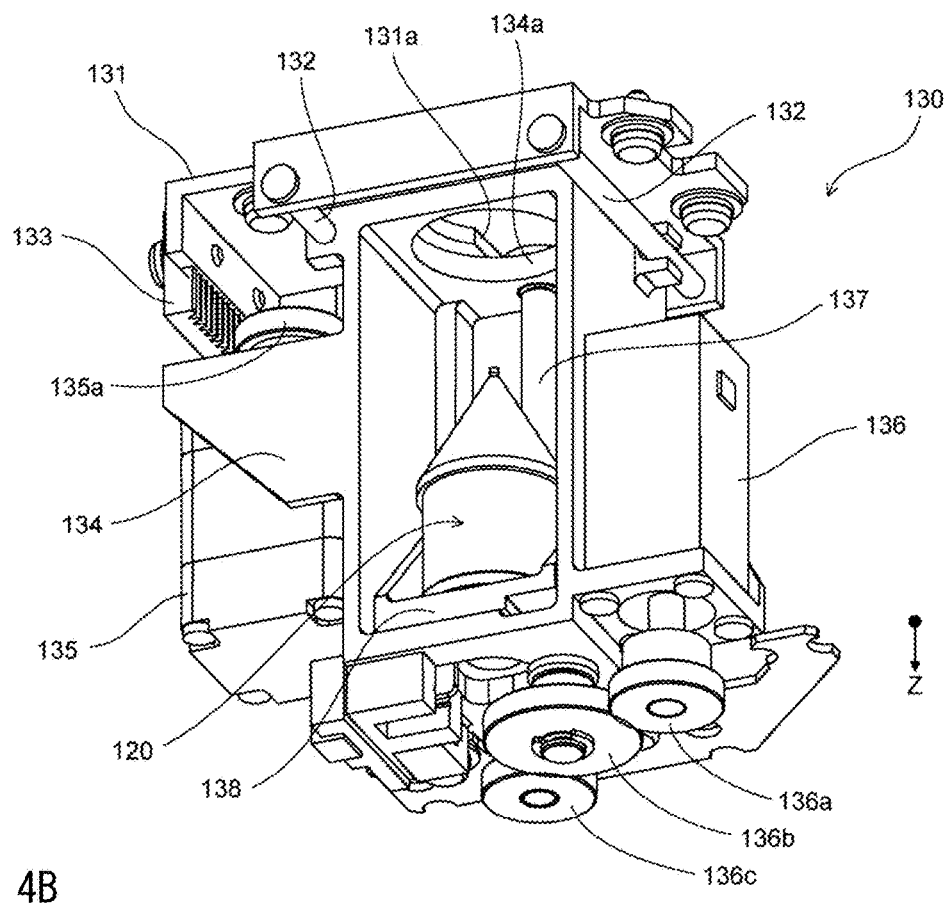
FIG. 4A shows the structures of the magnet and the movement mechanism according to Embodiment 1 as viewed from diagonally below.

As shown in FIG. 4A, the movement mechanism 130 includes the member 131, two supporting shafts 132, a gear portion 133, a support portion 134, a motor 135, a transmission gear 135a, a motor 136, transmission gears 136a to 136c, a screw 137, and a support portion 138. The two supporting shafts 132 are set at a lower face of the member 131. The gear portion 133 is mounted on a side face of the member 131, and has a flat plate shape. The support portion 134 is supported to be movable with respect to the two supporting shafts 132. The two supporting shafts 132 extend in the radial direction. In an upper face of the support portion 134, a hole 134a is formed. The hole 134a is located at the same position as the hole 131a of the member 131 in a horizontal plane.

The support portion 134 supports the motors 135 and 136, the transmission gear 136b, and the screw 137. The motors 135 and 136 each are implemented by a stepping motor. When a drive shaft of the motor 135 rotates, the transmission gear 135a mounted to the drive shaft rotates, and a driving force is transmitted to the gear portion 133. Thereby, the support portion 134 is moved in the radial direction while being supported by the two supporting shafts 132.

When a drive shaft of the motor 136 rotates, the transmission gear 136a mounted to the drive shaft rotates. The transmission gears 136a and 136b are engaged with each other, and the transmission gears 136b and 136c are engaged with each other. The transmission gear 136b is rotatably mounted to the support portion 134, and the transmission gear 136c is mounted to the screw 137. The screw 137 is rotatably supported by the support portion 134. The support portion 138 is supported by the screw 137 so as to vertically move in accordance with rotation of the screw 137. A magnet 120 is mounted on the support portion 138. Therefore, when the drive shaft of the motor 136 rotates, a driving force is transmitted to the transmission gears 136a, 136b, and 136c and to the screw 137. Thereby, the support portion 138 is moved in the vertical direction.

Since the movement mechanism 130 is configured as described above, the magnet 120 is movable in the radial direction in accordance with driving of the motor 135, and is movable in the vertical direction in accordance with driving of the motor 136. When the magnet 120 is moved inward in the radial direction, an upper end of the magnet 120 is moved to the radially inner side of the cartridge 200. When the magnet 120 is moved outward in the radial direction, the upper end of the magnet 120 is moved to the radially outer side of the cartridge 200. When the magnet 120 is moved upward, the upper end of the magnet 120 protrudes from the holes 131a and 134a and approaches the cartridge 200. When the magnet 120 is moved downward, the upper end of the magnet 120 is moved away from the cartridge 200.

A structure other than described above may be adopted to change the position of the magnet 120 with respect to the cartridge 200. For example, in order to move the magnet 120 in the vertical direction, the magnet 120 may be expanded and contracted, or the magnet 120 may be rotated around a direction parallel to the horizontal direction.

Figure 4B:
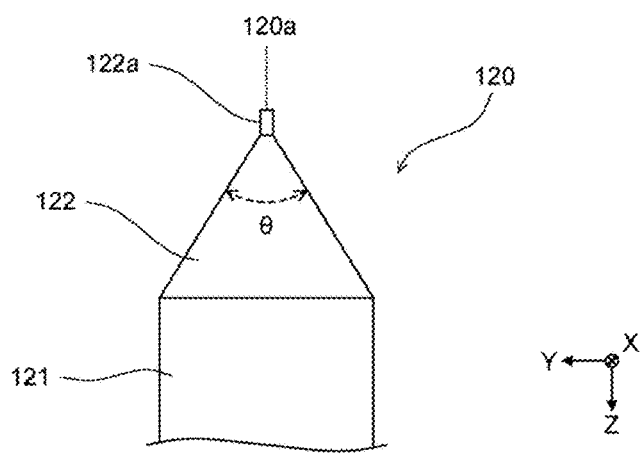
FIG. 4B is a schematic diagram showing the structure of the magnet according to Embodiment 1 as viewed from the side thereof.

As shown in FIG. 4B, the magnet 120 includes a permanent magnet 121 and a magnetic substance 122. The magnetic substance 122 may be either a paramagnetic substance or a ferromagnetic substance, or may be a combination thereof. The permanent magnet 121 has a cylindrical shape, and the magnetic substance 122 has a conical shape. The magnetic substance 122 is joined to an upper face of the permanent magnet 121. A tip portion 122a is formed at an upper end of the magnetic substance 122. The tip portion 122a has a columnar shape having a constant cross-sectional area when being cut in a horizontal plane. Specifically, the tip portion 122a has a cylindrical shape. The magnet 120 may have any shape as long as a portion thereof on the cartridge 200 side has a tapered shape, the cross-sectional area of which decreases toward the cartridge 200.

The larger the size of the permanent magnet 121 is, in other words, the larger the cross-sectional area of the permanent magnet 121 in a horizontal plane is, the greater the magnetic force applied to the magnetic particles in the cartridge 200 by the magnet 120 becomes. In addition, the smaller the angle θ of the tapered shape of the magnet 120 is, the greater the change in the magnetic force from a center axis 120a of the magnet 120 becomes. Then, the smaller the angle θ is, the greater the force for moving the magnetic particles in the cartridge 200 becomes. However, in the case where the cross-sectional area of the permanent magnet 121 in a horizontal plane is constant, the distance from the tip portion 122a to the upper face of the permanent magnet 121 is longer as the angle θ is smaller, and therefore, the magnetic force applied to the cartridge 200 by the magnet 120 becomes smaller. Accordingly, in order to increase both the magnetic force applied to the magnetic particles and the force for moving the magnetic particles in a well-balanced manner, the angle θ according to Embodiment 1 is set to, for example, 60°.

When both the magnetic force applied to the magnetic particles and the force for moving the magnetic particles are great, it is possible to prevent leftover of the magnetic particles when the magnetic particles are moved in the cartridge 200 by the magnet 120. Therefore, when the magnet 120 is configured as shown in FIG. 4B, both the magnetic force applied to the magnetic particles and the force for moving the magnetic particles can be increased in a well-balanced manner, whereby leftover of the magnetic particles can be prevented to inhibit unintended reduction in the amount of light detected by the detection unit 140. Thus, false negative due to unintended reduction in the amount of light can be inhibited, thereby realizing highly accurate detection.

The width of an edge of the magnet 120 on the cartridge 200 side, that is, the width of the tip portion 122a, is smaller than at least the minimum width of each region in the channel 220. Thereby, the complex collected by the magnet 120 can be smoothly moved in the channel 220 without being caught in the channel 220.

The magnet 120 may be composed of only a permanent magnet. That is, the magnet 120 may be composed of a permanent magnet having a shape obtained by combining the permanent magnet 121 and the magnetic substance 122 as described above. However, the magnet 120 composed of the permanent magnet 121 and the magnetic substance 122 can be formed more easily and accurately, compared with the magnet 120 composed of only a permanent magnet.

Figure 5A:
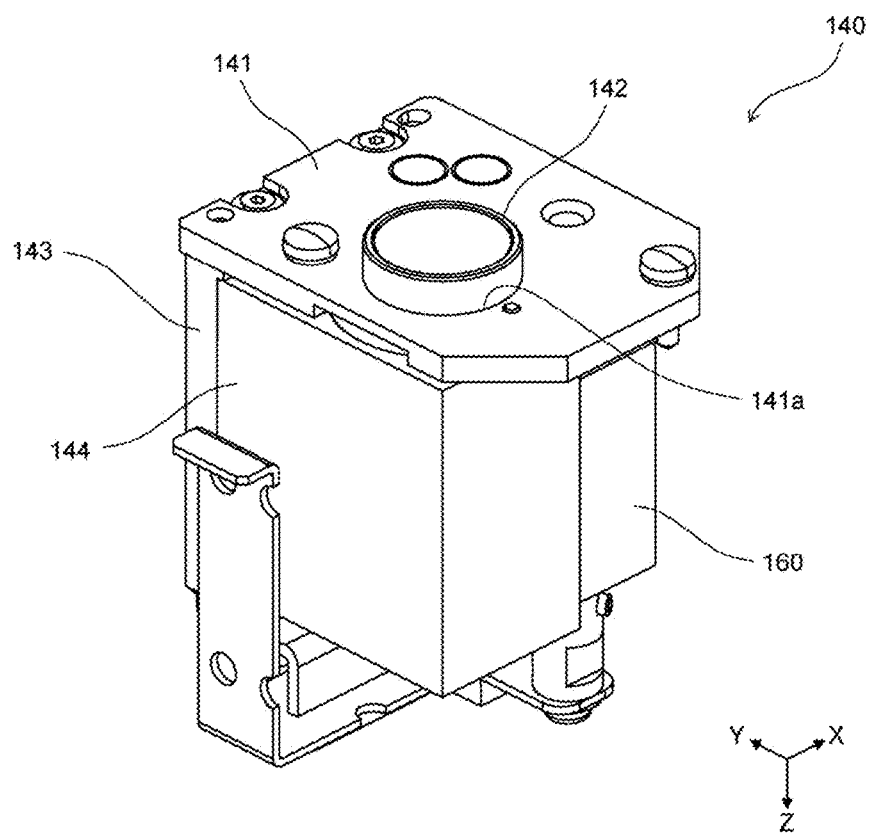
FIG. 5A shows the structure of the detection unit according to Embodiment 1 as viewed from diagonally above.

As shown in FIG. 5A, the detection unit 140 includes the member 141, the reflection member 142, a support portion 143, a light detection unit 144, and a light adjustment unit 160. The member 141 has a hole 141a penetrating the member 141 in the vertical direction. The reflection member 142 is fitted in the hole 141a formed in the member 141. The support portion 143 is mounted on a lower face of the member 141. The light detection unit 144 and the light adjustment unit 160 are mounted on the support portion 143.

Figure 5B:
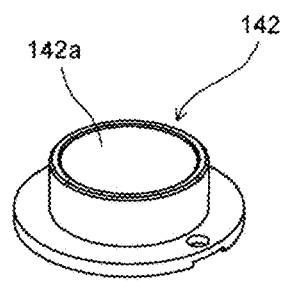
FIG. 5B shows the structure of the reflection member according to Embodiment 1 as viewed from diagonally above.
Figure 5C:
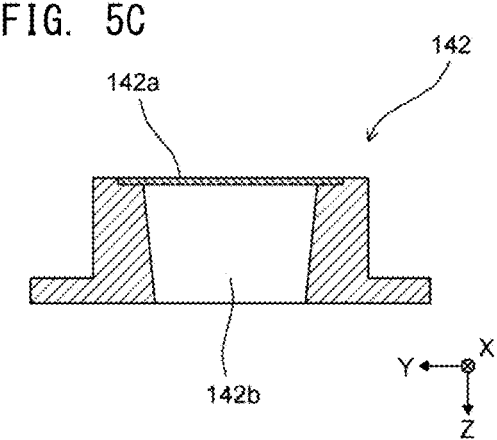
FIG. 5C is a schematic diagram showing a cross-section of the reflection member according to Embodiment 1 in a YZ plane as viewed from the side thereof.

As shown in FIGS. 5B and 5C, the reflection member 142 has a transparent plate 142a disposed at an upper portion thereof. The transparent plate 142a is a member for protecting the photodetector 144a described later. Since the optical effect of the transparent plate 142a is substantially ignorable, illustration of the transparent plate 142a is omitted for convenience in the figures described below. The reflection member 142 has, at the center thereof, a hole 142b penetrating the reflection member 142 in the vertical direction. The diameter of the hole 142b in a horizontal plane is decreased in the vertically downward direction. Regardless of whether the complex is positioned in the center or at the edge of the chamber 216, the reflection member 142 can guide the light generated in the chamber 216 by substantially the same amount to the photodetector 144a.

Figure 6A:
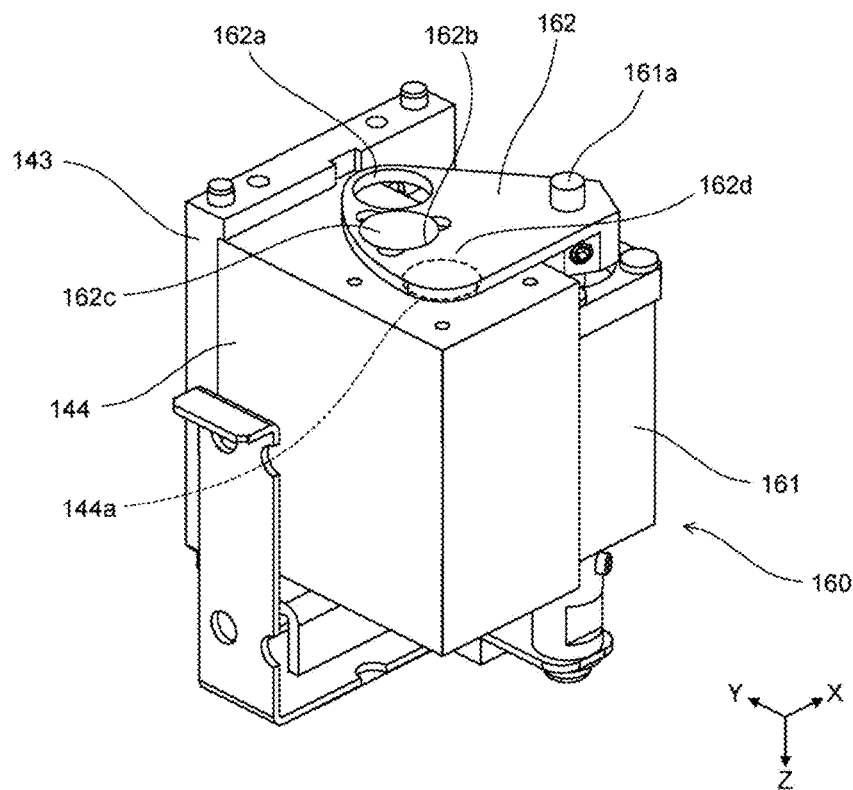
FIG. 6A shows the structure of the detection unit, according to Embodiment 1, which does not have a member and the reflection member, as viewed from diagonally above.

FIG. 6A shows a state where illustration of the member 141 and the reflection member 142 is omitted from the detection unit 140 shown in FIG. 5A.

As shown in FIG. 6A, the light adjustment unit 160 includes a motor 161 and a plate-shaped member 162. The motor 161 is implemented by a stepping motor. The plate-shaped member 162 is mounted to a drive shaft 161a of the motor 161, and has holes 162a and 162b. The holes 162a and 162b penetrate the plate-shaped member 162 in the vertical direction. A filter member 162c is inserted in the hole 162b. The filter member 162c is an ND filter.

When the motor 161 is driven, the plate-shaped member 162 rotates around the drive shaft 161a. Thereby, the hole 162a, the filter member 162c, and a region 162d of the plate-shaped member 162 other than the holes 162a and 162b, are each positioned directly above the photodetector 144a of the light detection unit 144. For a specific measurement item, high-intensity light is generated in the chamber 216. In this case, the filter member 162c is positioned directly above the photodetector 144a of the light detection unit 144, whereby the light incident on the photodetector 144a is reduced. Thus, an output signal from the photodetector 144a is inhibited from being saturated.

The light detection unit 144 is provided with the photodetector 144a at an upper face thereof. The photodetector 144a optically detects the test substance stored in the chamber 216. The photodetector 144a is implemented by, for example, a photo multiplier tube, a phototube, a photodiode, or the like. When the photodetector 144a is implemented by a photo multiplier tube, a pulse wave in response to reception of photons is outputted from the photodetector 144a. The light detection unit 144 has a circuit inside. The light detection unit 144 counts photons at regular intervals on the basis of the output signal from the photodetector 144a, and outputs the count value.

Figure 6B:
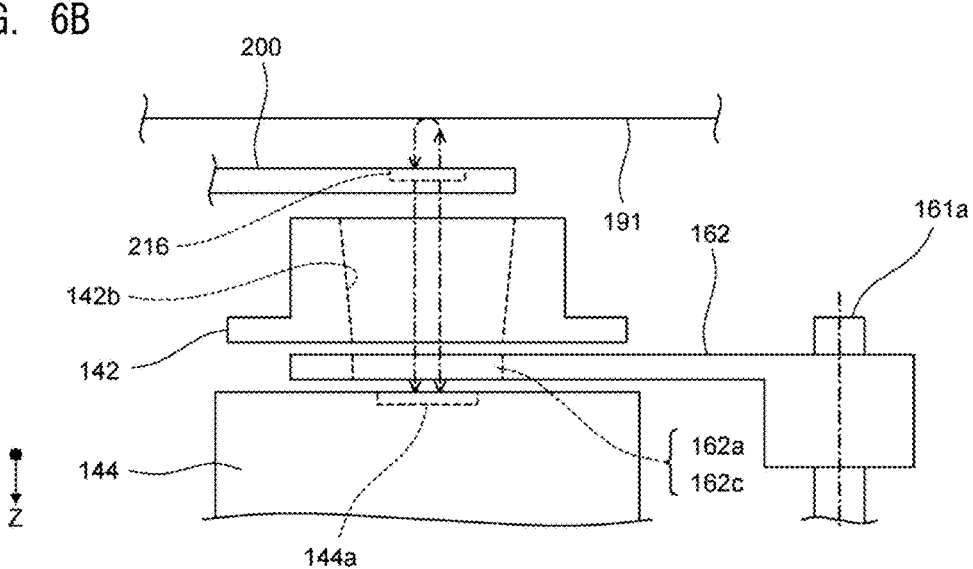
FIG. 6B is a schematic diagram showing a state where light generated from a chamber is received by a photodetector, according to Embodiment 1, as viewed from the side thereof.

As shown in FIG. 6B, the light generated in the chamber 216 of the cartridge 200 spreads upward and downward from the cartridge 200. The light spreading downward from the cartridge 200 passes through the hole 142b of the reflection member 142, and passes through the hole 162a or the filter member 162c of the light adjustment unit 160 to be received by the photodetector 144a. The light spreading upward from the cartridge 200 is reflected by a plate member 191 of the lid 102, which is described later, and returned to the chamber 216, and then is similarly received by the photodetector 144a. The light spreading upward from the cartridge 200 may be reflected by a mirror disposed on the plate member 191 of the lid 102.

Figure 7:
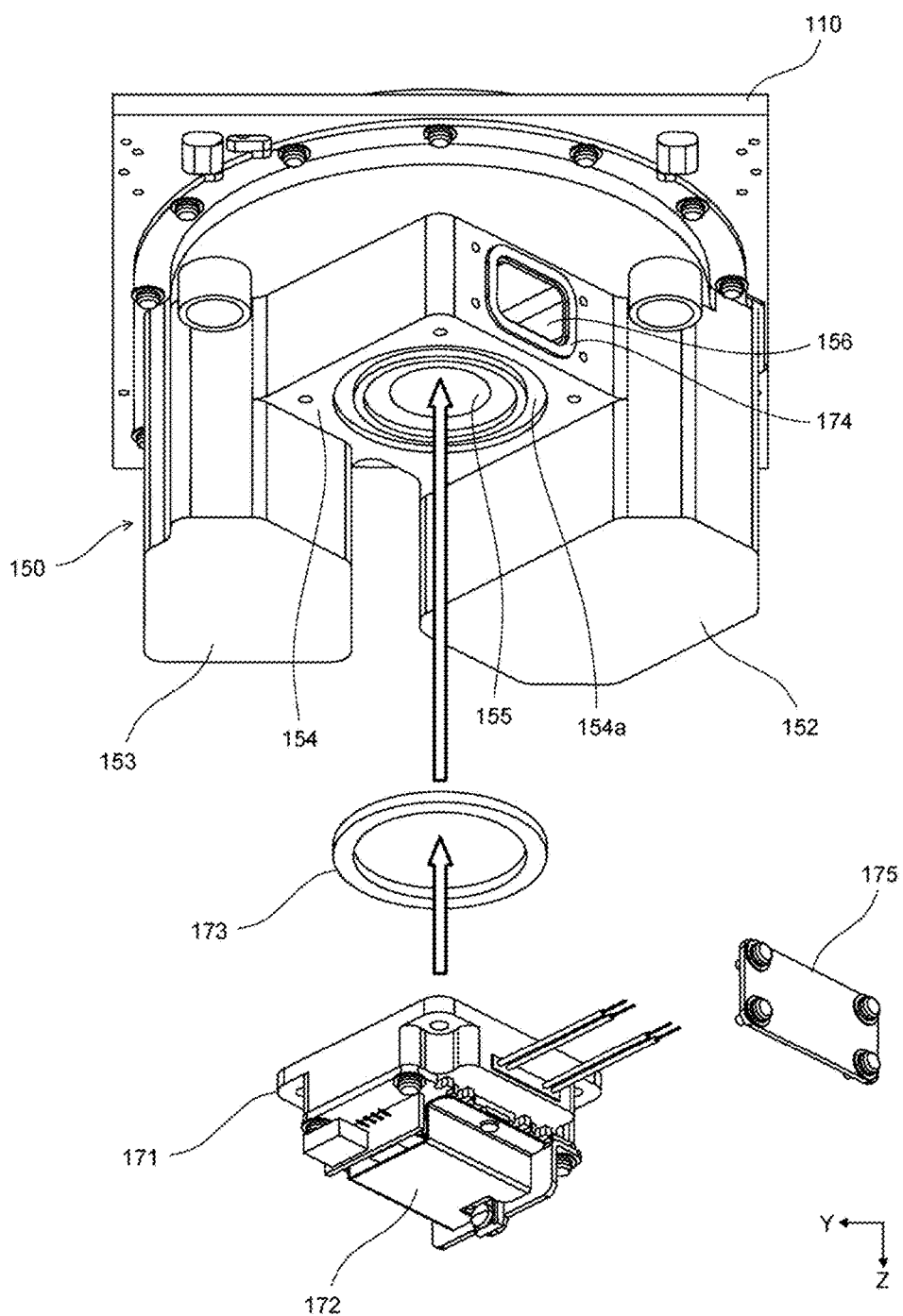
FIG. 7 shows a state where the housing has a motor, an elastic member, and a lid member mounted thereto, according to Embodiment 1, as viewed from diagonally below.

As shown in FIG. 7, the outer face 154 of the housing 150 is positioned on the lower side of the housing 150, and is positioned at the center of the housing 150 in a horizontal plane. The outer face 154 is a plane parallel to the horizontal plane. At the center of the outer face 154, an outlet of the hole 155 penetrating the housing 150 in the vertical direction from the upper face 151 to the outer face 154 is formed. On the outer face 154, a recess 154a is formed at the periphery of the outlet of the hole 155. The recess 154a has an annular external shape when viewed in the vertically upward direction. Further, the housing 150 is provided with a hole 156 which communicates with the outside of the housing 150 from the lateral side of the hole 155.

The motor 171 is implemented by a stepping motor. An encoder 172 is mounted on a lower face of the motor 171, and detects rotation of a rotation shaft of the motor 171. An elastic member 173 is made of, for example, a light-shielding polyurethane resin, and the color of the elastic member 173 is set to black in order to enhance the light-shielding effect. The elastic member 173 has an annular external shape that is fitted to the recess 154a of the outer face 154. The motor 171 is mounted to the outer face 154 so as to close the hole 155. Specifically, the elastic member 173 is fitted in the recess 154a so as to surround the hole 155, between the outer face 154 and the upper face of the motor 171 opposed to the outer face 154. Then, the motor 171 is mounted to the outer face 154, with the upper face thereof being pressed against the elastic member 173. Thus, the lower side of the hole 155 is closed by the elastic member 173 and the upper face of the motor 171.

When the motor 171 is mounted to the outer face 154, connection of the mechanisms inside the hole 155, and the like is performed through the hole 156. When connection of the mechanisms, and the like are completed, an elastic member 174 is mounted to the periphery of the outlet of the hole 156, and the hole 156 is closed by a lid member 175. The elastic member 174 and the lid member 175 are configured to have light-shielding properties.

Figure 8:
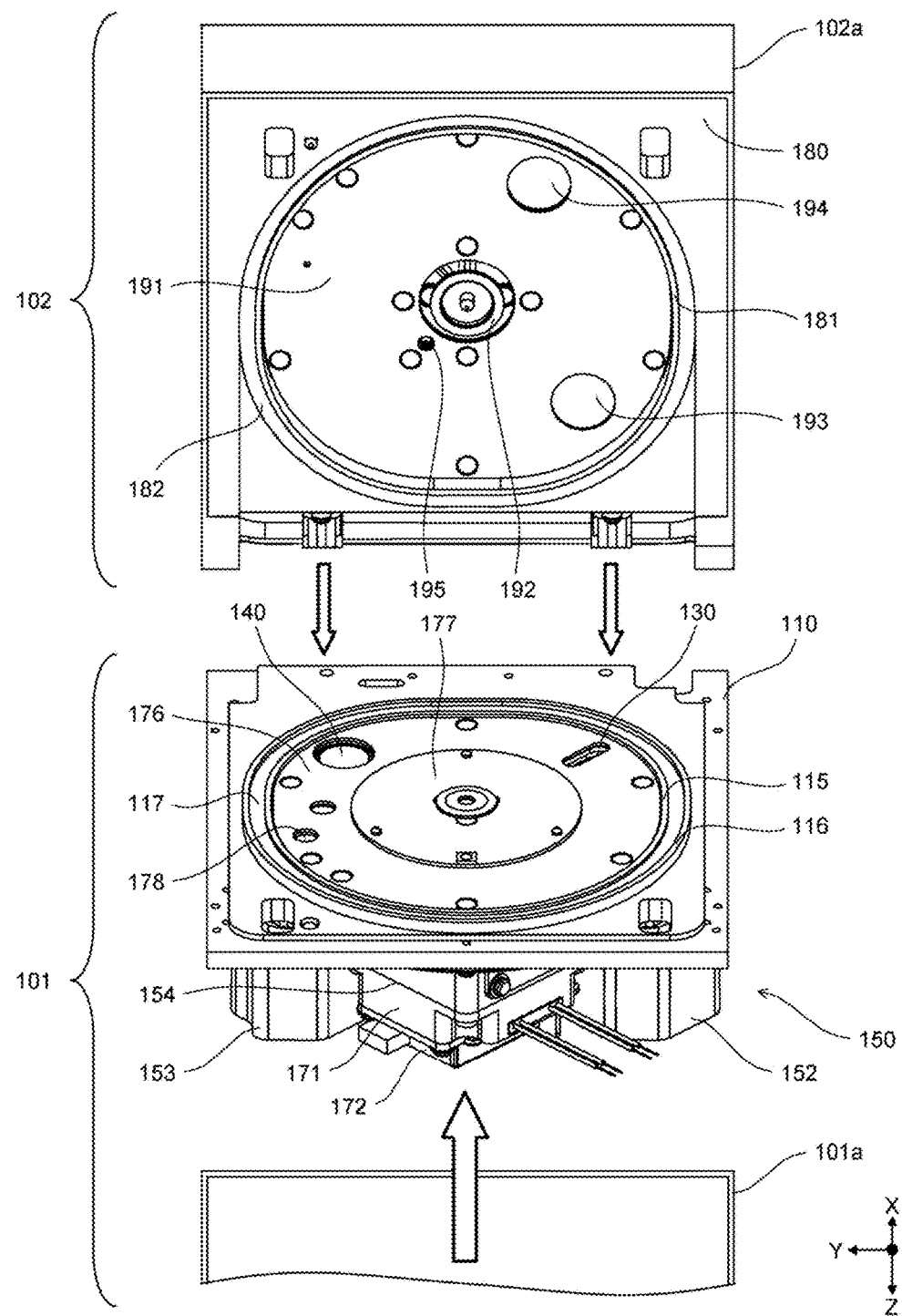
FIG. 8 shows a structure of a body according to Embodiment 1 as viewed from diagonally above and a structure of a lid as viewed from diagonally below.

As shown in FIG. 8, a plate member 176 and the support member 177 are disposed within the protruding portion 115 of the mounting member 110. The plate member 176 is made of a metal having high thermal conductivity. A heater 321 described later is mounted on a lower face of the plate member 176. The plate member 176 and the heater 321 each have holes at positions corresponding to the holes 111 to 114 of the mounting member 110 shown in FIG. 3. Through these holes, the movement mechanism 130, the detection unit 140, and the temperature sensor 178 are directly opposed to the lower face of the cartridge 200 as shown in FIG. 8. The temperature sensor 178 is disposed on the lower face side of the mounting member 110. The temperature sensor 178 detects the temperature of the cartridge 200 by means of infrared light.

The support member 177 is mounted at the center of the mounting member 110 via a mount member 310 described later. The support member 177 is implemented by, for example, a turntable. An elastic member 117 is provided between the protruding portion 115 and the protruding portion 116. The elastic member 117 is made of, for example, a light-shielding polyurethane resin, and the color of the elastic member 117 is set to black in order to enhance the light-shielding effect. The elastic member 117 is formed in a closed-loop shape. An upper face of the elastic member 117 is an elastically deformable junction face. The mounting member 110 and the housing 150 assembled as described above are set in the casing 101a, thereby completing the body 101.

FIG. 8 shows the lid 102 viewed from below. The lid 102 includes a mounting member 180, the plate member 191, a clamper 192, an image capturing unit 193, a lighting unit 194, and the pressing unit 195.

The mounting member 180 is made of a light-shielding resin, and the color of the mounting member 180 is set to black in order to enhance the light-shielding effect. The plate member 191 and the clamper 192 are disposed within a protruding portion 181 of the mounting member 180. The plate member 191, like the plate member 176, is made of a metal having high thermal conductivity. The heater 322 described later is mounted on an upper face of the plate member 191. A lower face of the mounting member 180, the plate member 191, and the heater 322 each have holes at positions corresponding to the image capturing unit 193, the lighting unit 194, and the pressing unit 195. Through these holes, the image capturing unit 193, the lighting unit 194, and the pressing unit 195 are directly opposed to the upper face of the cartridge 200. The image capturing unit 193, the lighting unit 194, and the pressing unit 195 are mounted on the upper face of the mounting member 180.

The image capturing unit 193 captures an image of the interior of the cartridge 200. The image capturing unit 193 is implemented by a miniature camera. The miniature camera includes a CCD image sensor, a CMOS image sensor, or the like. The lighting unit 194 irradiates the cartridge 200 with light when image capturing is performed by the image capturing unit 193. The lighting unit 194 is implemented by, for example, a light-emitting diode. The pressing unit 195 presses the seals 231a and 232a to open the seals 231a and 232a. The pressing unit 195 is described later with reference to FIGS. 10A to 10C.

The clamper 192 is mounted at the center of the mounting member 180. On the lower face of the mounting member 180, the closed-loop-shaped protruding portion 181 is formed. The protruding portion 181 protrudes downward along the circumferential direction. On the lower face of the mounting member 180, a recess is formed outside the protruding portion 181, and an elastic member 182 is fitted in this recess. The elastic member 182 is made of, for example, a light-shielding polyurethane resin, and the color of the elastic member 182 is set to black in order to enhance the light-shielding effect. The elastic member 182 is formed in a closed-loop shape. A lower face of the elastic member 182 is an elastically deformable junction face.

In assembling, the lid 102 is mounted to be openable/closable with respect to the mounting member 110 of the body 101, whereby the lid 102 is mounted on the body 101. The casing 101a of the body 101 is provided with a ventilation unit 350 described later. The ventilation unit 350 is described later with reference to FIGS. 12A and 12B.

Figure 9:
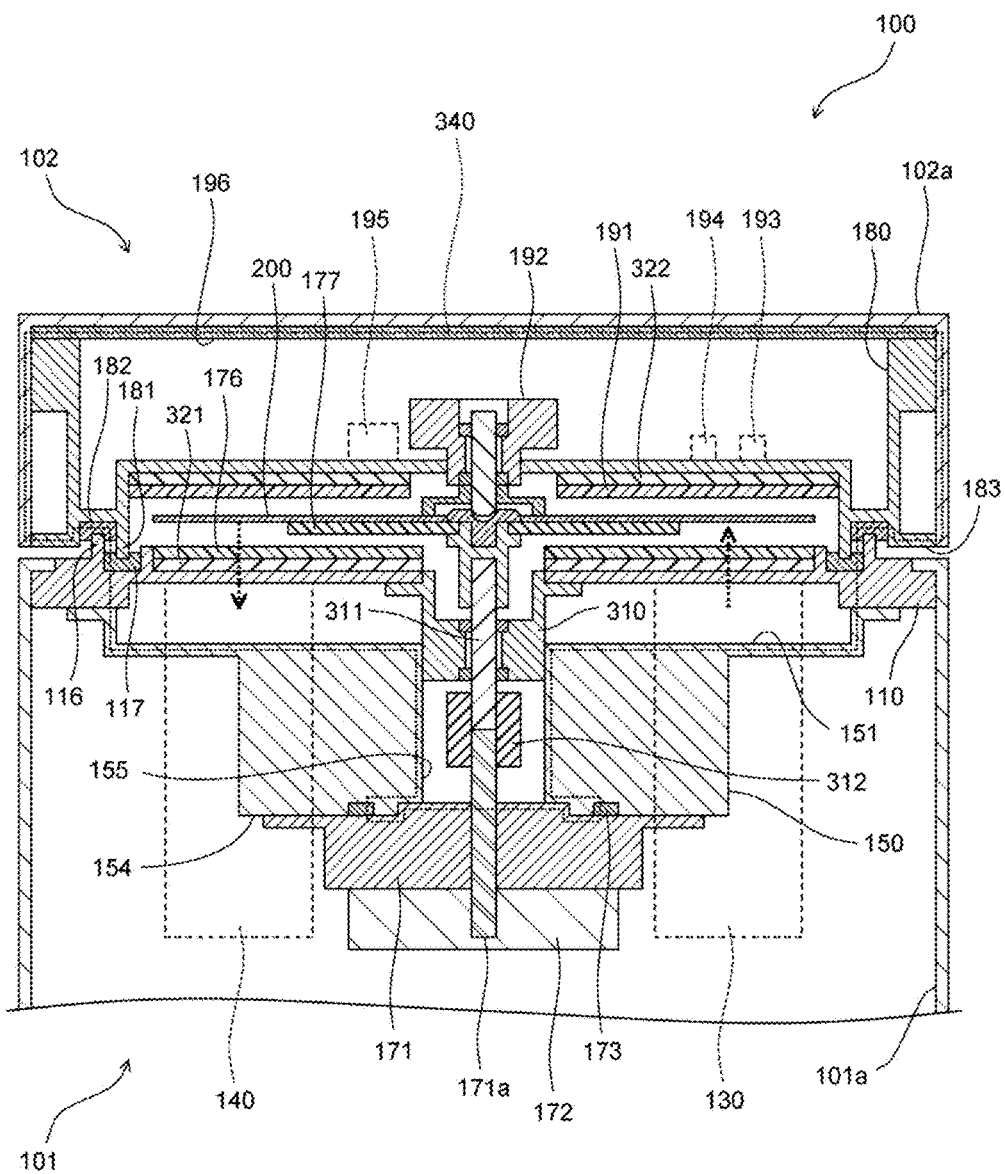
FIG. 9 is a schematic diagram showing a cross-section of the analyzer that is cut in a plane parallel to a YZ plane that passes a rotation shaft, according to Embodiment 1, as viewed from the side thereof.

FIG. 9 is a schematic diagram showing a cross-section of the analyzer 100 that is cut in a plane parallel to a YZ plane that passes the rotation shaft 311. FIG. 9 shows a state where the cartridge 200 is set in the analyzer 100, and the lid 102 is closed. As described above, the detection unit 140 and the movement mechanism 130 that holds the magnet 120 are mounted on the lower face of the mounting member 110, while the image capturing unit 193, the lighting unit 194, and the pressing unit 195 are mounted on the upper face of the mounting member 180. In FIG. 9, positions where these components are disposed are represented by broken lines.

As shown in FIG. 9, a drive shaft 171a of the motor 171 extends to the inside of the hole 155 as the motor 171 is mounted on the outer face 154. The mount member 310 is mounted in an upper portion of the hole 155. The mount member 310 rotatably supports the rotation shaft 311 extending in the vertical direction. The rotation shaft 311, inside the hole 155, is fixed to the drive shaft 171a of the motor 171 by the fixing member 312.

The support member 177 for supporting the lower face of the cartridge 200 is fixed to an upper portion of the rotation shaft 311 via a predetermined member. When the motor 171 is driven to rotate the drive shaft 171a, a rotation driving force is transmitted to the support member 177 via the rotation shaft 311. Thereby, the cartridge 200 mounted on the support member 177 rotates around the rotation shaft 311 and the drive shaft 171a. When the cartridge 200 is placed on the support member 177 and the lid 102 is closed, the clamper 192 presses an inner circumferential portion of the upper face of the cartridge 200 so that the cartridge 200 is rotatable.

Figure 13:
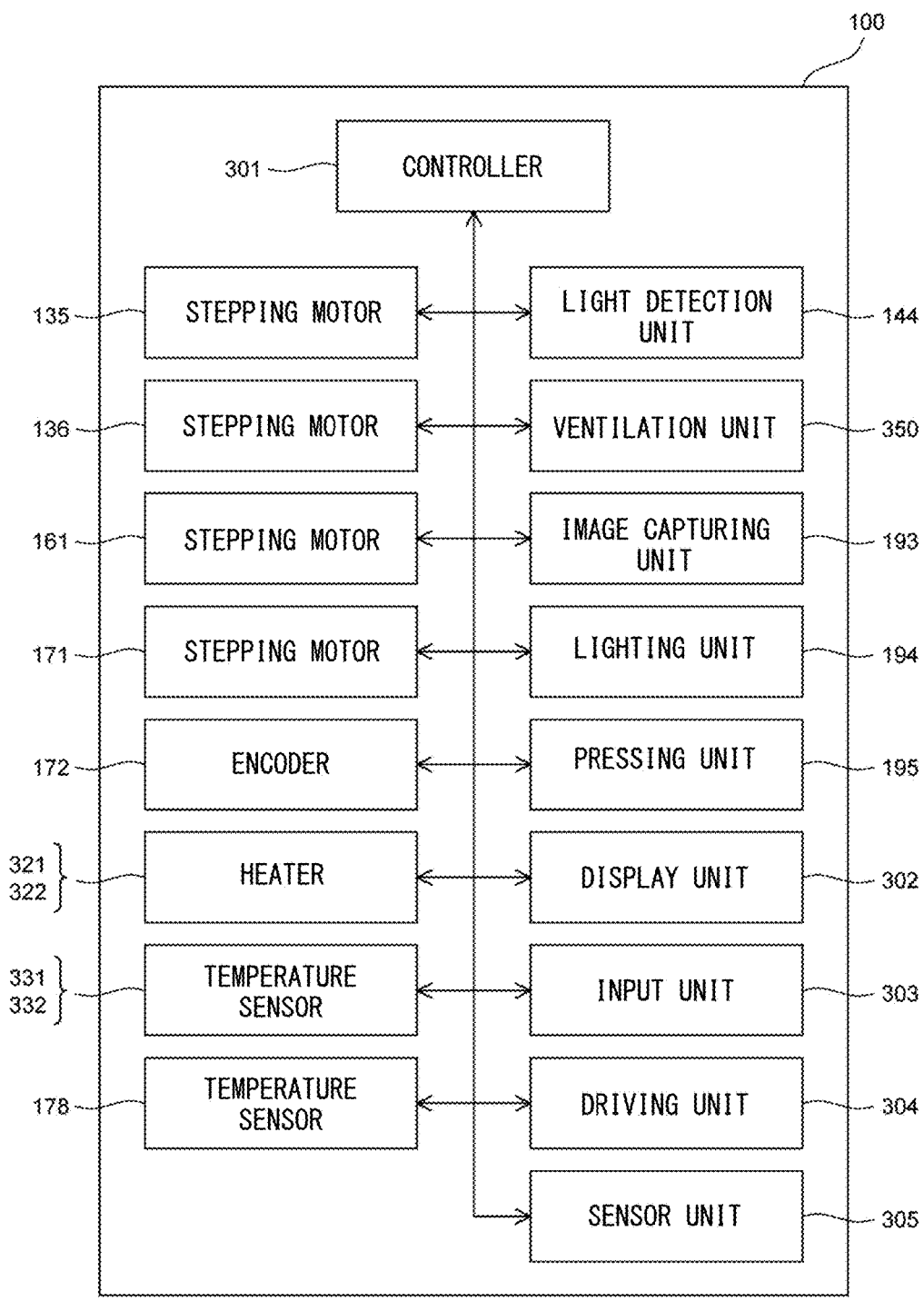
FIG. 13 is a block diagram showing the structure of the analyzer according to Embodiment 1.

The heater 321 is mounted on the lower face of the plate member 176 while the heater 322 is mounted on the upper face of the plate member 191. The heaters 321 and 322 each have a flat heat generating face, and are disposed so that the heat generating face is parallel to the cartridge 200. Thereby, the cartridge 200 can be efficiently heated. Temperature sensors 331 and 332 shown in FIG. 13 are mounted on the plate members 176 and 191, respectively. The temperature sensors 331 and 332 detect the temperatures of the plate members 176 and 191, respectively.

A controller 301 described later drives the heaters 321 and 322 so that the temperature of the plate member 176 detected by the temperature sensor 331 and the temperature of the plate member 191 detected by the temperature sensor 332 are predetermined temperatures when analysis is performed. The controller 301 drives the heaters 321 and 322 by a control method such as P control, PD control, or PID control, on the basis of the temperatures detected by the temperature sensors 331 and 332. Thereby, the temperature of the cartridge 200 is kept at a predetermined temperature. The predetermined temperature according to Embodiment 1 is 42° C. which allows reaction in the cartridge 200 to be appropriately proceeded. Keeping the temperature of the cartridge 200 constant as described above is particularly important for immunoassay. The controller 301 may drive the heaters 321 and 322 on the basis of the temperature detected by the temperature sensor 178.

The movement mechanism 130 applies a magnetic force to the cartridge 200 while the detection unit 140 receives light generated from the cartridge 200 side, as represented by dotted arrows in FIG. 9. Therefore, at the lower side of the cartridge 200, the mounting member 110 allows light to easily pass therethrough in the vertical direction. However, since the housing 150 is located beneath the mounting member 110, passage of light is prevented between a space beneath the cartridge 200 and the outside.

In an upper portion of the mounting member 180 of the lid 102, a light-shielding member 196 is mounted between the mounting member 180 and an inner face of the casing 102a. The light-shielding member 196 is made of a light-shielding resin, and the color of the light-shielding member 196 is set to black in order to enhance the light-shielding effect. A predetermined elastic member (not shown) is provided between an outer periphery lower face of the light-shielding member 196 and an outer periphery upper face of the mounting member 180. The predetermined elastic member is made of, for example, light-shielding chloroprene rubber or a light-shielding polyurethane resin, and the color thereof is set to black in order to enhance the light-shielding effect.

Since the holes are formed through the mounting member 180 at the positions where the image capturing unit 193, the lighting unit 194, and the pressing unit 195 are mounted, leakage of light occurs in the vertical direction at the positions where these components are disposed. Therefore, at the upper side of the cartridge 200, the mounting member 180 allows light to pass therethrough in the vertical direction. However, since the light-shielding member 196 is positioned above the mounting member 180, passage of light is prevented between the space above the cartridge 200 and the outside.

When the lid 102 is closed, the protruding portion 116 of the mounting member 110 is pressed and adhered onto the lower face of the elastic member 182 of the mounting member 180. The protruding portion 181 of the mounting member 180 is pressed and adhered onto the upper face of the elastic member 117 of the mounting member 110. In addition, a face 183 is formed at the lower face near the outer periphery of the mounting member 180, and the inner lateral sides of the lid 102 are covered with the casing 102a. Thereby, passage of light is prevented between the space lateral to the cartridge 200 and the outside.

Thus, a dark space 340 represented by a dotted line in FIG. 9 is formed by light-shielding portions. The light-shielding portion on the body 101 side is formed by: the protruding portion 116 and the elastic member 117 of the mounting member 110; the outer periphery of the mounting member 110; the housing 150; the upper face of the motor 171; the elastic member 173; the lid member 175; and the elastic member 174. The light-shielding portion on the lid 102 side is formed by: the casing 102a; the light-shielding member 196; the face 183 of the mounting member 180; the protruding portion 181 of the mounting member 180; and the elastic member 182. When the lid 102 is closed, the light-shielding portion on the body 101 side and the light-shielding portion on the lid 102 side are joined to each other at positions lateral to the cartridge 200, and the dark space 340 is surrounded by the light-shielding portions. Thus, leakage of light into the light-shielding portions is prevented. The structures of the light-shielding portions are merely an example, and the components and the like forming the light-shielding portions are not limited to those described above.

Figure 3:
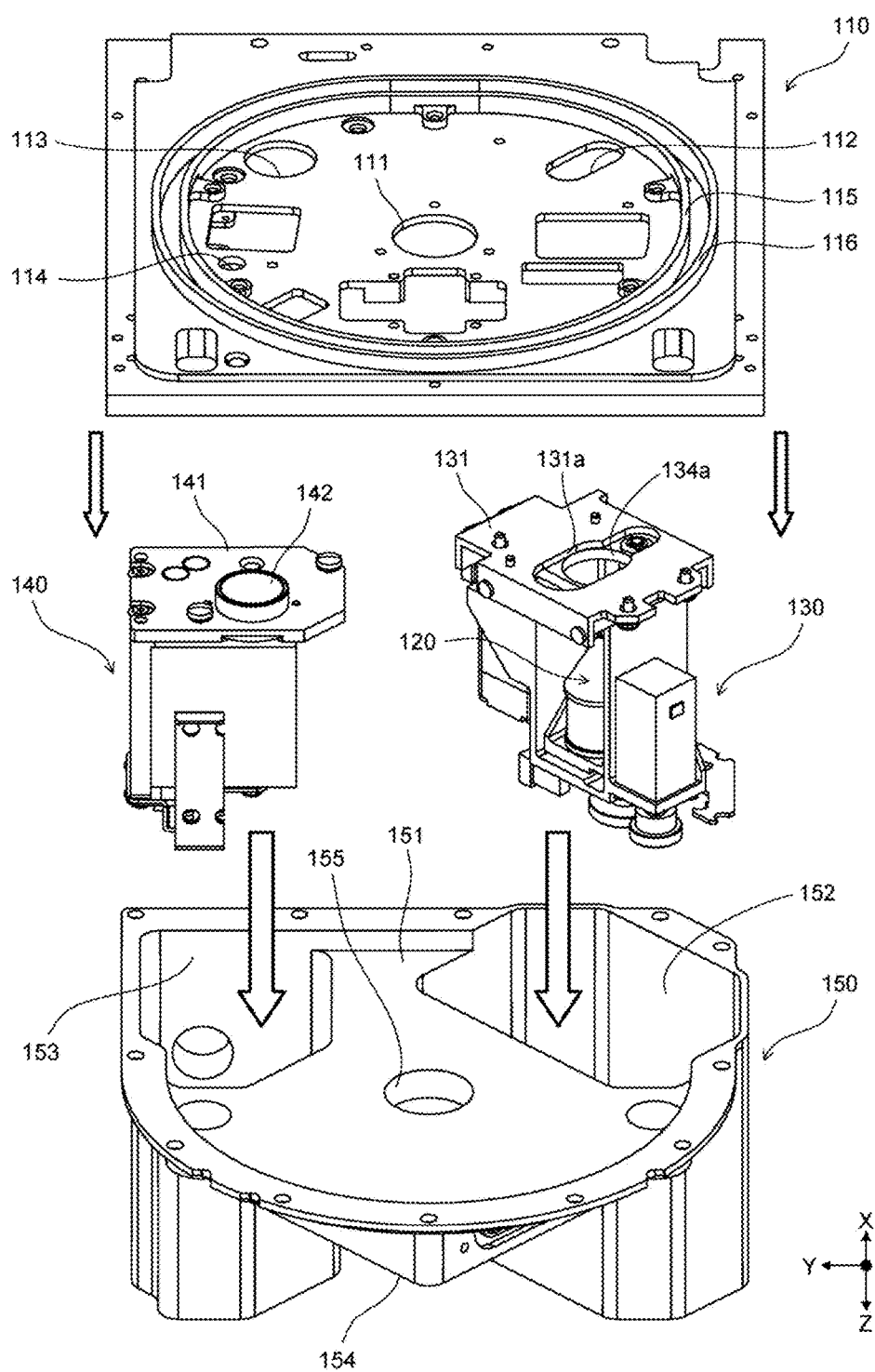
FIG. 3 shows structures of a mounting member, a magnet, a movement mechanism, a detection unit, and a housing according to Embodiment 1 as viewed from diagonally above.

As shown in FIG. 3, holes for passing cables therethrough are provided in the upper face 151 of the housing 150 and the housing portions 152 and 153. These holes can be holes opened in the dark space 340. Therefore, the holes, through which cables or the like for exchanging signals between the inside of the dark space 340 and the outside of the dark space 340 are passed, are all closed by light-shielding members in order to form the dark space 340. For example, in order to shield a gap between a cable and each hole at an outlet of the hole, light-shielding tape, light-shielding cloth, heat-shrinkable tube, grommet, calking material, etc. can be used. The color of these light-shielding members is set to black in order to enhance the light-shielding effect.

When the dark space 340 is formed as described above, the support member 177 for supporting the cartridge 200, the cartridge 200, and the detection face of the photodetector 144a are disposed in the dark space 340. In Embodiment 1, the magnet 120, the movement mechanism 130, and the detection unit 140 are disposed in the dark space 340. Therefore, even when the light generated during the reaction process in the chamber 216 is extremely weak, since external light is prevented from entering the dark space 340, the light generated by the reaction can be accurately detected by the photodetector 144a. Accordingly, accuracy of analyzing the test substance can be improved.

As described above, the motor 171 is disposed outside the dark space 340. The motor 171 is magnetized while rotating the cartridge 200, and generates heat. However, when the motor 171 as a heat source is disposed outside the dark space 340 as a sealed space as described above, the temperature inside the dark space 340 is inhibited from becoming unstable due to the heat of the motor 171. Thus, the temperature of the cartridge 200 can be kept at a desired temperature. Accordingly, the specimen and the reagent in the cartridge 200 are allowed to stably react with each other.

Figure 10A:
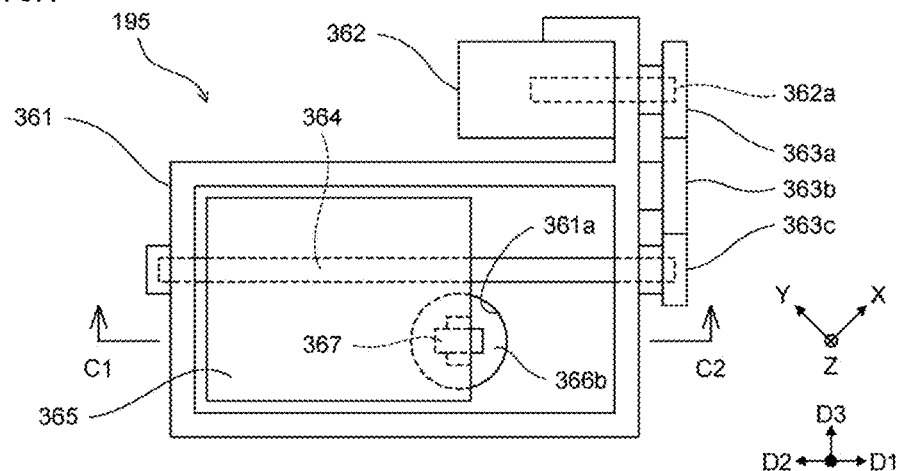
FIG. 10A is a schematic diagram showing a structure of a pressing unit according to Embodiment 1 as viewed from above.
Figure 10A:
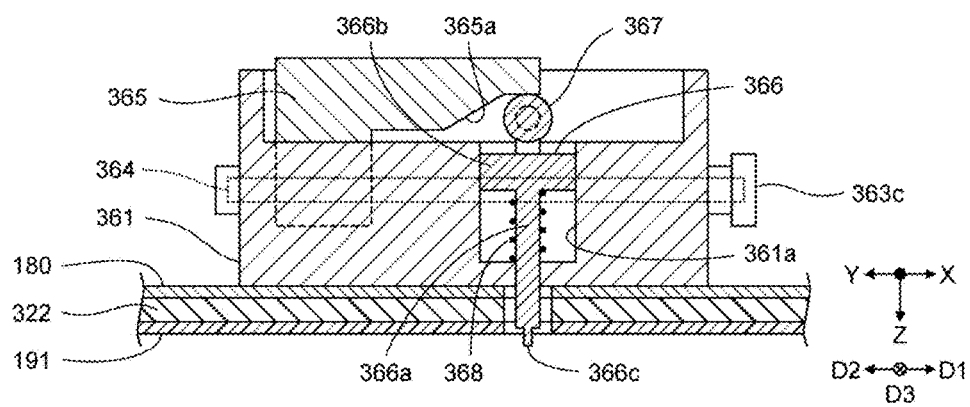
Figure 10A:
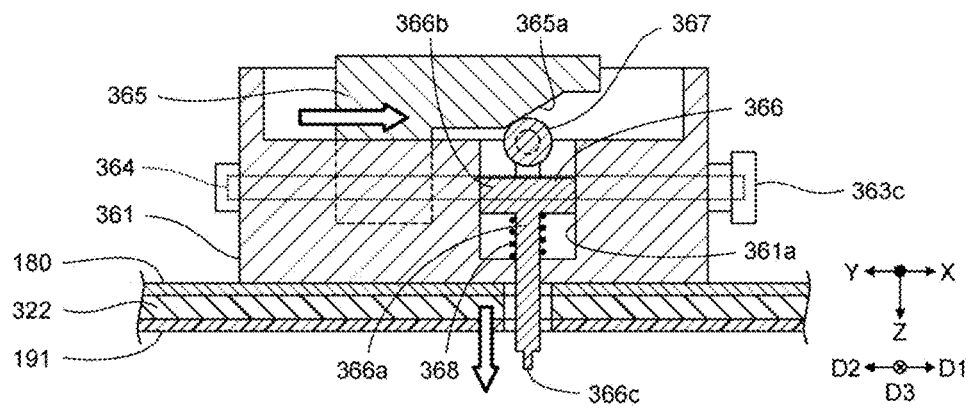

As shown in FIGS. 10A to 10C, the pressing unit 195 includes a mount member 361, a motor 362, transmission gears 363a, 363b, and 363c, a screw 364, a moving member 365, a pin member 366, a roller 367, and a spring 368. In FIGS. 10A to 10C, a D1 direction is a direction obtained by turning the X-axis positive direction, clockwise by 45° around the Z axis. A D2 direction is a direction obtained by turning the Y-axis positive direction, counterclockwise by 45° around the Z axis. A D3 direction is a direction obtained by turning the X-axis positive direction, counterclockwise by 45° around the Z axis. The D3 direction is an outward direction in the radial direction. FIGS. 10B and 10C each are a side view of the pressing unit 195 at a cross-section C1-C2 shown in FIG. 10A, as viewed in the D3 direction.

As shown in FIG. 10B, the mount member 361 is mounted to the upper face of the mounting member 180 of the lid 102. As shown in FIG. 10A, the motor 362 is mounted on the mount member 361. The motor 362 is implemented by a stepping motor. The transmission gears 363a, 363b, and 363c and the screw 364 are supported by the mount member 361 so as to be rotatable around the D1-D2 direction. The transmission gears 363a and 363b are engaged with each other, and the transmission gears 363b and 363c are engaged with each other. A drive shaft 362a of the motor 362 is connected to the transmission gear 363a, and the screw 364 is connected to the transmission gear 363c. The moving member 365 is supported by the screw 364 so as to move in the D1-D2 direction in accordance with rotation of the screw 364. As shown in FIG. 10B, at the lower face of the moving member 365, a cam part 365a is formed which is a plane inclined with respect to a horizontal plane.

As shown in FIGS. 10A and 10B, a cylindrical hole 361a is formed in the mount member 361. As shown in FIG. 10B, the pin member 366 includes: a trunk portion 366a; a flange portion 366b formed at an upper end of the trunk portion 366a; and a leading end portion 366c formed at a lower end of the trunk portion 366a. The trunk portion 366a has a cylindrical shape extending in the Z-axis direction. The flange portion 366b has a cylindrical shape having a diameter that is larger than the diameter of the trunk portion 366a and that is substantially the same as the diameter of the hole 361a. The leading end portion 366c has a cylindrical shape having a diameter that is smaller than the diameter of the trunk portion 366a. The trunk portion 366a is passed through a hole provided at the bottom of the hole 361a, and holes provided so as to correspond to this hole and penetrate the mounting member 180, the heater 322, and the plate member 191.

The roller 367 is rotatably mounted above the pin member 366. The roller 367 has a cylindrical shape. The spring 368 is mounted between a lower face of the flange portion 366b and a bottom of the hole 361a, and pushes the pin member 366 upward in the vertical direction.

When the pressing unit 195 is configured as described above, a driving force is transmitted to the transmission gears 363a, 363b, and 363c and the screw 364 in accordance with driving of the motor 362. Thereby, the moving member 365 is moved in the D1-D2 direction. When the moving member 365 is moved in the D1 direction from the state shown in FIG. 10B, the cam part 365a comes into contact with the roller 367, and pushes the roller 367 downward. Thereby, as shown in FIG. 10C, the pin member 366 is moved downward. When the moving member 365 is moved in the D2 direction from the state shown in FIG. 10C, the cam part 365a is separated from the roller 367, and the spring 368 pushes the pin member 366 upward. Thereby, the pin member 366 is returned to the position shown in FIG. 10B.

When the seal 231a is to be opened, in the state where the pin member 366 is positioned at the upper position as shown in FIG. 10B, the cartridge 200 is rotated by the support member 177, and the seal 231a is positioned directly beneath the leading end portion 366c. The position directly beneath the leading end portion 366c is a position where the pressing unit 195 opens the seal 231a. Then, the motor 362 is driven, and the pin member 366 is moved downward as shown in FIG. 10C. Thereby, the seal 231a positioned directly beneath the leading end portion 366c is pressed by the leading end portion 366c from above, whereby the seal 231a is opened. Also when the seal 232a is to be opened, the seal 232a is positioned directly beneath the leading end portion 366c, and the process of opening the seal by the pressing unit 195 is performed in a similar manner to that for the seal 231a.

As described above, the process of opening the seal 231a, 232a by the pressing unit 195 is performed by the leading end portion 366c pressing the seal 231a, 232a. During the seal opening process, the seal 231a, 232a is pressed from above by the leading end portion 366c with a force of 10N, for example. Such a great force applied to the cartridge 200 may cause displacement of the cartridge 200, unintended deformation of the cartridge 200, etc. In order to inhibit such displacement and deformation, the cartridge 200 is supported from below by the support member 177 at the position of the seal 231a as shown in FIG. 11A.

Figure 11A:
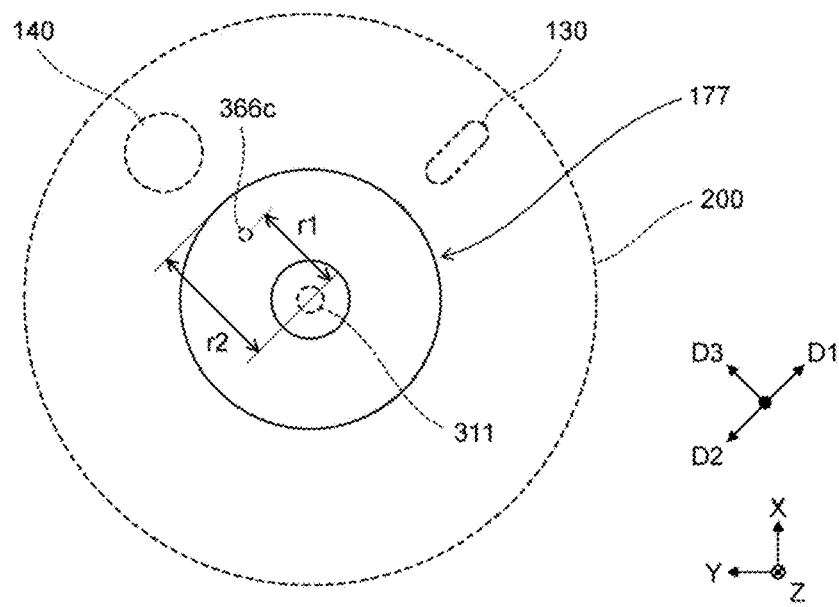
FIG. 11A is a schematic diagram showing a structure of a support member according to Embodiment 1 as viewed from above.

FIG. 11A shows the support member 177 viewed from above. In FIG. 11A, the cartridge 200 mounted on the support member 177 is represented by a broken line for convenience. In addition, portions of the movement mechanism 130 and the detection unit 140, which are directly opposed to the lower face of the cartridge 200 through the holes provided in the plate member 176 shown in FIG. 8, are represented by broken lines for convenience. Further, the rotation shaft 311 and the leading end portion 366c of the pin member 366 are represented by broken lines for convenience.

As shown in FIG. 11A, the distance, from the rotation shaft 311 to the leading end portion 366c in a horizontal plane, is r1. In other words, r1 is the distance from the rotation shaft 311 to a position where the cartridge 200 is pressed by the pressing unit 195. The support member 177 is provided at a position opposed to the pressing unit 195 with the cartridge 200 being located therebetween. Specifically, the support member 177 is a turntable having a radius r2 at least larger than the distance r1, and is provided from the rotation shaft 311 side to the position opposed to the pressing unit 195.

Therefore, even when the pressing unit 195 presses the seal 231a, 232a to open the seal 231a, 232a and thereby the pressing force is applied to the cartridge 200, the support member 177 serves as a base to support the cartridge 200. Accordingly, the cartridge 200 is prevented from displacement and breakage when the seal is opened, and thereby the cartridge 200 is appropriately supported at the predetermined position. Therefore, reduction in measurement accuracy due to the seal opening operation is inhibited.

As shown in FIG. 11A, the radius r2 of the support member 177 is set so that, when viewed from above, the support member 177 does not overlap the portions of the movement mechanism 130 and the detection unit 140, which are directly opposed to the lower face of the cartridge 200. Thus, the magnet 120 is allowed to access the cartridge 200 while the cartridge 200 is placed on the support member 177, whereby magnetic particles collected in one chamber by the magnet 120 can be smoothly transferred to another chamber. Further, since the light from the cartridge 200 is not blocked by the support member 177, detection by the detection unit 140 can be appropriately performed.

If the radius r2 of the support member 177 is set to a larger value within a range that does not cause the support member 177 to overlap the portions of the movement mechanism 130 and the detection unit 140, which are directly opposed to the lower face of the cartridge 200, the support member 177 can support the cartridge 200 more stably. However, with increase in the radius r2 of the support member 177, the load on the motor 171 that rotates the support member 177 is increased. In this case, if the rotation time of the motor 171 is increased or the rotation speed is frequently changed, breakdown of the motor 171 may occur, or the amount of heat generated by the motor 171 may increase. Therefore, the radius r2 of the support member 177 is desirably set to as small a value as possible within a range that covers the position where the support member 177 receives the pressing force from the pressing unit 195.

Even when the radius r2 of the support member 177 is set to as small a value as possible, the area and weight of the support member 177 is increased, compared with the case where a support member simply supports the cartridge 200. In this case, the size of the motor 171 that drives the support member 177 is increased, and the amount of heat generated by the motor 171 is increased. However, since the motor 171 is disposed outside the dark space 340 as described above, even when the amount of heat generated by the motor 171 is increased, the temperature inside the dark space 340 is inhibited from being unstable, whereby measurement can be appropriately proceeded.

Figure 11B:
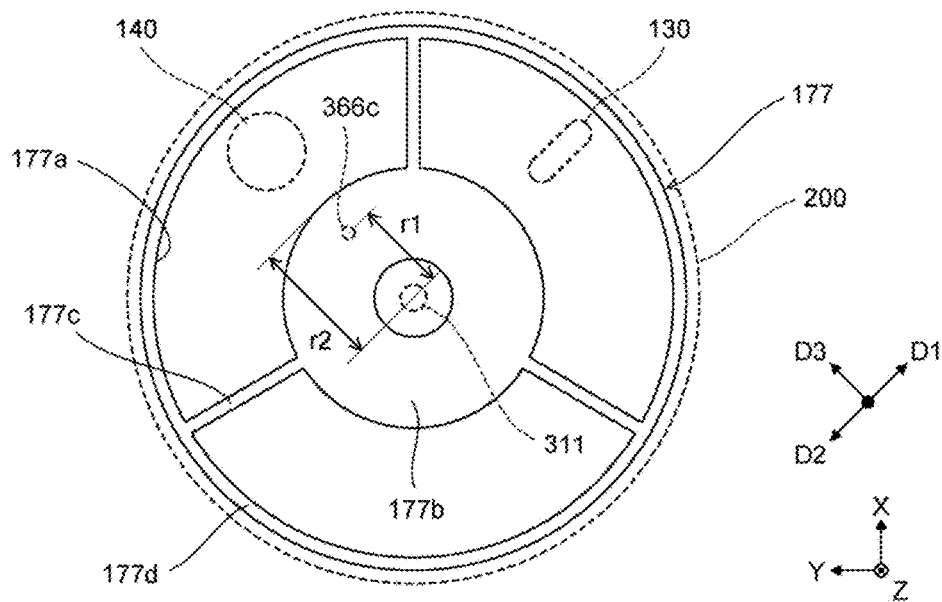
FIG. 11B is a schematic diagram showing a structure of a support member according to a modification of Embodiment 1 as viewed from above.

As shown in FIG. 11B, the radius of the outermost circumferential portion of the support member 177 may be set to substantially the same value as the radius of the cartridge 200. In this case, the support member 177 is provided with, for example, three holes 177a penetrating the support member 177 in the Z-axis direction. In a direction inward from the three holes 177a, an inner circumferential part 177b having a radius of r2 is provided, as in FIG. 11A. A connection part 177c is provided in the radial direction between adjacent two holes 177a. By the three connection parts 177c, an outer circumferential part 177d positioned at the outermost circumference of the support member 177 is supported.

The size of each hole 177a is set so that the portions of the movement mechanism 130 and the detection unit 140, which are opened upward, are directly opposed to the lower face of the cartridge 200 through the holes 177a. In addition, the size of each hole 177a is set so that the chambers 211 to 216 and the channel 220 do not overlap the support member 177 when the cartridge 200 is placed on the support member 177.

When the support member 177 is configured as shown in FIG. 11B, as in the case of FIG. 11A, the lower face of the cartridge 200 positioned beneath the seals 231a and 232a can be supported by the inner circumferential part 177b. Further, in the case of FIG. 11B, since the cartridge 200 is supported by the outer circumferential part 177d at the outer circumference thereof, the cartridge 200 can be supported stably compared with the case of FIG. 11A.

In the case where the cartridge 200 is placed at a predetermined position on the support member 177, the shape of the support member 177 shown in FIG. 11A and the shapes of the inner circumferential part 177b and the outer circumferential part 177d shown in FIG. 11B may not be necessarily round.

Figure 12A:
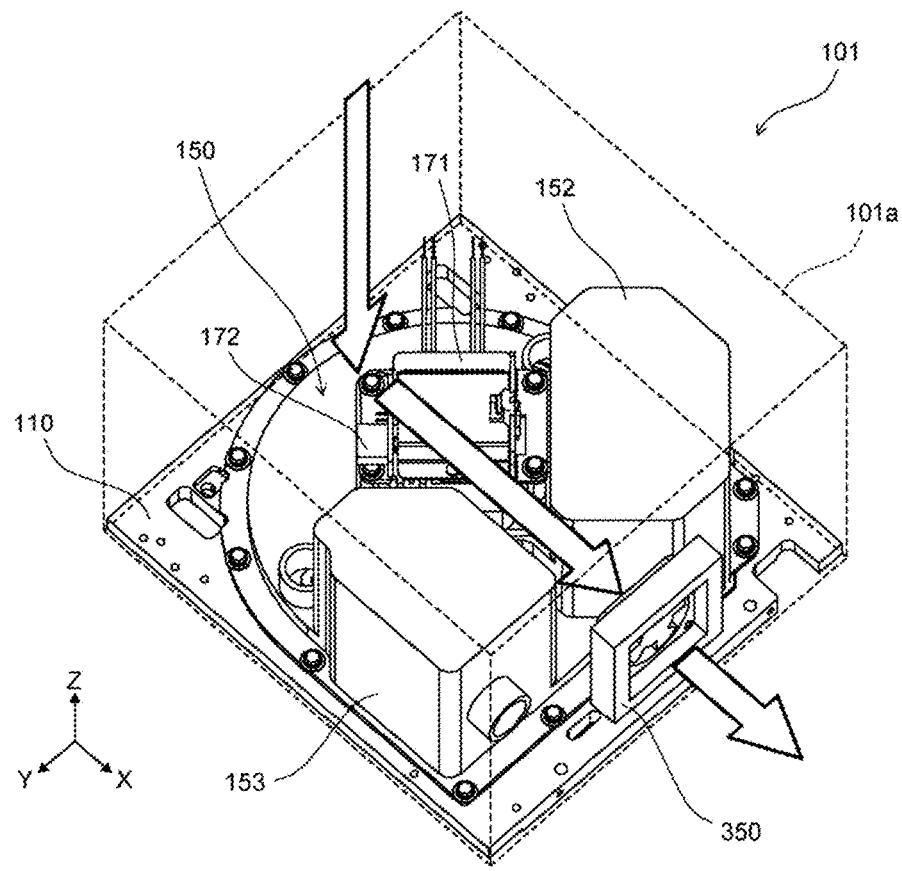
FIG. 12A shows an internal structure of the body according to Embodiment 1 as viewed from below.
Figure 12B:
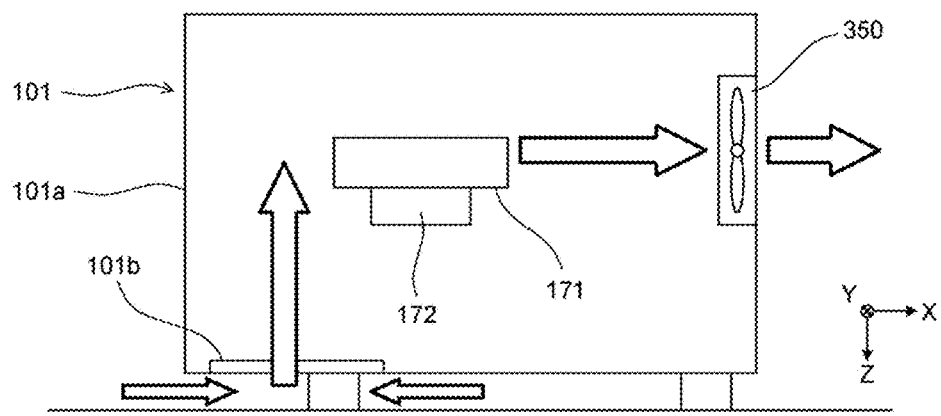
FIG. 12B is a schematic diagram showing the internal structure of the body according to Embodiment 1 as viewed from the side thereof.

As shown in FIGS. 12A and 12B, the ventilation unit 350 is mounted on a rear face of the casing 101a of the body 101. The ventilation unit 350 is implemented by a fan. The ventilation unit 350 discharges heat generated by the motor 171 mounted on the outer face 154 of the housing 150, to the outside of the analyzer 100. A bottom face of the casing 101a of the body 101 is separated by a predetermined distance from the installation surface by means of leg parts. A ventilation hole 101b is provided at a front portion of the bottom face of the casing 101a. When the ventilation unit 350 is driven, air, which is taken in from the ventilation hole 101b, passes the motor 171 and is discharged rearward of the analyzer 100, as shown by white arrows. Alternatively, air, which is taken in from the outside at the position of the ventilation unit 350, may pass the motor 171 to be discharged from the ventilation hole 101b, in a direction opposite to the direction of the white arrows.

In a plan view, that is, when viewed in the vertical direction, the outline of the body 101 has a rectangular shape, and the outline of the motor 171 also has a rectangular shape. The motor 171 is disposed in the body 101 so that the corners of the motor 171 and the corners of the body 101 are displaced from each other in a plan view. Further, in a plan view, in a space between the motor 171 and a corner of the body 101, the detection unit 140 including the photodetector 144a is disposed. Likewise, in a plan view, in a space between the motor 171 and another corner of the body 101, the magnet 120 and the movement mechanism 130 are disposed. Thereby, the shape of the body 101 in a plan view can be made compact, and therefore, the analyzer 100 can be downsized.

In the housing 150, the housing portions 152 and 153 for housing the members to be disposed in the dark space 340 are formed. The housing portions 152 and 153 each have a shape with an outer face thereof, on the motor 171 side, being protruded. The motor 171 is disposed laterally to the housing portion 152 with a gap from the housing portion 152, and is disposed laterally to the housing portion 153 with a gap from the housing portion 153. That is, the motor 171 is disposed on the outer face 154. By disposing the motor 171 laterally to the housing portions 152 and 153 as described above, the size of the analyzer 100 is prevented from being increased in the height direction. In addition, since the gaps are formed between the housing portion 152 and the motor 171 and between the housing portion 153 and the motor 171, respectively, convection of air can be generated in these gaps as shown in FIGS. 12A and 12B. Accordingly, heat of the motor 171 can be effectively removed.

The housing portions 152 and 153 are formed in the housing 150 with a gap therebetween. The motor 171 is disposed to be sandwiched by the housing portion 152 and the housing portion 153. The ventilation unit 350 is disposed to oppose the gap between the housing portions 152 and 153. Thus, air is allowed to easily pass around the motor 171 through the gap between the housing portions 152 and 153, whereby heat of the motor 171 can be effectively removed.

The ventilation unit 350 is disposed at a position at the same height level as the motor 171 so as to oppose the motor 171. Thus, air around the motor 171 is easily guided to the outside of the analyzer 100, and therefore, heat generated in the motor 171 can be efficiently discharged. As described above, the motor 171 is disposed outside the dark space 340, and the ventilation unit 350 is also disposed outside the dark space 340. Therefore, temperature rise inside the dark space 340 can be effectively inhibited without impairing the light-shielding effect of the light-shielding portions that form the dark space 340.

Further, in Embodiment 1, upon receiving an analysis start instruction, the controller 301 described later drives the heaters 321 and 322 to raise the temperature of the cartridge 200. At this time, the controller 301 controls the operation of the ventilation unit 350 on the basis of the temperature of the cartridge 200 detected by the temperature sensor 178. For example, the controller 301 causes the ventilation unit 350 to stop when the temperature of the cartridge 200 is less than 40° C., and drives the ventilation unit 350 when the temperature of the cartridge 200 exceeds 40° C. Thereby, the time until the temperature of the cartridge 200 is converged to 42° C. can be reduced, compared with the case where the ventilation unit 350 is driven immediately after reception of the analysis start instruction, whereby power consumption of the ventilation unit 350 and the heaters 321 and 322 can be reduced.

As shown in FIG. 13, the analyzer 100 includes, as described above, the motors 135, 136, 161, and 171, the encoder 172, the heaters 321 and 322, the temperature sensors 331, 332, and 178, the light detection unit 144, the ventilation unit 350, the image capturing unit 193, the lighting unit 194, and the pressing unit 195. The analyzer 100 further includes the controller 301, a display unit 302, an input unit 303, a driving unit 304, and a sensor unit 305. The controller 301 includes, for example, an arithmetic processor and a storage unit. The arithmetic processor is implemented by, for example, a CPU or an MPU. The storage unit is implemented by, for example, a flash memory or a hard disk. The controller 301 receives signals from the respective components of the analyzer 100, and controls the respective components of the analyzer 100. The display unit 302 and the input unit 303 are provided at, for example, a lateral face portion of the body 101 or an upper face portion of the lid 102. The display unit 302 is implemented by, for example, a liquid crystal panel. The input unit 303 is implemented by, for example, buttons or a touch panel. The driving unit 304 includes other mechanisms disposed in the analyzer 100. The sensor unit 305 includes: a sensor for detecting a predetermined portion of the rotating cartridge 200; a sensor for detecting mechanisms that are moved to original positions by the motors 135, 136, and 161; and other sensors disposed in the analyzer 100.

Hereinafter, an operation of the analyzer 100 is described with reference to FIG. 14.

First, an operator infuses a blood specimen collected from a subject into the cartridge 200 through the opening 241, and places the cartridge 200 on the support member 177. A test substance in the blood specimen contains an antigen, for example. An example of the antigen is hepatitis B surface antigen (HBsAg). The test substance may be one or more of an antigen, an antibody, and another protein.

Predetermined reagents are stored in the liquid storage portions 231 and 232 and the chamber 211 of the cartridge 200 in advance. Specifically, an R1 reagent is stored in the liquid storage portion 231 positioned in the radial direction of the chamber 211. An R2 reagent is stored in the chamber 211. An R3 reagent is stored in the liquid storage portion 231 positioned in the radial direction of the chamber 212. A washing liquid is stored in the liquid storage portions 231 positioned in the radial directions of the chambers 213 to 215. An R4 reagent is stored in the liquid storage portion 231 positioned in the radial direction of the chamber 216. An R5 reagent is stored in the liquid storage portion 232.

In a control described below, the controller 301 obtains a rotation position of the drive shaft 171a of the motor 171 on the basis of an output signal from the encoder 172 connected to the motor 171. The controller 301 obtains the position of the cartridge 200 in the circumferential direction by detecting, with the sensor, a predetermined portion of the rotating cartridge 200. Alternatively, the cartridge 200 may be placed at a predetermined position with respect to the support member 177. Thus, the controller 301 can position the respective components of the cartridge 200 at predetermined positions in the circumference direction.

In addition, the controller 301 obtains the positions of the respective mechanisms moved by the motors 135, 136, and 161, on the basis of an output signal from the sensors for detecting the mechanisms moved to the original positions by the motors 135, 136, and 161. Thus, the controller 301 can locate, as predetermined positions, the mechanisms moved by the motors 135, 136, and 161, that is, the magnet 120 and the plate-shaped member 162.

In step S11, the controller 301 receives a start instruction made by the operator via the input unit 303, and starts processes of step S12 and thereafter.

In step S12, the controller 301 transfers the plasma and the reagents to the chambers. Specifically, the controller 301 drives the motor 171 to rotate the cartridge 200, thereby driving the pressing unit 195 to press, downward, each of the six seals 231a located at the position opposed to the pressing unit 195. Then, the controller 301 drives the motor 171 to rotate the cartridge 200, thereby transferring the plasma positioned in the region 243b to the chamber 211 by a centrifugal force, and transferring the reagents stored in the six liquid storage portions 231 to the chambers 211 to 216. Thus, the plasma, the R1 reagent, and the R2 reagent are mixed together in the chamber 211. The R3 reagent is transferred to the chamber 212, the washing liquid is transferred to the chambers 213 to 215, and the R4 reagent is transferred to the chamber 216.

Further, in step S12, when transfer of the plasma and the reagents is completed, the controller 301 performs an agitation process. Specifically, the controller 301 drives the motor 171 so as to switch the rotation speed of the motor 171 between two different rotation speeds at predetermined time intervals while rotating the motor 171 in a predetermined direction. For example, the controller 301 performs the agitation process by switching the current applied to the motor 171 at the predetermined time intervals or by switching driving of the motor 171 between ON and OFF at the predetermined time intervals. Thereby, an Euler force generated in the circumferential direction is changed at the predetermined time intervals, whereby the liquids in the chambers 211 to 216 are agitated. This agitation process is performed not only in step S12 but also in steps S13 to S18 in a similar manner after the transfer process.

The controller 301 may perform the agitation process by switching the rotation direction of the motor 171 at the predetermined time intervals. However, if the motor 171 is driven in such a manner, the load on the motor 171 is increased. Therefore, the motor 171 is preferably driven with the rotation speed being switched between two rotation speeds while being rotated in the predetermined direction, as described above.

The R1 reagent contains a capture substance that binds to the test substance. The capture substance contains, for example, an antibody that binds to the test substance. The antibody is, for example, a biotin-bound HBs monoclonal antibody. The R2 reagent contains magnetic particles in a liquid component thereof. The magnetic particles are, for example, streptavidin-bound magnetic particles, the surfaces of which are coated with avidin. In step S12, when the plasma, the R1 reagent, and the R2 reagent are mixed together and the agitation process is performed, the test substance and the R1 reagent are bound to each other through an antigen-antibody reaction. Then, through a reaction between an antigen-antibody reaction product and the magnetic particles, the test substance bound to the capture substance of the R1 reagent is bound to the magnetic particles via the capture substance. Thus, a complex in which the test substance and the magnetic particles are bound to each other is generated.

Next, in step S13, the controller 301 causes the complex in the chamber 211 to be transferred from the chamber 211 to the chamber 212. Thereby, the complex generated in the chamber 211 and the R3 reagent are mixed together in the chamber 212. The R3 reagent contains a labeling substance. The labeling substance contains: a capture substance that specifically binds to the test substance; and a label. For example, the labeling substance is a labeled antibody in which an antibody is used as a capture substance. In step S13, when the complex generated in the chamber 211 and the R3 reagent are mixed together and the agitation process is performed, the complex generated in the chamber 211 reacts with the labeled antibody contained in the R3 reagent. Thereby, a complex in which the test substance, the capture antibody, the magnetic particles, and the labeled antibody are combined is generated.

The process in step S13 is described in detail with reference to FIG. 15. FIG. 15 shows a flowchart for explaining step S13 in FIG. 14 in detail. In the following description, FIG. 15 is mainly referred to, and state transition diagrams shown in FIG. 16A to FIG. 17C are referred to when necessary.

Figure 16A:
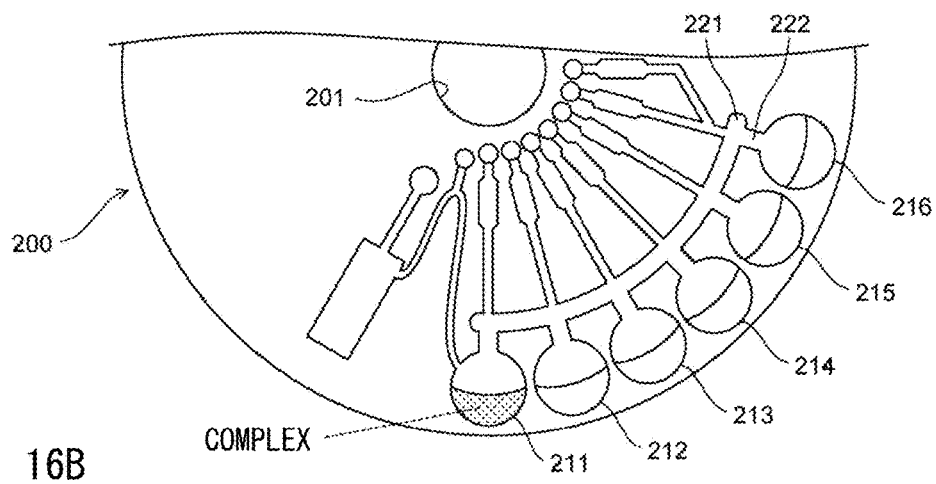
FIGS. 16A to 16C schematically show a state transition in which a complex is transferred between chambers adjacent to each other, according to Embodiment 1.
Figure 16B:
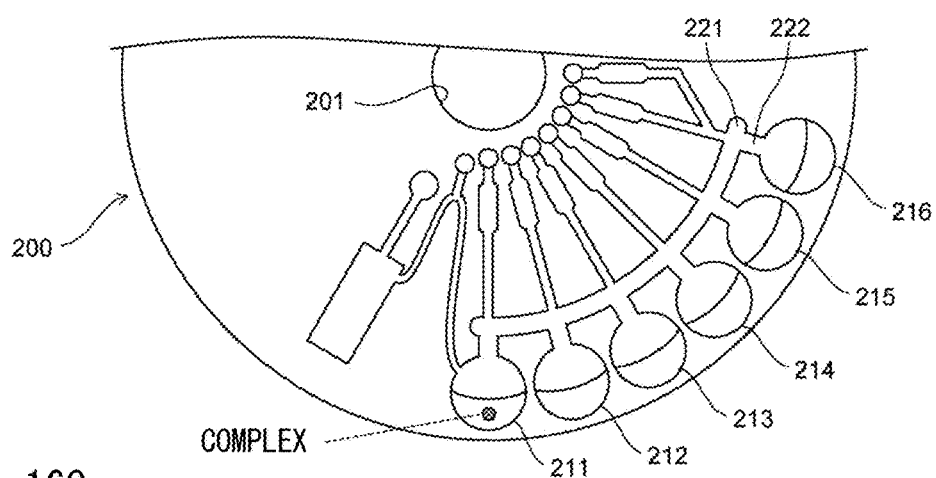

At the time point when the process of step S12 is completed, the complex spreads in the chamber 211 as shown in FIG. 16A. In step S101, the controller 301 drives the movement mechanism 130 to move the magnet 120 close to the cartridge 200, thereby collecting the complex that spreads in the chamber 211, as shown in FIG. 16B. At this time, the controller 301 causes the tip portion 122a of the magnet 120 to move close to a region that is at the center of the chamber 211 in the circumferential direction and is near the outer side of the chamber 211 in the radial direction, in a horizontal plane.

In Embodiment 1, the amount of the mixture containing the complex, which is stored in the chamber 211, is less than the full capacity of the chamber 211. When the amount of the mixture stored in the chamber 211 is less than the full capacity of the chamber 211, it is assumed that a region, in the chamber 211, where the mixture is present varies. However, if a centrifugal force is applied to the chamber 211 in the agitation process after the test substance, the R1 reagent, and the R2 reagent have been mixed together in the chamber 211 as described above, the mixture is always unevenly distributed to the outer side in the chamber 211. Therefore, when the complex in the chamber 211 is collected by using the magnet 120, if the tip portion 122a of the magnet 120 is positioned at the region, in the chamber 211, where the unevenly distributed mixture is stored, that is, the region near the outer side in the chamber 211, the complex in the mixture stored in the chamber 211 can be reliably collected to the position of the magnet 120.

The amount of the mixture containing the complex stored in each of the chambers 212 to 215 is also less than the full capacity of the chamber. Therefore, if the magnet 120 is positioned at the region near the outer side in each chamber as in the case of the chamber 211, the complex contained in the mixture in each of the chambers 212 to 215 can be reliably collected to the position of the magnet 120.

Figure 16C:
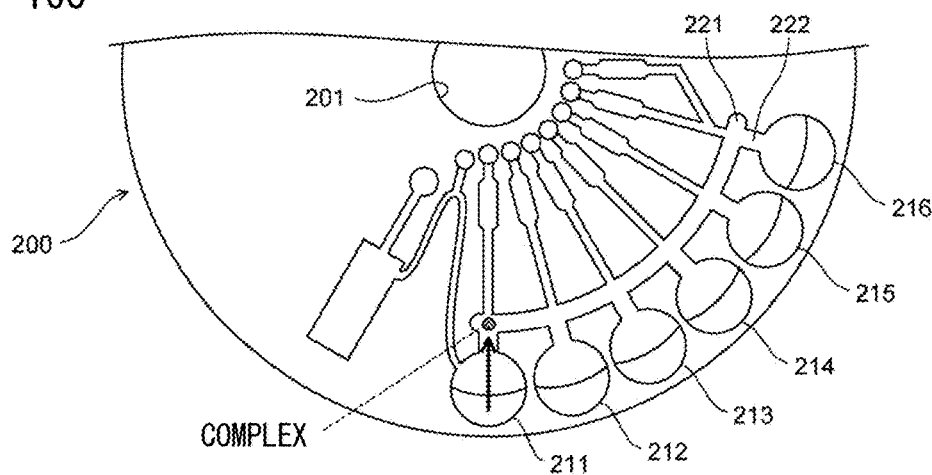

In step S102, the controller 301 drives the movement mechanism 130 to move the magnet 120 in a direction approaching the rotation shaft 311, thereby transferring the complex to a connection portion between the region 221 and the region 222 that is connected to the chamber 211 as shown in FIG. 16C. The speed at which the complex is moved with respect to the cartridge 200 in step S102 is preferably not higher than 10 mm/sec to prevent the complex from being left in the chamber 211. Specifically, the speed is 0.5 mm/sec, for example. Movement of the magnet 120 by the movement mechanism 130 is performed so as to realize the above-described movement speed of the complex.

Figure 17A:
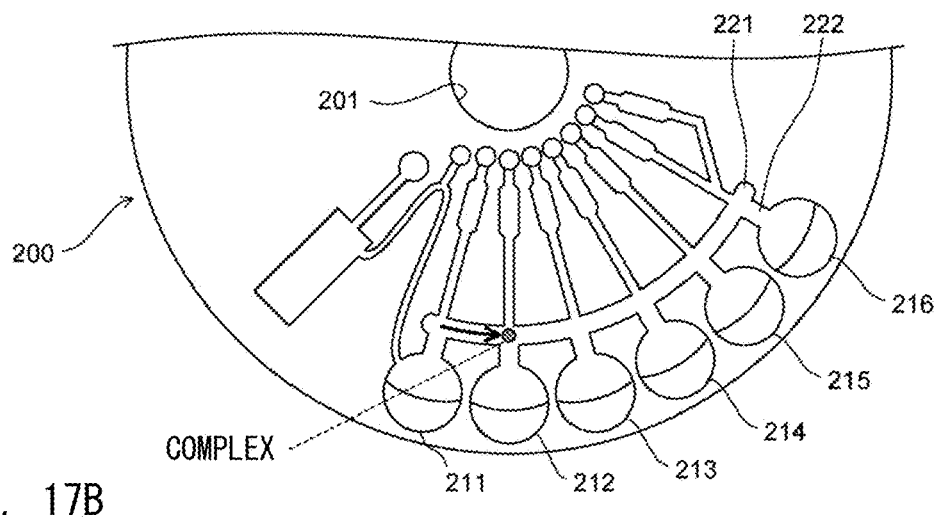
FIGS. 17A to 17C schematically show a state transition in which the complex is transferred between the chambers adjacent to each other, according to Embodiment 1.

In step S103, the controller 301 drives the motor 171 to rotate the cartridge 200, thereby transferring the complex to a connection portion between the region 221 and the region 222 that is connected to the chamber 212 as shown in FIG. 17A. The speed at which the complex is moved with respect to the cartridge 200 in step S103 is also set as in the case of step S102. Rotation of the cartridge 200 by the motor 171 is performed so as to realize the above-described movement speed of the complex.

Figure 17B:
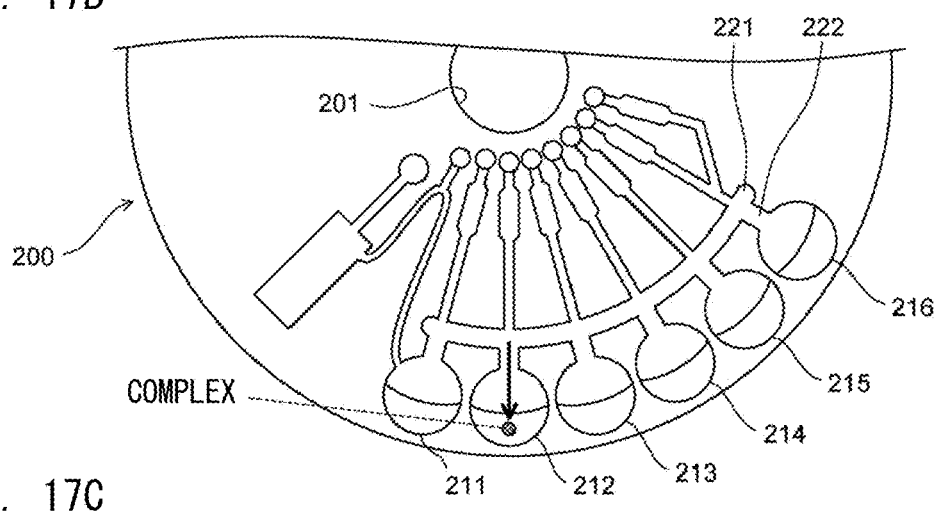
Figure 17C:
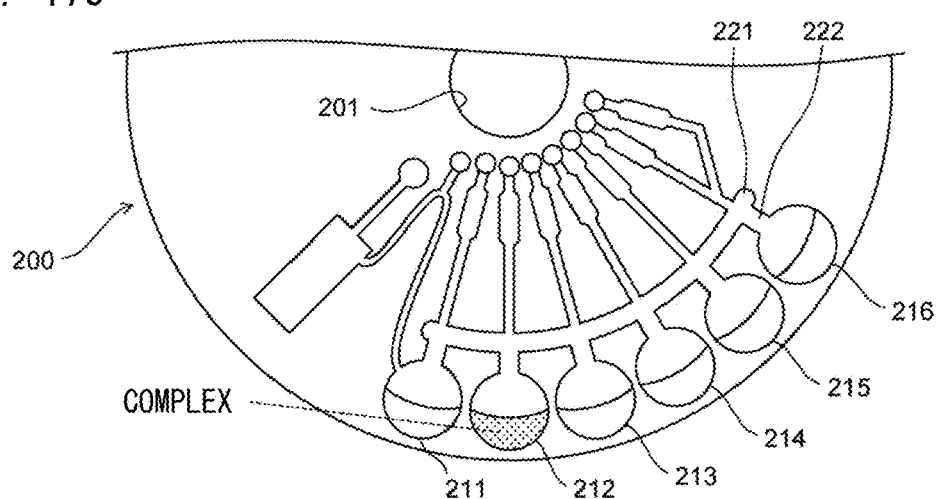

In step S104, the controller 301 drives the movement mechanism 130 to move the magnet 120 in a direction away from the rotation shaft 311, thereby transferring the complex to the chamber 212 as shown in FIG. 17B. The speed at which the complex is moved with respect to the cartridge 200 in step S104 is also set as in the case of step S102. In step S105, the controller 301 drives the movement mechanism 130 so as to move the magnet 120 away from the cartridge 200, thereby causing the complex to spread in the chamber 212 as shown in FIG. 17C.

As described above, in steps S101 to S105, the controller 301 causes the magnet 120 to move close to the cartridge 200 at the position opposed to the chamber 211, and thereafter causes the magnet 120 to move along the channel 220 while keeping the magnet 120 close to the cartridge 200, thereby locating the magnet 120 at the position opposed to the chamber 212. Thereafter, the controller 301 causes the magnet 120 to move away from the cartridge 200 to release magnetic attraction of the complex by the magnet 120. Thus, the complex is reliably prevented from being left in the chamber 211 and the channel 220.

In step S106, the controller 301 performs the above-described agitation process. At this time, since magnetic attraction of the complex has been released before the agitation process and therefore the complex spreads in the chamber 212, agitation of the liquid in the chamber 212 is reliably performed.

Figure 14:
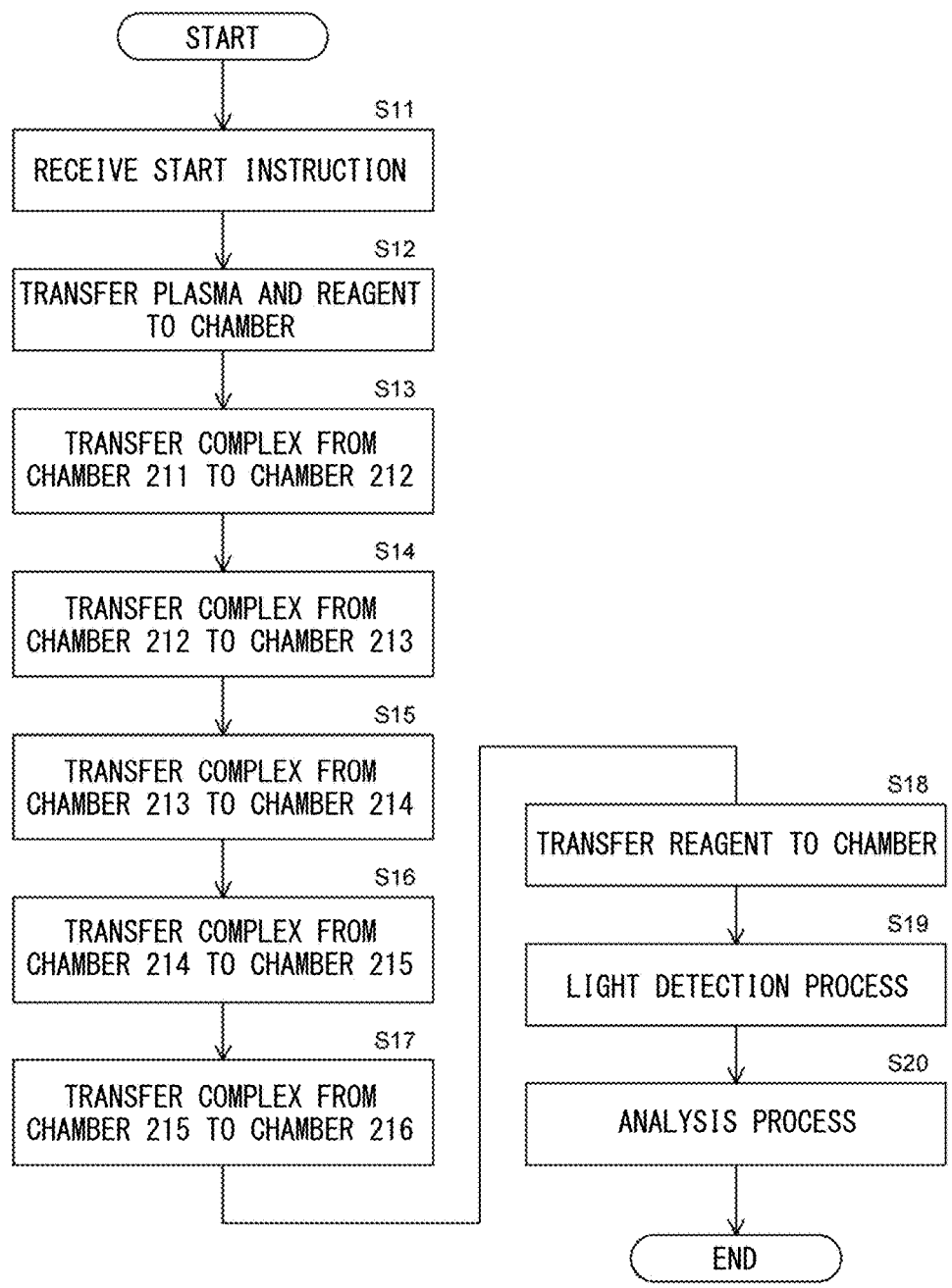
FIG. 14 is a flow chart showing an operation of the analyzer according to Embodiment 1.
Figure 15:
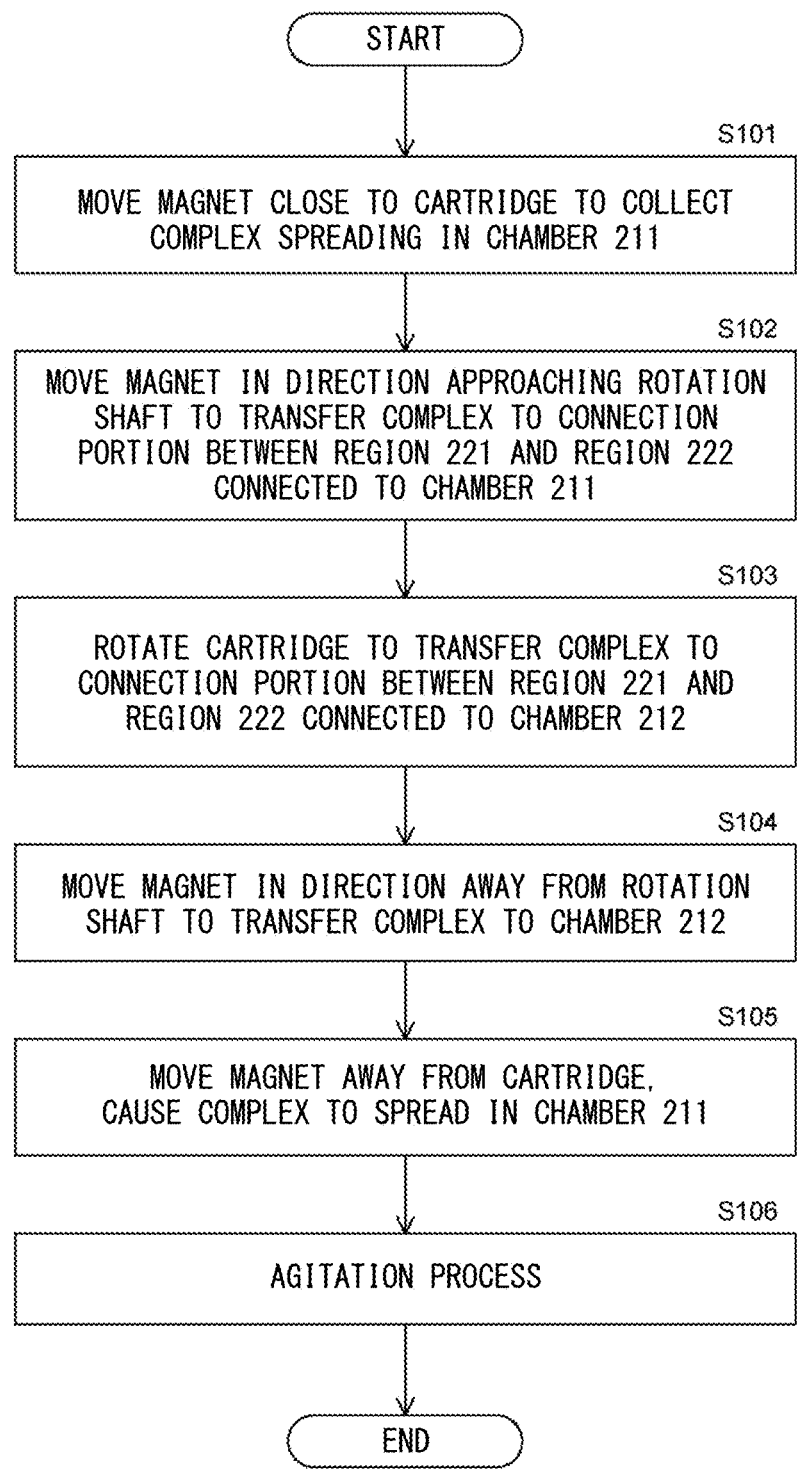
FIG. 15 is a flow chart showing an operation of the analyzer in the case where a complex is transferred between chambers adjacent to each other, according to Embodiment 1.

The process in step S13 shown in FIG. 14 is performed as described above. The transfer process and the agitation process described in steps S101 to S106 are similarly performed also in each of steps S14 to S17 described later.

Returning to FIG. 14, in step S14, the controller 301 causes the complex stored in the chamber 212 to be transferred from the chamber 212 to the chamber 213. Thereby, the complex generated in the chamber 212 and the washing liquid are mixed together in the chamber 213. In step S14, when the complex generated in the chamber 212 and the washing liquid are mixed together and the agitation process is performed, the complex and unreacted substance are separated from each other in the chamber 213. That is, in the chamber 213, the unreacted substance is removed by washing.

In step S15, the controller 301 causes the complex in the chamber 213 to be transferred from the chamber 213 to the chamber 214. Thereby, the complex generated in the chamber 212 and the washing liquid are mixed together in the chamber 214. Also in the chamber 214, unreacted substance is removed by washing.

In step S16, the controller 301 causes the complex in the chamber 214 to be transferred from the chamber 214 to the chamber 215. Thereby, the complex generated in the chamber 212 and the washing liquid are mixed together in the chamber 215. Also in the chamber 215, unreacted substance is removed by washing.

In step S17, the controller 301 causes the complex in the chamber 215 to be transferred from the chamber 215 to the chamber 216. Thereby, the complex generated in the chamber 212 and the R4 reagent are mixed together in the chamber 216. The R4 reagent is a reagent for dispersing the complex generated in the chamber 212. The R4 reagent is a buffer solution, for example. In step S17, when the complex generated in the chamber 212 and the R4 reagent are mixed together and the agitation process is performed, the complex generated in the chamber 212 is dispersed.

In step S18, the controller 301 causes the R5 reagent to be transferred to the chamber 216. Specifically, the controller 301 drives the motor 171 to rotate the cartridge 200, thereby driving the pressing unit 195 to press, downward, the seal 232a located at the position opposed to the pressing unit 195. Then, the controller 301 drives the motor 171 to rotate the cartridge 200, thereby transferring the R5 reagent stored in the liquid storage portion 232 to the chamber 216 by a centrifugal force. Thus, in the chamber 216, the R5 reagent is further mixed with the mixture obtained in step S17.

The R5 reagent is a luminescent reagent containing a luminescent substrate that generates light through a reaction with the labeled antibody bound to the complex. In step S18, the mixture obtained in step S17 and the R5 reagent are mixed together, and the agitation process is performed, whereby a sample is prepared. This sample causes chemiluminescence when the labeling substance bound to the complex reacts with the luminescent substrate.

In step S19, the controller 301 drives the motor 171 to locate the chamber 216 at the position directly above the photodetector 144a, and causes the photodetector 144a to detect light generated from the chamber 216. In step S20, the controller 301 performs an analysis process regarding immunity, on the basis of the light detected by the photodetector 144a. When the photodetector 144a is implemented by a photo multiplier tube, a pulse wave in response to reception of photons is outputted from the photodetector 144a. The light detection unit 144 counts the photons at regular intervals on the basis of the output signal from the photodetector 144a, and outputs the count value. The controller 301 analyzes whether or not the test substance is present, the amount of the test substance, and the like on the basis of the count value outputted from the light detection unit 144, and causes the display unit 302 to display analysis results.

As described above, the complex is sequentially transferred through the chambers 211 to 216. When the complex is thus transferred through the plurality of chambers, the complex is likely to be left in the chambers 211 to 215 and the channel 220. However, when the complex is reliably transferred by using the magnet 120 as described above, the complex is reliably prevented from being left behind. Thus, unintended reduction in the amount of light detected by the photodetector 144a can be inhibited. Accordingly, false negative due to unintended reduction in the amount of light can be inhibited, thereby realizing highly accurate detection.

Chemiluminescence is light generated by using energy caused by a chemical reaction. For example, chemiluminescence is light that is emitted when molecules, which have been excited by the chemical reaction and entered an excited state, return to a ground state from the excited state. Chemiluminescence can be generated by: a reaction between an enzyme and a substrate; application of electrochemical stimulation to a labeling substance; LOCI (Luminescent Oxygen Channeling Immunoassay) or bioluminescence. In Embodiment 1, chemiluminescence may be performed by any means.

Any magnetic particles may be used as long as the magnetic particles contain, as a base, a material having magnetic properties and are used in conventional immunoassay. For example, magnetic particles containing, as a base, $Fe_2O_3$ and/or $Fe_3O_4$, cobalt, nickel, ferrite, magnetite, or the like can be used. The magnetic particles may be coated with a binding substance for binding the magnetic particles to the test substance. Alternatively, the magnetic particles may be bound to the test substance via a capture substance for binding the magnetic particles to the test substance. The capture substance is an antigen, an antibody, or the like that binds the magnetic particles and the test substance mutually to each other.

The labeling substance contains, for example, a capture substance that specifically binds to the test substance, and a label for chemiluminescence. The capture substance is not particularly limited as long as the capture substance specifically binds to the test substance. In Embodiment 1, the capture substance binds to the test substance through an antigen-antibody reaction. More specifically, although the capture substance is an antibody in Embodiment 1, if the test substance is an antibody, the capture substance may be an antigen for the antibody. When the test substance is a nucleic acid, the capture substance may be a nucleic acid that is complementary to the test substance. Examples of the label contained in the labeling substance include an enzyme, a fluorescent substance, a radioisotope, and the like. Examples of the enzyme include alkaline phosphatase (ALP), peroxidase, glucose oxidase, tyrosinase, acid phosphatase, and the like. When the chemiluminescence is electrochemiluminescence, any substance may be adopted as the label as long as the substance emits light by electrochemical stimulation. For example, a ruthenium complex may be adopted. Examples of the fluorescent substance include fluorescein isothiocyanate (FITC), green fluorescence protein (GFP), luciferin, and the like. Examples of the radioisotope include 125I, 14C, 32P, and the like.

When the label is an enzyme, a luminescent substrate for the enzyme may be appropriately selected from well-known luminescent substrates according to the enzyme. When the enzyme is alkaline phosphatase, examples of the luminescent substrate include: chemiluminescent substrates such as CDP-Star (registered-trademark), (disodium 4-chloro-3-(methoxyspiro[1,2-dioxetane-3,2'-(5'-chloro)tricyclo [3.3.1.1$^{3,7}$]decan]-4-yl)phenylphosphate), and CSPD (registered-trademark) (disodium 3-(4-methoxyspiro[1,2-dioxetane-3,2-(5'-chloro)tricyclo[3.3.1.1$^{3,7}$]decane]-4-yl) phenylphosphate); luminescent substrates such as p-nitrophenyl phosphate, 5-bromo-4-chloro-3-indolyl phosphate (BCIP), 4-nitro blue tetrazolium chloride (NBT) and iodonitrotetrazolium (INT); fluorescent substrates such as 4-methylumbelliferyl phosphate (4MUP); chromogenic substrates such as 5-bromo-4-chloro-3-indolyl phosphate (BCIP), disodium 5-bromo-6-chloro-indolyl phosphate, and p-nitrophenyl phosphate; and the like.

<Examinations Regarding Reflection Member>

The inventors have conducted various examinations regarding the operations and effects of the reflection member 142, and preferable design conditions for the reflection member 142.

Figure 18A:
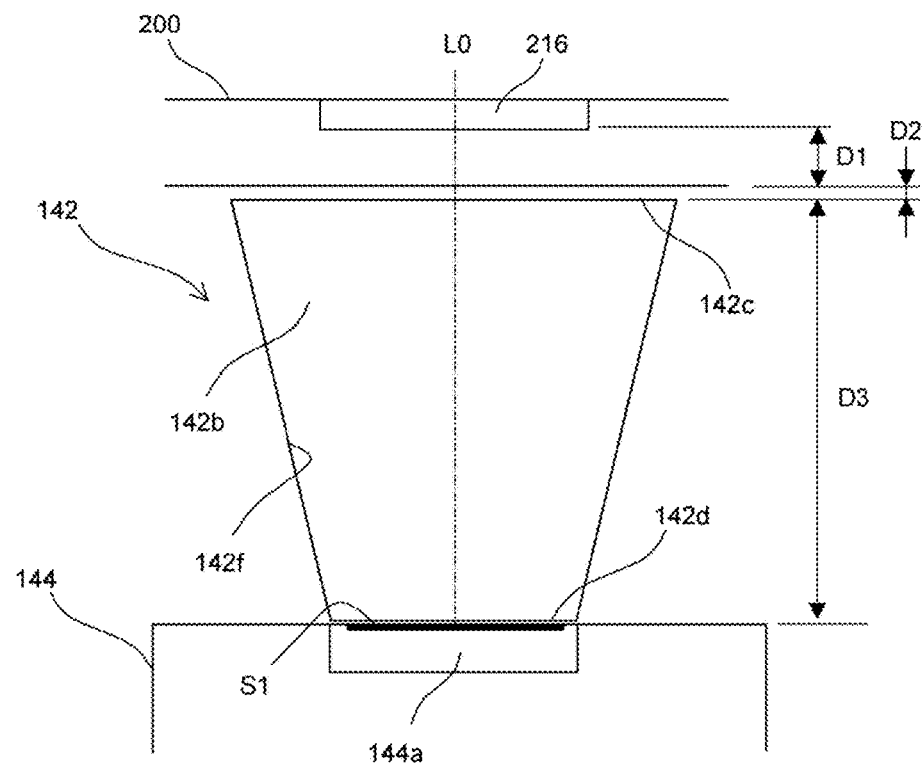
FIG. 18A shows a structure of a reflection member and the vicinity thereof in a perspective view from the side thereof, the reflection member being used for verification according to Embodiment 1.
Figure 18B:
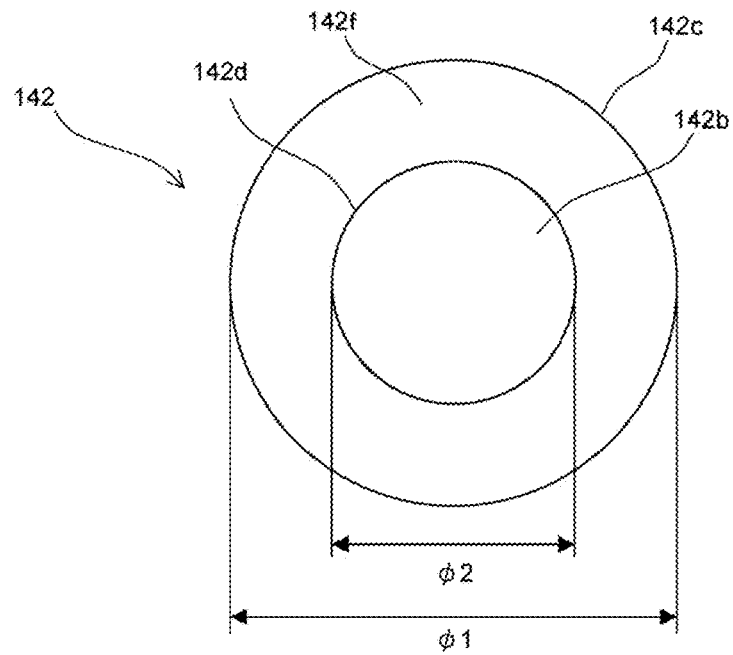
FIG. 18B shows the reflection member used for the verification according to Embodiment 1 as viewed from above.

First, the reflection member 142 having the structure shown in FIGS. 18A and 18B was verified for detection sensitivity to light generated from a sample when the storage position of the sample in the chamber 216 was varied. FIG. 18A shows the structure of the reflection member 142 and the vicinity thereof, in a perspective view from the side thereof. FIG. 18B shows the structure of the reflection member 142 as viewed from above. In FIGS. 18A and 18B, only a portion, around the hole 142b, of the reflection member 142 is shown.

In FIGS. 18A and 18B, D1 denotes the distance from a bottom face of the chamber 216 to the lower face of the cartridge 200. D2 denotes the distance from the lower face of the cartridge 200 to an upper face of the reflection member 142, that is, to the first opening 142c of the reflection member 142. D3 denotes the distance from the first opening 142c to the second opening 142d. φ1 denotes the diameter of the first opening 142c, and φ2 denotes the diameter of the second opening 142d. A gap having the distance D2 is for an ND filter to be inserted therein. In this verification, the ND filter is inserted/removed at the first opening 142c side opposed to the cartridge 200.

The first opening 142c is located at a position apart from a plane including the support face of the support member 177 supporting the cartridge 200. Thereby, a gap having the distance D2 is formed. Such a gap allows the cartridge 200 to rotate without contacting the reflection member 142.

As shown in FIGS. 18A and 18B, the reflection member 142 used in this verification has a structure in which the first opening 142c and the second opening 142d, both being round in shape, are connected by the conical inner face 142f. The first opening 142c and the second opening 142d are coaxially arranged. The inner face 142f has an axially symmetrical shape. There is no gap between the second opening 142d and the detection face S1 of the photodetector 144a.

This verification was performed with the design conditions below.

D1=1.89 mm
D2=0.7 mm
D3=15.2 mm
φ1=16.2 mm
φ2=9.0 mm

According to the above design conditions, the inclination angle of the inner face 142f with respect to the axis L0 connecting the center of the first opening 142c to the center of the second opening 142d is 13.3°.

The chamber 216 was round in shape in a plan view. The diameter of the chamber 216 was 9.3 mm. The cartridge 200 was placed so that the center of the chamber 216 was aligned with the axis L0.

A photo multiplier tube was used as the photodetector 144a. The detection face S1 of the photodetector 144a was round in shape in a plan view. The diameter of the detection face S1 was 8.0 mm. The photodetector 144a was disposed so that the center of the detection face S1 was aligned with the axis L0.

Figure 19A:
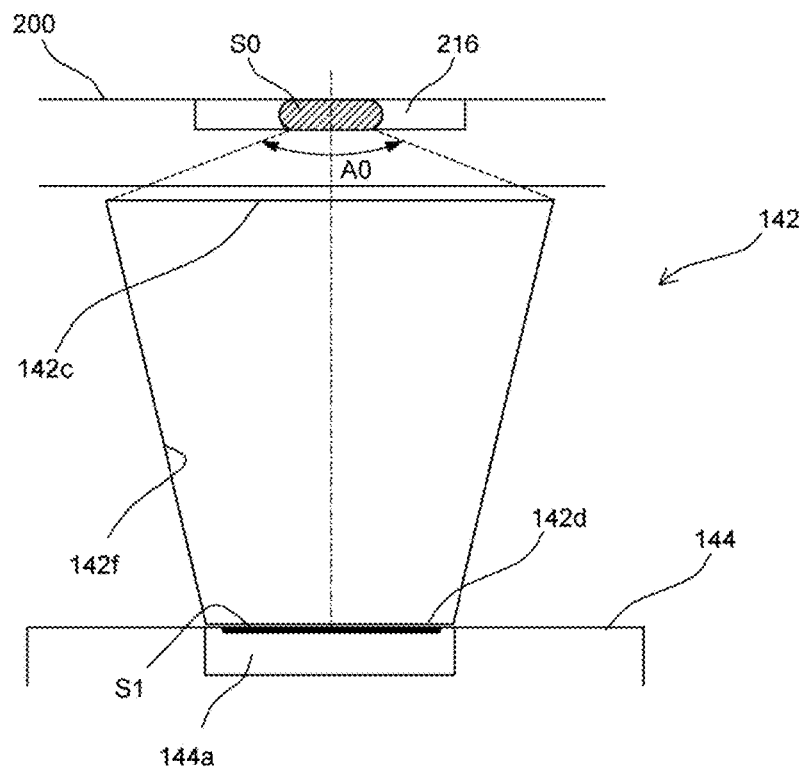
FIGS. 19A and 19B each show an effect of an inner face of the reflection member used for the verification according to Embodiment 1.
Figure 19B:
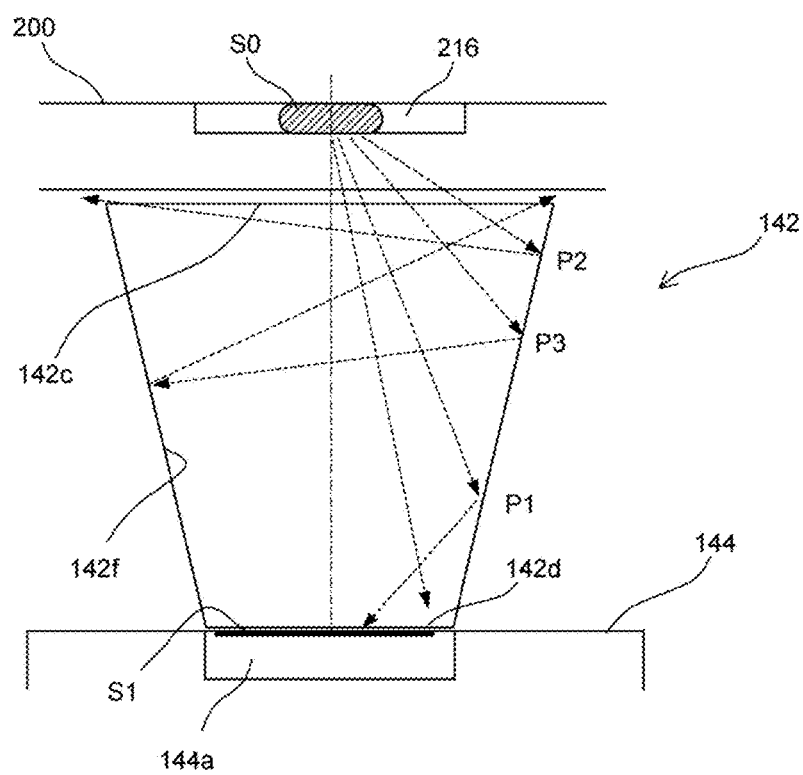

As shown in FIG. 19A, when a sample S0 containing a test substance is positioned at the center of the chamber 216, light within a range of a radiation angle A0 is taken into the reflection member 142. In this case, a part of the light having taken in reaches the detection face S1 directly or after being reflected at the inner face 142f, as shown in FIG. 19B. On the other hand, another part of the light having taken in is reflected at the inner face 142f once or a plurality of times, and thereby is directed to the first opening 142c before reaching the detection face S1 and is guided to the outside from the first opening 142c. For example, light reflected at a position P1 reaches the detection face S1, while lights reflected at positions P2 and P3 are guided to the outside from the first opening 142c without reaching the detection face S1.

Figure 20A:
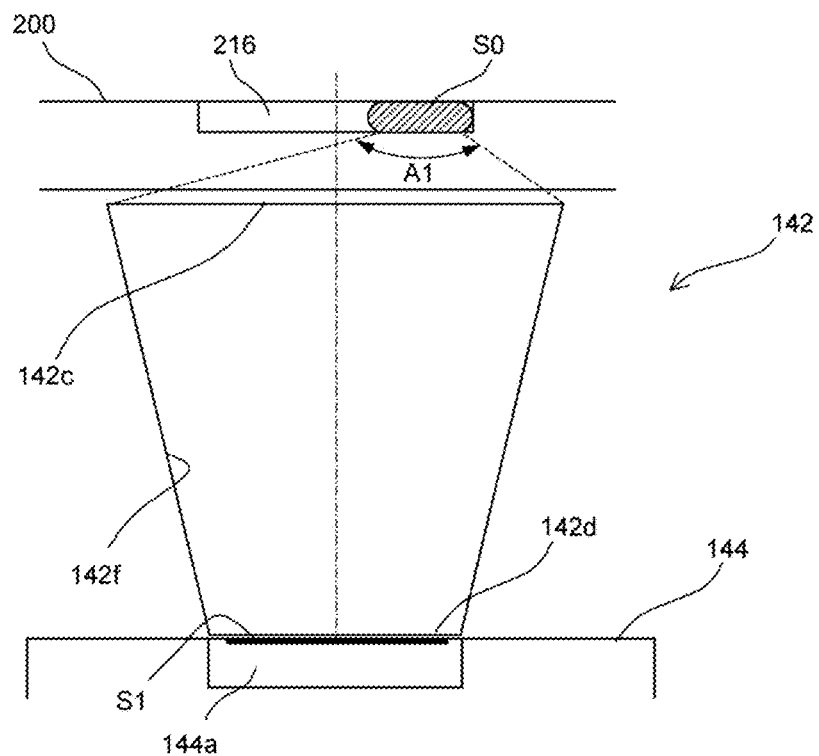
FIGS. 20A and 20B each show an effect of the inner face of the reflection member used for the verification according to Embodiment 1.

As shown in FIG. 20A, when the sample S0 containing the test substance is positioned at the edge of the chamber 216, light within a range of a radiation angle A1 is taken into the reflection member 142. The radiation angle A1 is smaller than the radiation angle A0 shown in FIG. 19A. Therefore, when the sample S0 is located at the edge of the chamber 216, the amount of light taken into the reflection member 142 is reduced, compared with that in the case where the sample S0 is positioned at the center of the chamber 216.

Figure 20B:
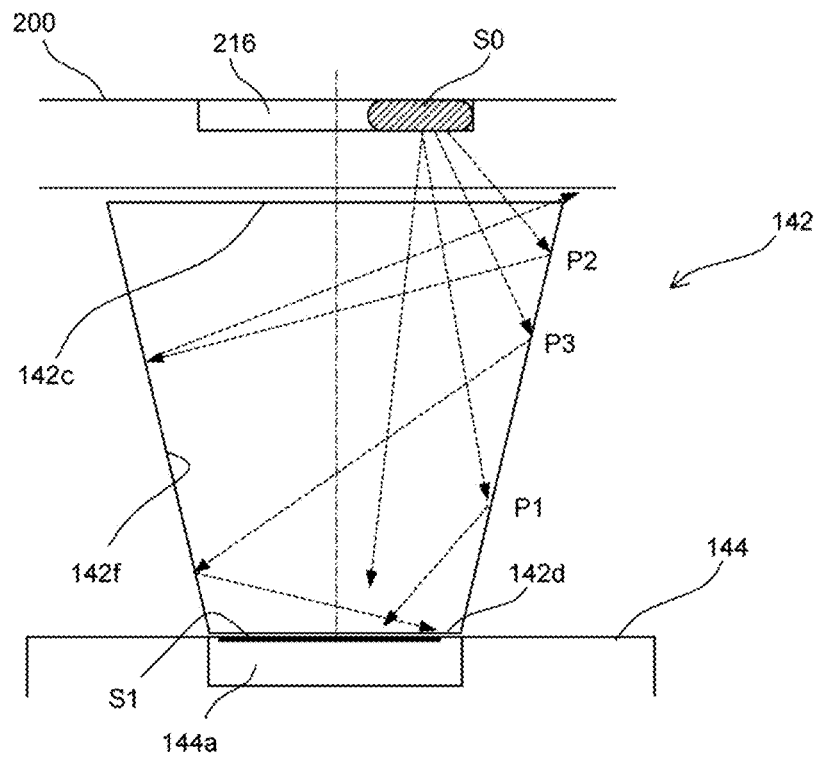

In this case, a part of the light having taken in reaches the detection face S1 directly or after being reflected at the inner face 142f, as shown in FIG. 20B. Meanwhile, another part of the light having taken in is reflected at the inner face 142f once or a plurality of times, and thereby is directed to the first opening 142c before reaching the detection face S1 and is guided to the outside from the first opening 142c.

In this case, light reflected at a position P1 reaches the detection face S1, as in the case of FIG. 19B. Meanwhile, light reflected at a position P2 is guided to the outside from the first opening 142c without reaching the detection face S1, as in the case of FIG. 19B. However, light reflected at a position P3 reaches the detection face S1, in contrast to the case of FIG. 19B. Thus, when the sample S0 is positioned at the edge of the chamber 216, the amount of light guided to the outside from the first opening 142c is reduced, although the amount of light taken into the reflection member 142 is reduced, compared with the case where the sample S0 is positioned at the center of the chamber 216. Thus, the difference in the amount of light reaching the detection face S1 is reduced between the case where the sample S0 is positioned at the center of the chamber 216 and the case where the sample S0 is positioned at the edge of the chamber 216.

The above design conditions are adjusted so that the amount of light reaching the detection face S1 is substantially the same regardless of where the sample is positioned in the chamber 216.

In this verification, after the chamber 216, the reflection member 142, and the detection face S1 were adjusted on the basis of the above design conditions, a chemiluminescence reaction with respect to the complex of the test substance was actually caused in the chamber 216, and the number of photons that reached the detection face S1 was measured on the basis of the output from the photodetector 144a.

Figure 21:
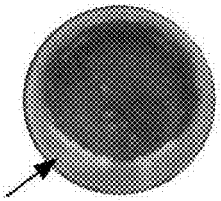
FIG. 21 shows results of the verification according to Embodiment 1.
Figure 21:
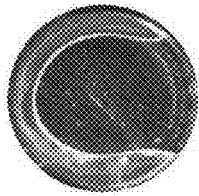
Figure 21:
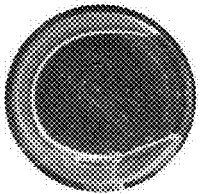
Figure 21:
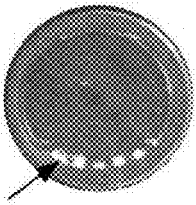
Figure 21:
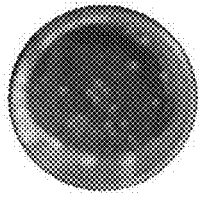
Figure 21:
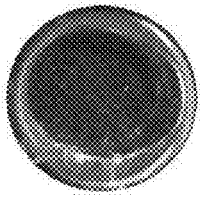
Figure 21:
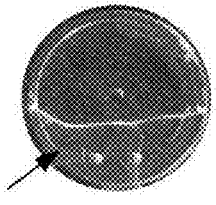
Figure 21:
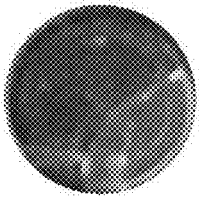
Figure 21:
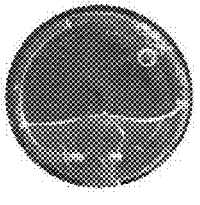
Figure 21:
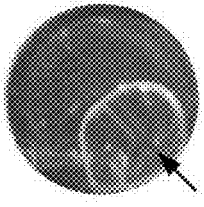
Figure 21:
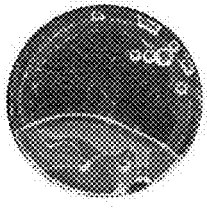
Figure 21:
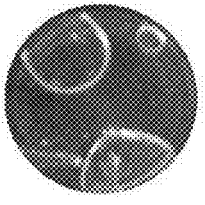

FIG. 21 shows the measurement results. The left column shows the measurement results in the case where no ND filter was inserted in the gap having the distance D2 shown in FIG. 18A. The center column and the right column show the measurement results in the case where an ND filter having transmission of 10% is inserted in the gap having the distance D2 shown in FIG. 18A, and the measurement results in the case where an ND filter having transmission of 1% is inserted in the gap, respectively.

Each of photographs in FIG. 21 shows an image of the state in the chamber 216 during measurement. The reagent in an amount less than the full capacity of the chamber 216 is stored in the chamber 216. Therefore, air is contained in the chamber 216. An arrow appended to each photograph in the left column indicates a region of air. A number appended to below each photograph indicates the number of photons counted within a predetermined time period on the basis of the output from the photodetector 144a. The measurement results included in the same column are obtained from the same sample.

As shown in FIG. 21, the measurement results in each column indicate substantially similar values regardless of the position of air, that is, the position of the sample in the chamber 216. It was confirmed from the measurement results that, even if the position of the sample in the chamber 216 varies and thereby the position of the light emitting region varies, the design conditions set as described above allow the amount of light incident on the photodetector 144a, that is, the number of photons, to be substantially uniform, and thereby allow detection sensitivity in the photodetector 144a to be substantially constant.

Next, it was verified how the measurement results vary between the case where measurement was performed using the reflection member 142 satisfying the above design conditions and the case where measurement was performed such that light generated from the chamber 216 was condensed onto the detection face S1 of the photodetector 144a by using a lens. In this verification, two types of cartridges 200, i.e., a cartridge 200 in which a chamber 216 having a diameter of 6 mm was formed and a cartridge 200 in which a chamber 216 having a diameter of 10 mm was formed, were used. The depths of the two types of chambers 216 were adjusted to store 50 µL of liquid. The effective diameter of the lens was 16.0 mm, and the distance between the bottom face of the chamber 216 and the lens was 14.73 mm.

Using each cartridge, for the same specimen, the complex containing the test substance was mixed with the reagent in each chamber to cause a chemiluminescence reaction. The amount of liquid stored in each chamber 216 was 50 µL. For light generated in each chamber 216, the number of photons received at the detection face S1 within a predetermined time period was counted, three times for each measurement system.

The measurement results are shown in Tables below.

TABLE 1

|  | With reflection member | |
| --- | --- | --- |
|  | Chamber A (φ = 6 mm) | Chamber B (φ = 10 mm) |
| 1st measurement | 974841 | 1033435 |
| 2nd measurement | 1027481 | 1011741 |
| 3rd measurement | 992578 | 992891 |
| Average | 998300 | 1012689 |
| Average ratio (A/B) |  | 101.4% |

TABLE 2

|  | With lens | |
| --- | --- | --- |
|  | Chamber A (φ = 6 mm) | Chamber B (φ = 10 mm) |
| 1st measurement | 22209 | 20622 |
| 2nd measurement | 22995 | 19383 |

TABLE 2-continued

|  | With lens | |
| --- | --- | --- |
|  | Chamber A (φ = 6 mm) | Chamber B (φ = 10 mm) |
| 3rd measurement | 24569 | 18501 |
| Average | 23258 | 19502 |
| Average ratio (A/B) |  | 83.9% |

When the lens is used, the measurement results vary depending on the diameter of the chamber 216, as shown in Table 2. Therefore, when the lens is used, detection sensitivity in the photodetector 144a may vary when the region of the sample is offset during measurement. In contrast, when the reflection member 142 is used, the measurement results are substantially the same even when the diameter of the chamber 216 varies, as shown in Table 1. Therefore, it is confirmed that, when the chamber 216 is used, detection sensitivity in the photodetector 144a can be kept substantially constant even when the region of the sample is offset during measurement.

Figure 22A:
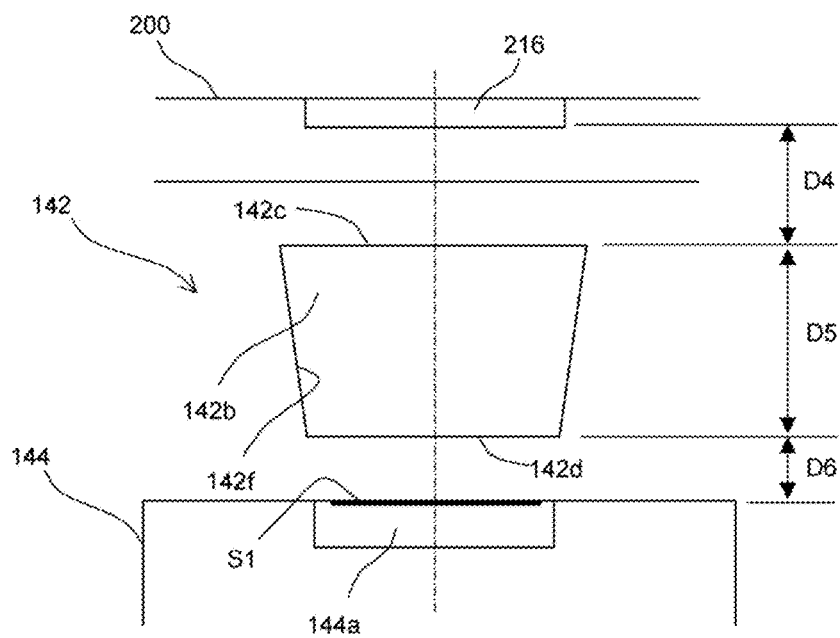
FIG. 22A shows a structure of a reflection member and the vicinity thereof in a perspective view from the side thereof, the reflection member being used for another verification according to Embodiment 1.

Next, the reflection member 142 having the structure shown in FIG. 22A was verified for detection sensitivity of light generated from the sample in the case where the chamber 216 was displaced from a predetermined detection position.

In FIG. 22A, D4 denotes the distance from the bottom face of the chamber 216 to the upper face of the reflection member 142, that is, to the first opening 142c of the reflection member 142. D5 denotes the distance from the first opening 142c to the second opening 142d. D6 denotes the distance between the second opening 142d and the detection face S1 of the photodetector 144a. A gap having the distance D6 is for an ND filter to be inserted therein. In this verification, it is assumed that an ND filter is inserted/removed at the second opening 142d side opposed to the photodetector 144a. The verification was performed without inserting an ND filter in the gap having the distance D6.

The reflection member 142 used in this verification has a structure in which the first opening 142c and the second opening 142d, both being round in shape, are connected by the conical inner face 142f, as in the above-described verification. The first opening 142c and the second opening 142d are coaxially arranged. The inner face 142f has an axially symmetrical shape.

This verification was performed with the design conditions below.

D4=4.5 mm
D5=7.5 mm
D6=2.8 mm
φ1=11.86 mm
φ2=9.84 mm

φ1 denotes the diameter of the first opening 142c, and φ2 denotes the diameter of the second opening 142d. According to the above design conditions, an inclination angle of the inner face 142f with respect to the axis L0 connecting the center of the first opening 142c to the center of the second opening 142d is 7.74°.

The chamber 216 was round in shape in a plan view. The diameter of the chamber 216 was 7.6 mm. The cartridge 200 was placed so that the center of the chamber 216 was aligned with the axis L0.

A photo multiplier tube was used as the photodetector 144a. The detection face S1 of the photodetector 144a was round in shape in a plan view. The diameter of the detection face S1 was 8.0 mm. The photodetector 144a was disposed so that the center of the detection face S1 is aligned with the axis L0.

Figure 22B:
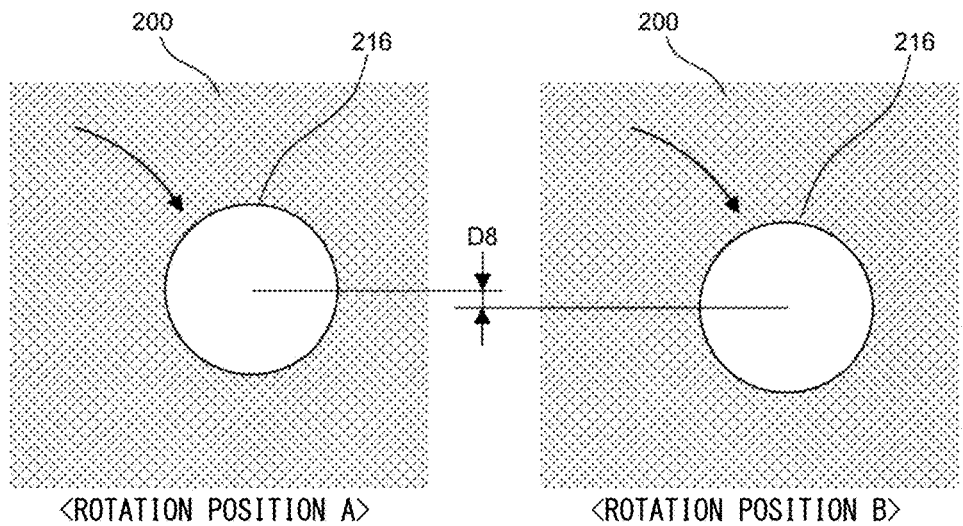
FIG. 22B is a schematic diagram showing the state of displacement of a chamber in the other verification according to Embodiment 1.

In this verification, the cartridge 200 was rotated to locate the chamber 216 at the detection position opposed to the photodetector 144a. As schematically shown in FIG. 22B, due to a braking error of the motor 171, a gap having a distance D8 was generated between stop positions of the chamber 216. The distance D8 was 1.02 mm. For the chamber 216 positioned at each of rotation positions A and B, the number of photons received at the light detection face S1 within a predetermined time period was counted, twice for each chamber position. The measurement results are shown in Table below.

TABLE 3

|  | Rotation position A | Rotation position B |
|---|---|---|
| 1st measurement | 1021998 | 1031518 |
| 2nd measurement | 1027607 | 1048389 |
| Average | 1024802 | 1039954 |
| Average ratio (A/B) |  | 101.5% |

As shown in Table 3, the measurement results are substantially similar values regardless of the rotation position. It was confirmed from the measurement results that, even if the position of the chamber 216 varies due to the braking error of the motor 171, the design conditions set as described above allow the amount of light incident on the photodetector 144a, that is, the number of photons, to be substantially uniform, and thereby allow detection sensitivity in the photodetector 144a to be substantially constant.

Through the above verifications, it was confirmed that, according to the structure of Embodiment 1, even when the light emitting region in the chamber 216, which is based on the complex containing the test substance, was displaced from the detection position opposed to the detection face S1 of the photodetector 144a, detection sensitivity as high as that in the case where the light emitting region was positioned at the detection position was achieved by adjusting the inclination of the inner face 142f.

In Embodiment 1, by the rotation mechanism including the motor 171 and the support member 177, the cartridge 200 is rotated, and thereby the chamber 216 is located at the detection position opposed to the first opening 142c. Therefore, the chamber 216 could be displaced from the detection position due to, for example, a braking error of the motor 171. As shown by the verification results on Table 3, it was confirmed that, even when the chamber 216 was displaced from the detection position due to, for example, a braking error of the motor 171, detection sensitivity as high as that in the case where the light emitting region was located at the detection position was achieved.

In Embodiment 1, the sample in an amount less than the full capacity of the chamber 216 is stored in the chamber 216, and a chemiluminescence reaction occurs between the luminescent substrate and the labeling substance that binds to the test substance. Since the liquid amount of the sample stored in the chamber 216 is small, the sample storage region, i.e., the light emitting region, in the chamber 216 can vary as shown in FIG. 21. In particular, in Embodiment 1, the process of agitating the sample in the chamber 216 by rotating the cartridge 200 is performed before measurement. Therefore, the sample storage region, i.e., the light emitting region, in the chamber 216 is likely to vary randomly. From the verification results shown in FIG. 21, it was confirmed that, according to the structure of Embodiment 1, even when the sample storage region, i.e., the light emitting region, in the chamber 216 was located at various positions as described above, substantially similar detection sensitivity was achieved.

In Embodiment 1, both the first opening 142c and the second opening 142d have round shapes, and the inner face 142f has an axially symmetrical conical shape. Therefore, even when the sample, i.e., the light emitting region, is displaced in any direction with respect to the center axis of the first opening 142c, similar optical effect is applied by the reflection member 142 to the light generated from the light emitting region. Therefore, substantially similar detection sensitivity can be achieved regardless of the direction of the displacement.

As shown in the respective verifications described above, the first opening 142c has the size including the chamber 216 located at the detection position as viewed from the photodetector 144a side. Therefore, more of the light generated in the chamber 216 can be taken into the reflection member 142, whereby output power of the photodetector 144a can be increased.

Next, design conditions were examined which allow detection sensitivity to be kept substantially constant regardless of the position of the sample.

Also in this examination, it is assumed that the reflection member 142 has a structure in which the first opening 142c and the second opening 142d, both being round in shape, are connected by the conical inner face 142f. In addition, the first opening 142c and the second opening 142d are coaxially arranged. The inner face 142f has an axially symmetrical shape.

Figure 23A:
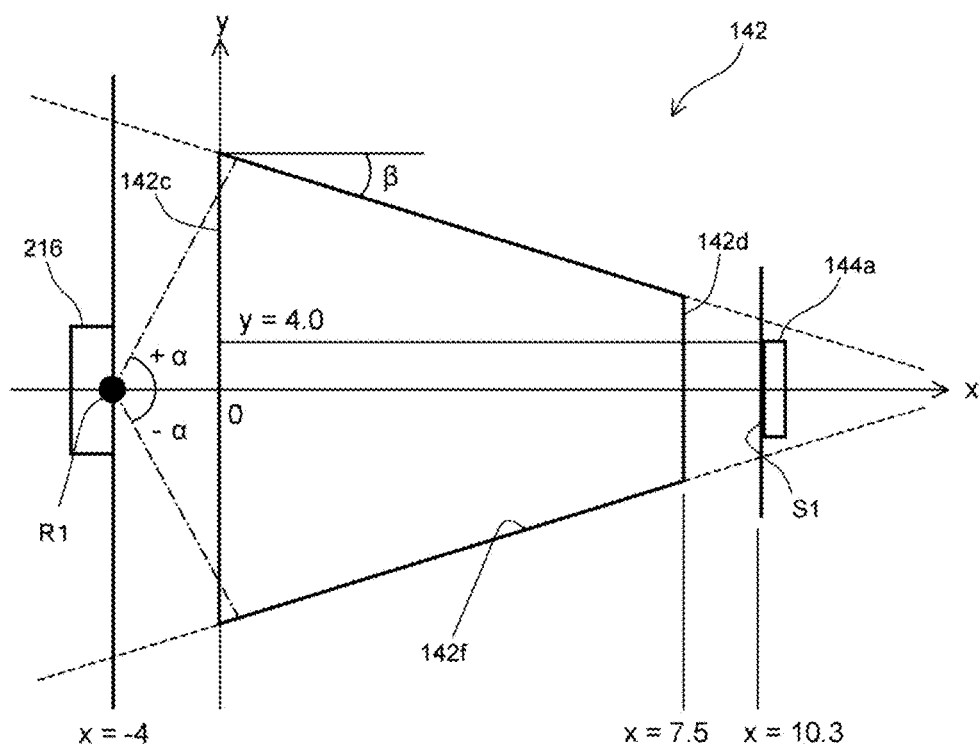
FIG. 23A shows design conditions of components near the reflection member in a simulation for the inclination angle of the inner face, according to Embodiment 1.

As shown in FIG. 23A, an x axis and a y axis were set, and the amount of light received at the detection face S1, with respect to light within a range of a radiation angle $\pm\alpha°$ which was generated from a light emitting point R1, was obtained by simulation. In the simulation, at a position of $x=-4$, the light emitting point R1 was offset in a y-axis positive direction from the original position, and the amount of light received at the detection face S1, in each offset position, was obtained by two-dimensional analysis. The maximum offset amount of the light emitting point R1 in the Y-axis positive direction was 5 mm.

Figure 23B:
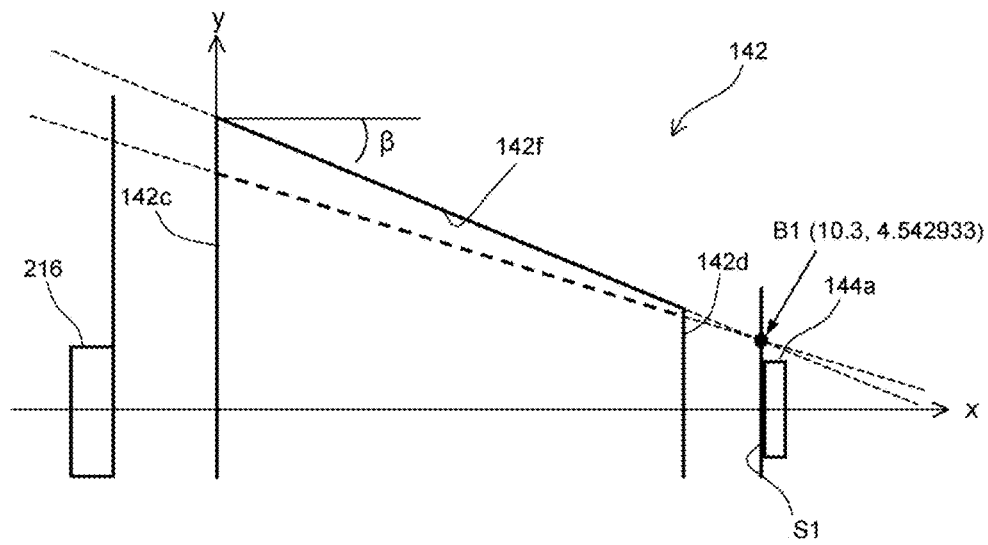
FIG. 23B shows an inclination angle setting method in the simulation for the inclination angle of the inner face, according to Embodiment 1.

Further, an inclination angle $\beta$ of the inner face 142f was varied to locate the light emitting point R1 at different offset positions, and the amount of light received at the detection face S1, of the light within the range of a radiation angle $\pm\alpha°$, in each offset position, was obtained by two-dimensional analysis. As shown in FIG. 23B, the inclination angle $\beta$ was varied by pivoting the inner face 142f at the position of a fulcrum B1. Therefore, the diameters of the first opening 142c and the second opening 142d also varied with the variation in the inclination angle. The fulcrum B1 was set to a coordinate position (10.3, 4.52933) on the y-axis positive side of the detection face S1.

In this verification, $\alpha$ was 89.5°. The diameter of the detection face S1 was 8 mm as in the above verification. A gap for an ND filter to be inserted/removed thereinto/therefrom was provided between the detection face S1 and the second opening 142d. Therefore, a part of light having advanced throughout the inner face 142f is guided to the outside through the gap between the detection face S1 and the second opening 142d, without reaching the detection face S1. Taking this into account, the amount of light received at the detection face S1 was obtained in the simulation.

FIG. 24A to FIG. 25B show the measurement results. In each figure, the horizontal axis indicates the y coordinate of the light emitting point R1, and the vertical axis indicates the amount of received light. The vertical axis indicates the amount of received light in an arbitrary unit. In each figure, the simulation results of the amount of received light are graphed with respect to the respective inclination angles β of the inner face 142f.

Figure 24A:
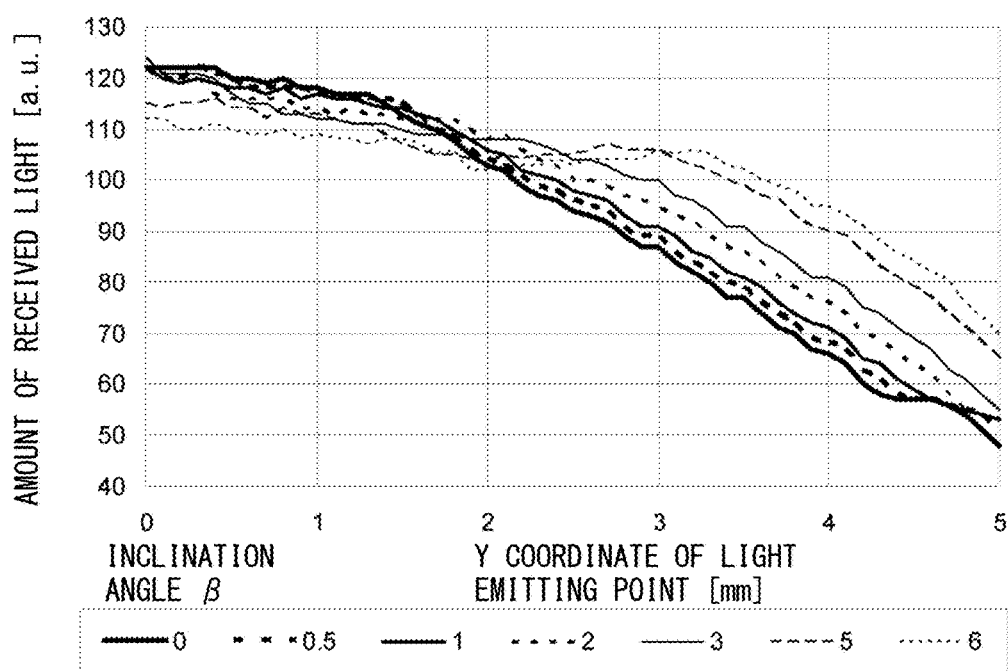
FIGS. 24A and 24B each show results of a simulation for obtaining the relationship between the position of a light emitting point and the amount of received light, with the inclination angle of the inner face being varied, according to Embodiment 1.
Figure 24B:
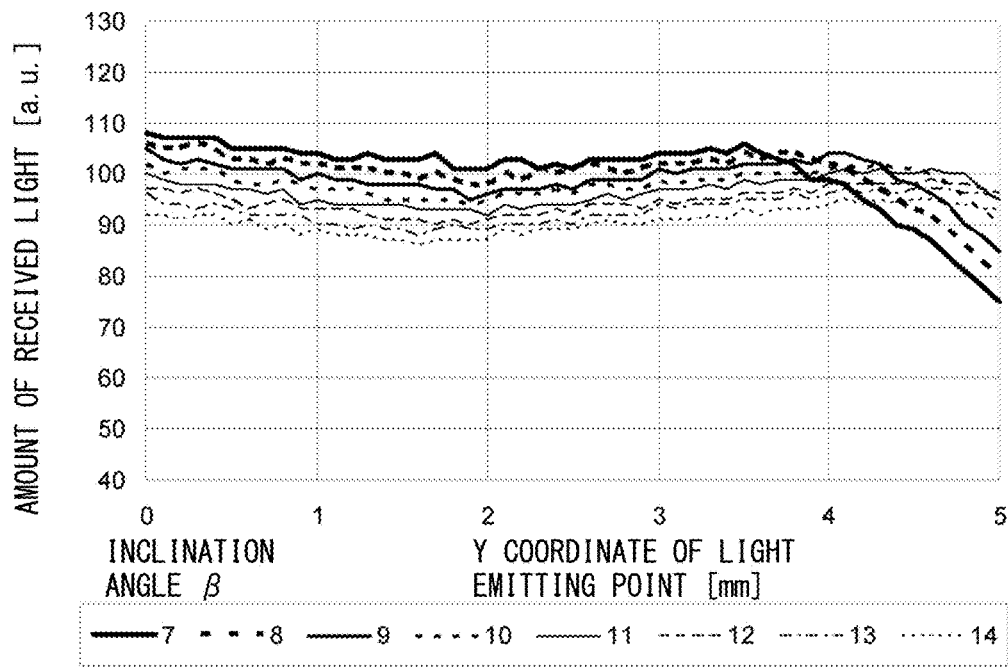
Figure 25A:
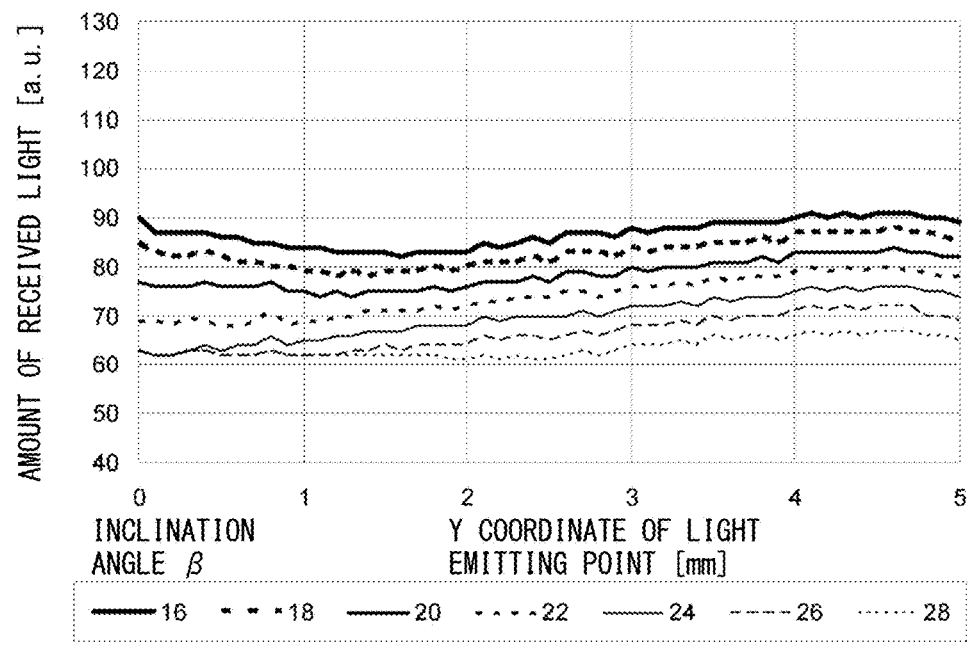
FIGS. 25A and 25B each show results of a simulation for obtaining the relationship between the position of the light emitting point and the amount of received light, with the inclination angle of the inner face being varied, according to Embodiment 1.
Figure 25B:
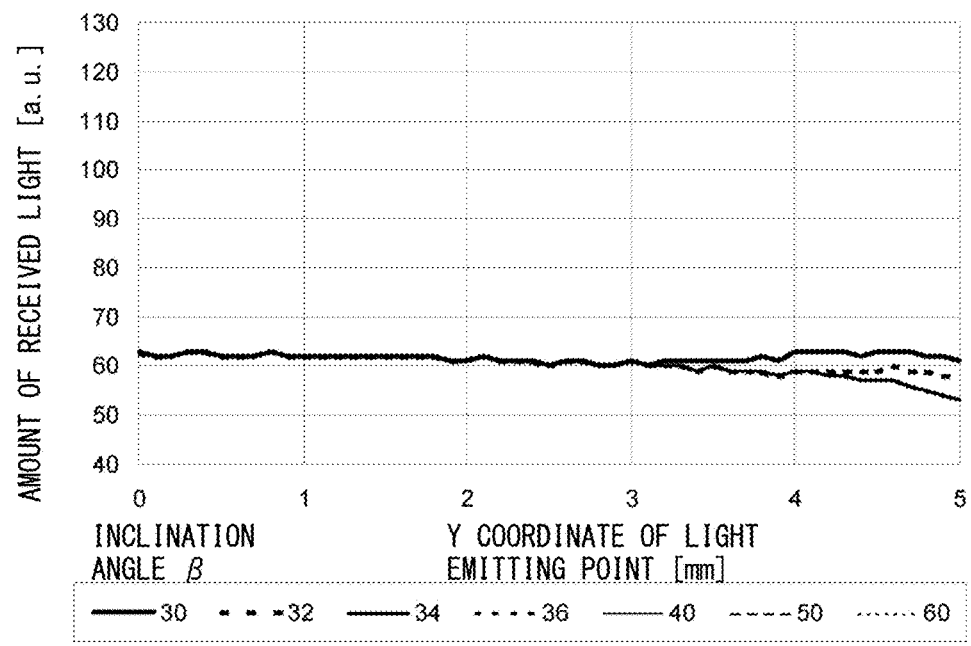

As shown in FIG. 24A, in the case where the inclination angle β is 0° to 3°, the amount of received light when the offset amount of the light emitting point R1 is 0 is high, but the amount of received light decreases in accordance with offset of the light emitting point R1. In the case where the inclination angle β is 5° and 6°, the amount of received light is kept substantially constant until the offset amount of the light emitting point R1 exceeds about 3 mm. As shown in FIG. 24B, in the case where the inclination angle β is 7° to 14°, although the amount of received light when the offset amount of the light emitting point R1 is 0 is slightly lowered, the amount of received light is kept substantially constant even when the light emitting point R1 is displaced within a range of about 4 mm from an original point thereof. As shown in FIG. 25A, in the case where the inclination angle β is 16° to 28°, although the amount of received light is kept substantially constant even when the light emitting point R1 is displaced from the original point, the amount of received light when the offset amount of the light emitting point R1 is 0 decreases with increase in the inclination angle β. As shown in FIG. 25B, in the case where the inclination angle β is 30° to 60°, the amount of received light when the offset amount of the light emitting point R1 is 0 is further lowered. In FIG. 25B, since the measurement results corresponding to a plurality of inclination angles overlap each other, only the measurement results corresponding to three inclination angles can be seen.

Figure 26A:
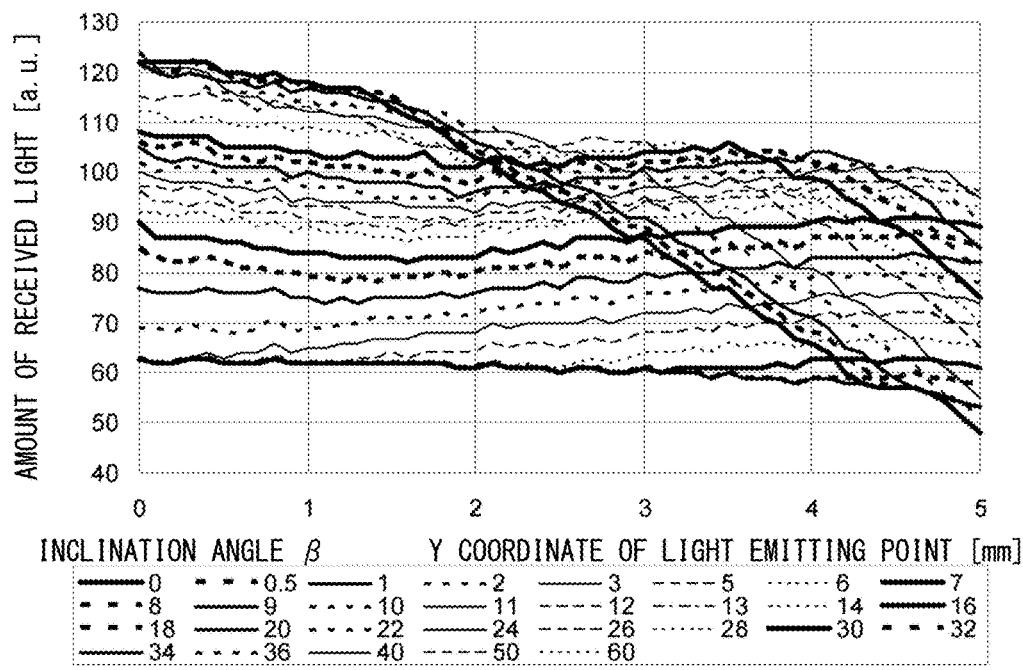
FIG. 26A shows results of a simulation for obtaining the relationship between the position of the light emitting point and the amount of received light, with the inclination angle of the inner face being varied, according to Embodiment 1.
Figure 26B:
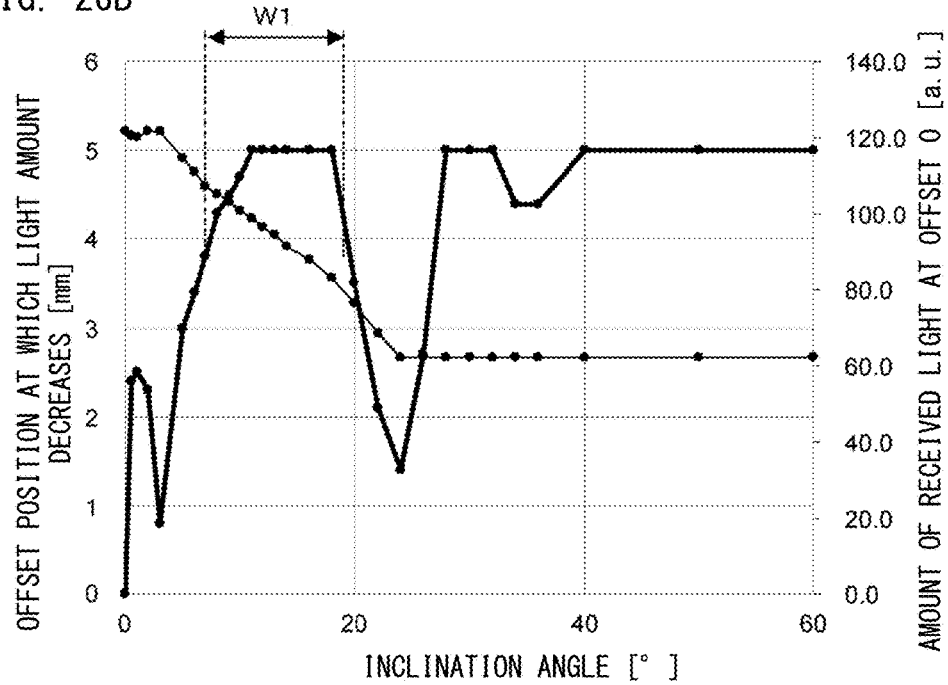
FIG. 26B shows simulation results combining: the offset position of the light emitting point at which the amount of received light varies; and the amount of received light when the light emitting point is not offset, in the case where the inclination angle of the inner face is varied, according to Embodiment 1.

FIG. 26A shows all the graphs of the inclination angles being integrated. FIG. 26B shows a graph representing, for each inclination angle, the amount of received light when the offset amount of the light emitting point R1 with respect to the original point is 0, and a graph representing, for each inclination angle, the offset position of the light emitting point R1 in the y-axis positive direction with respect to the original point, at which the amount of received light starts to decrease.

In FIG. 26B, the horizontal axis indicates the inclination angle of the inner face 142f, the right-side vertical axis indicates the amount of received light when the offset amount of the light emitting point R1 with respect to the original point is 0, and the left-side vertical axis indicates the offset position of the light emitting point R1 in the y-axis positive direction with respect to the original point, at which the amount of received light starts to decrease. A thick-line graph represents the offset position of the light emitting point R1 in the y-axis positive direction with respect to the original point, at which the amount of received light starts to decrease. A thin-line graph represents the amount of received light when the offset amount of the light emitting point R1 with respect to the original point is 0. Since the maximum offset amount of the light emitting point R1 is 5 mm, the maximum value of the thick-line graph is saturated at 5 mm.

In the case where the round chamber 216 disposed in the cartridge 200 has a diameter of 8 mm, the sample storage position in the chamber 216 can be offset by 4 mm at maximum from the center of the chamber 216. Therefore, when measurement is performed using the cartridge 200 having such a chamber 216, it is preferable to set the inclination angle of the inner face 142f so that the amount of light received by the photodetector 144a is substantially constant and is kept high, with the offset amount of the light emitting point R1 with respect to the original point being within a range of 4 mm.

According to the verification results shown in FIG. 26B, when the inclination angle is within a range of W1, the amount of received light is substantially constant and is kept at a high level not lower than 80 a.u., with the offset amount of the light emitting point R1 with respect to the original point being within a range of about 4 mm. Therefore, according to the verification results, it can be said that the inclination angle β of the inner face 142f is set to preferably about 5° to 20°, and more preferably about 7° to 18°.

When the inclination angle β of the inner face 142f is set as described above, as seen from FIGS. 24A and 24B, the amount of light received by the detection face S1 when the light emitting point R1 is located at a position at the edge of the chamber 216, that is, a position 4 mm offset from the original point, is maintained at 90% to 100% of the amount of light received by the detection face S1 when the light emitting point R1 is located at the center of the chamber 216, that is, at the position of the original point. Therefore, when the inclination angle β of the inner face 142f is set as described above, the amount of light received by the detection face S1 when the light emitting region based on the complex is located at a position displaced toward the edge of the first opening 142c, is maintained at about 90% to 110% of the amount of light received by the detection face S1 when the light emitting region based on the complex is located at the center of the first opening 142c. Accordingly, variation in the amount of detected light due to displacement of the light emitting region can be inhibited, whereby accuracy of analyzing the test substance can be enhanced.

Further, in the case where the inclination angle β of the inner face 142f is 5° to 20° or 7° to 18° as described above, the diameter of the first opening 142c is 10.9 to 16.6 mm or 11.6 to 15.8 mm, and the diameter of the second opening 142d is 9.6 to 11.1 mm or 9.8 to 9.9 mm, according to the inclination angle β setting method shown in FIG. 23B. In this case, the diameter of the second opening 142d is 67% to 88% or 63% to 85% of the diameter of the first opening 142c. Therefore, in order to make the amount of received light substantially constant and keep the amount of received light at a high level even when the position of the light emitting point R1 is displaced, it is preferable that the diameter of the first opening 142c is 10.9 to 16.6 mm and the ratio of the second opening 142d to the first opening 142c is 67% to 88%, and it is more preferable that the diameter of the first opening 142c is 11.6 to 15.8 mm, and the ratio of the second opening 142d to the first opening 142c is 63% to 85%.

Next, variation in the amount of light received by the photodetector 144a when the light emitting point R1 was shifted in a direction away from the first opening 142c, was examined. The design conditions were the same as those of the simulations shown in FIG. 23A to FIG. 26B. The respective values shown in FIG. 26B were obtained by simulation, with the shift amount of the light emitting point R1 in the x-axis negative direction with respect to the first opening 142c being varied in the design conditions shown in FIG. 23A.

FIG. 27A to FIG. 28C show the simulation results.

Figure 27A:
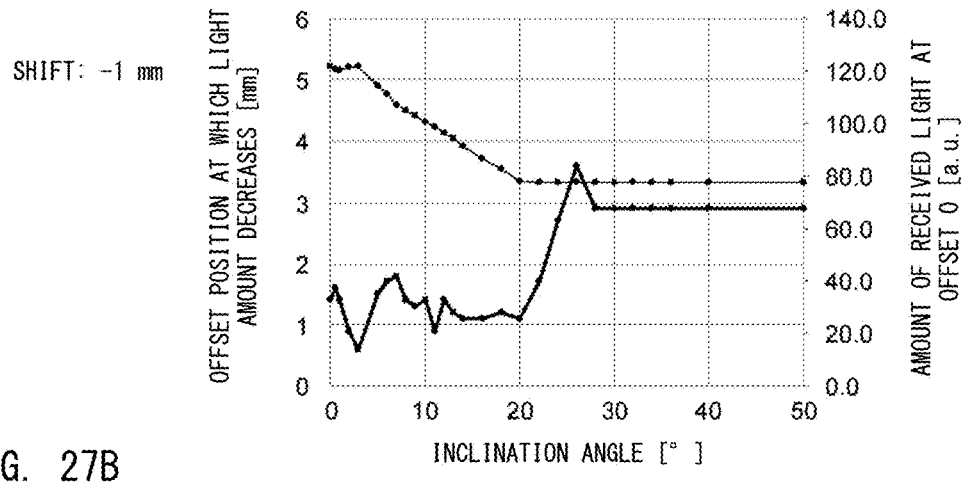
FIGS. 27A to 27C each show, for each shift amount of the light emitting point with respect to a first opening, simulation results combining: the offset position of the light emitting point at which the amount of received light varies; and the amount of received light when the light emitting point is not offset, in the case where the inclination angle of the inner face is varied, according to Embodiment 1.
Figure 27B:
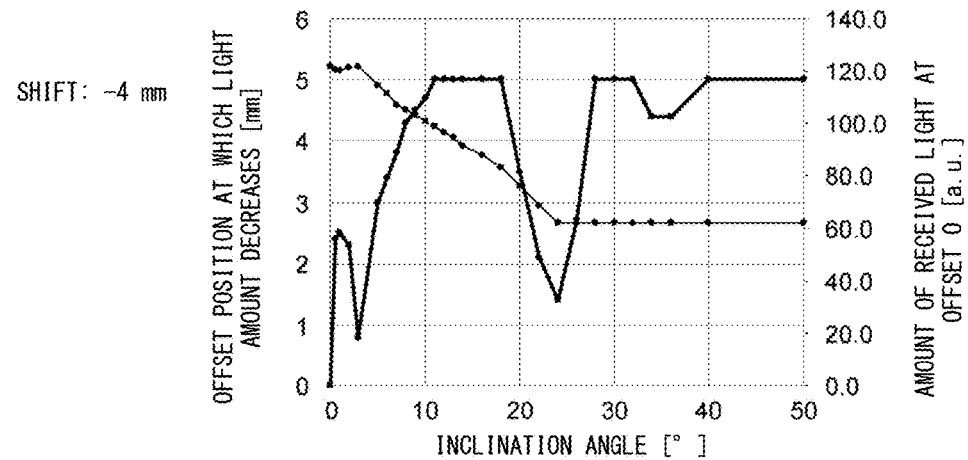
Figure 27C:
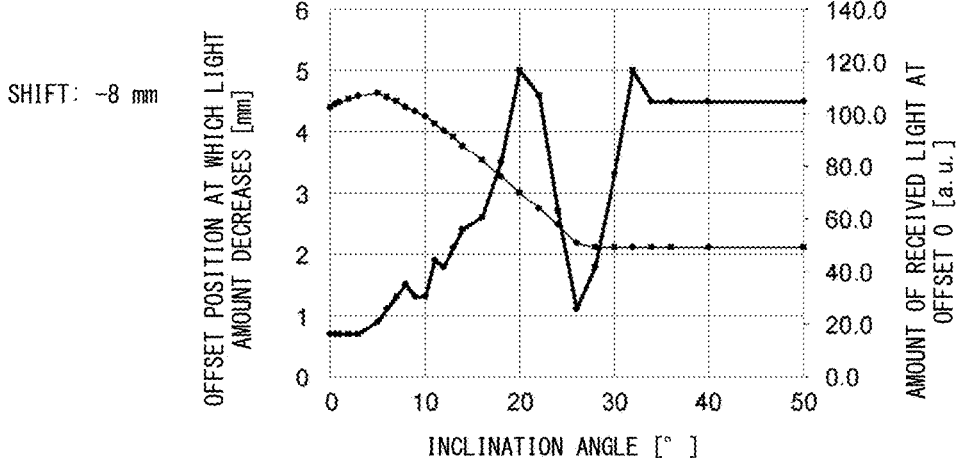
Figure 28A:
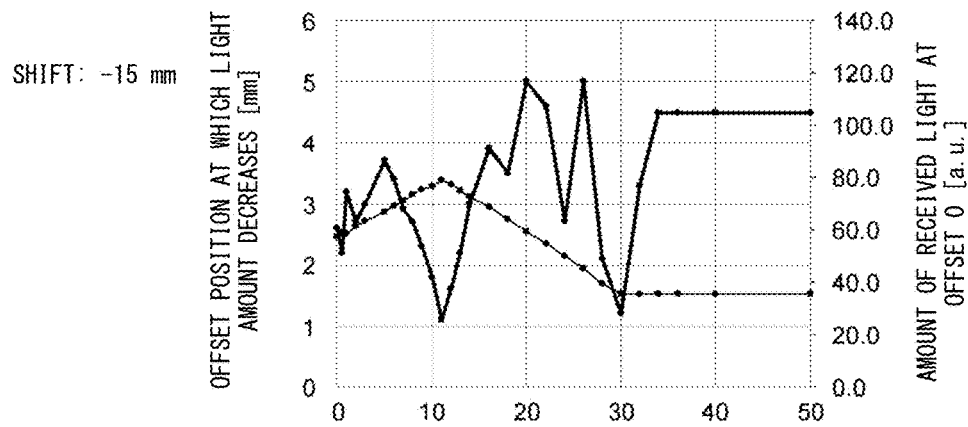
FIGS. 28A to 28C each show, for each shift amount of the light emitting point with respect to the first opening, simulation results combining: the offset position of the light emitting point at which the amount of received light varies; and the amount of received light when the light emitting point is not offset, in the case where the inclination angle of the inner face is varied, according to Embodiment 1.
Figure 28B:
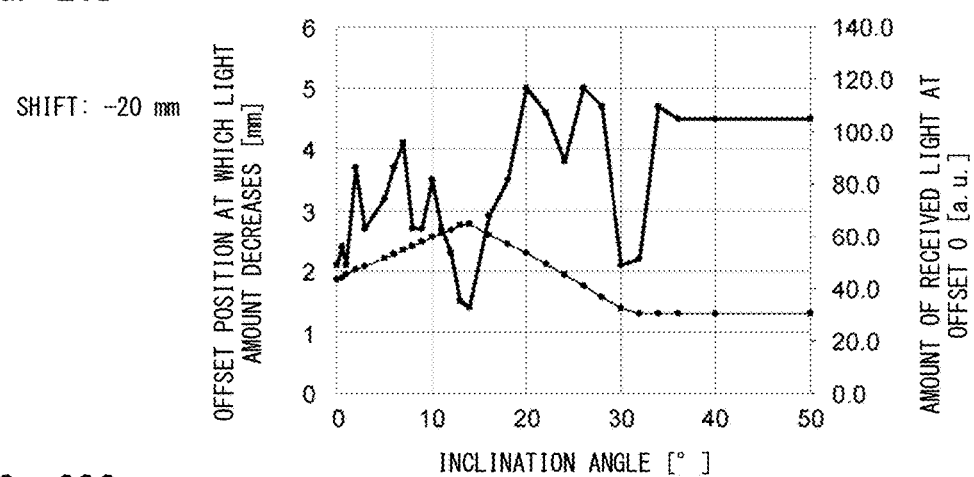
Figure 28C:
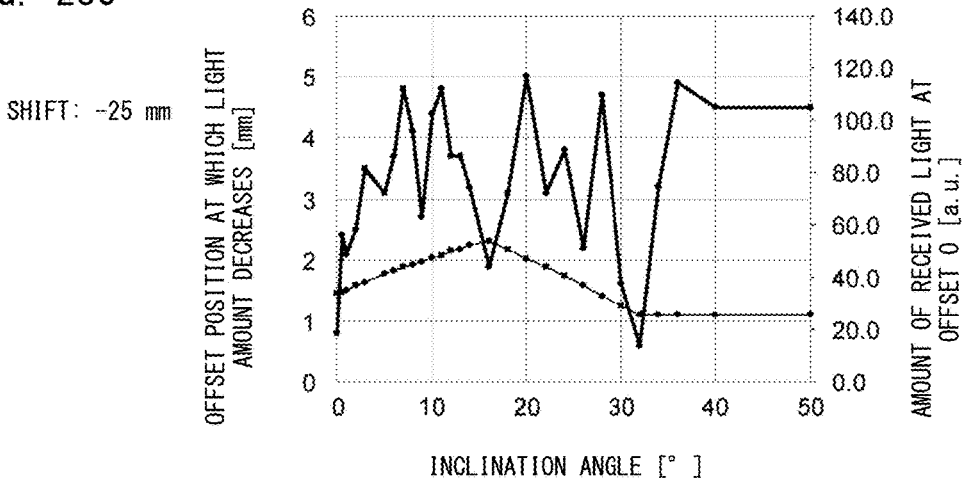

FIGS. 27A to 27C show the simulation results in the case where the shift amount is −1 mm, −4 mm, and −8 mm, respectively. FIGS. 28A to 28C show the simulation results in the case where the shift amount is −15 mm, −20 mm, and −25 mm, respectively.

With reference to FIG. 28C, the position of the light emitting point, at which the amount of received light decreases, significantly varies in accordance with variation in the inclination angle β of the inner face 142f. Accordingly, it is considered that, when the shift amount of the light emitting point with respect to the first opening 142c is −25 mm, the optical effect of the inner face 142f significantly changes even with a slight change of the inclination angle β, which makes light-receiving sensitivity in the photodetector 144a unstable.

With reference to FIG. 27A to FIG. 28B, when the shift amount of the light emitting point with respect to the first opening 142c is −1 mm, −4 mm, −8 mm, −15 mm, and −20 mm, even if the inclination angle β of the inner face 142f varies, the position of the light emitting point, at which the amount of received light decreases, does not vary greatly and is relatively stable. Therefore, it is considered that, when the shift amount of the light emitting point is −1 mm, −4 mm, −8 mm, −15 mm, and −20 mm, even if the inclination angle β slightly varies from the set value, the optical effect of the inner face 142f does not substantially change, whereby light-receiving sensitivity in the photodetector 144a can be stabilized. When the shift amount of the light emitting point is −1 mm, −4 mm, −8 mm, −15 mm, and −20 mm, it is also possible to ensure a relatively high amount of received light.

Thus, the shift amount of the light emitting point R1 with respect to the first opening 142c is preferably within a range of 1 to 20 mm. Accordingly, the distance between the bottom face of the chamber 216 and the first opening 142c is preferably within a range of 1 to 20 mm.

Embodiment 2

Figure 29A:
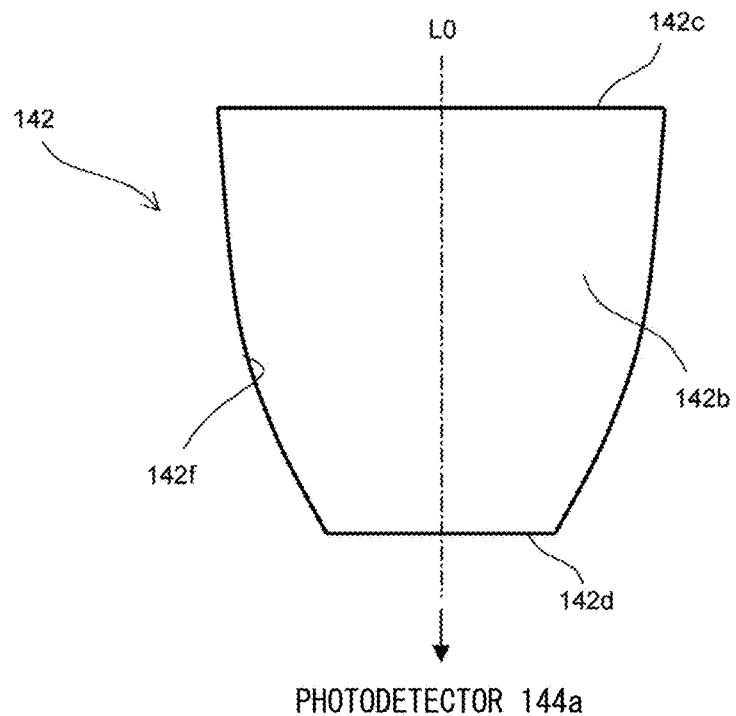
FIGS. 29A and 29B are each a schematic diagram showing a structure of a reflection member according to Embodiment 2.
Figure 29B:
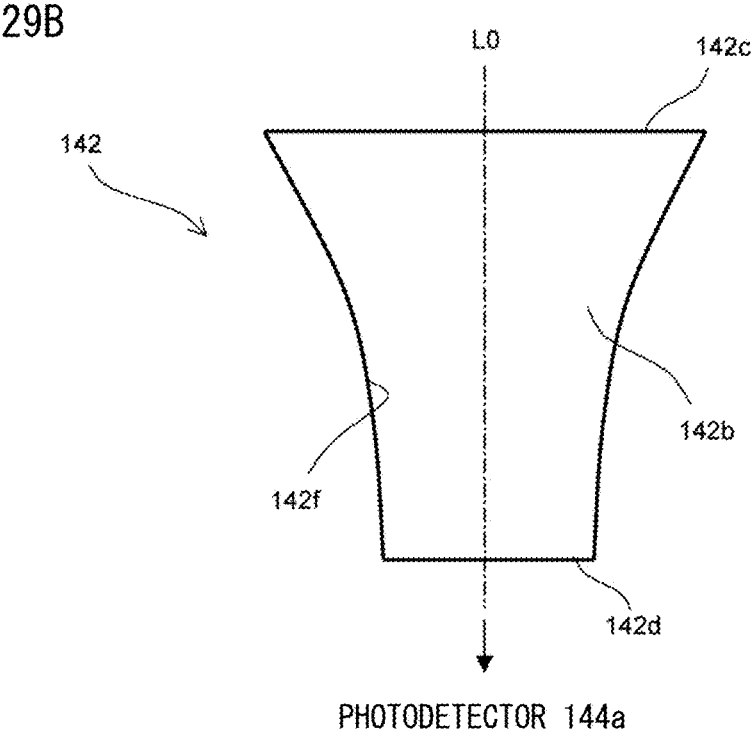

In Embodiment 2, the shape of the inner face 142f of the reflection member 142 is different from that of Embodiment 1. In Embodiment 2, as shown in FIG. 29A, the shape of the inner face 142f includes curved portions that protrude to opposite sides from the axis L0, at a cross-section taken along the axis L0 connecting the center of the first opening 142c and the center of the second opening 142d. Alternatively, as shown in FIG. 29B, the shape of the inner face 142f may include curved portions that protrude toward the axis L0, at the cross-section taken along the axis L0 connecting the center of the first opening 142c and the center of the second opening 142d.

By designing the inner face 142f to be inclined in a curved shape as described above, the amount of light, of the light taken in from the first opening 142c, which is reflected at the inner face 142f and guided to the outside from the first opening 142c, can be adjusted more precisely. Therefore, it can be supposed that it is possible to inhibit, more reliably, variation in the amount of received light in the case where the light emitting region of the chamber 216, based on the complex containing the test substance, is displaced in a direction parallel to the detection face S1 of the photodetector 144a from the detection position opposed to the detection face S1. Further, it can be supposed that the amount of light guided to the detection face S1 of the photodetector 144a can be increased.

On the other hand, in Embodiment 2, processing of the inner face 142f is complicated. Therefore, in order to effectively inhibit variation in the amount of received light, which is based on displacement of the light emitting region, by simple processing, the structure of Embodiment 1 is preferred in which the inner face 142f of the reflection member 142 is formed linearly at a cross-section taken along the axis L0 connecting the center of the first opening 142c and the center of the second opening 142d.

Embodiment 3

Figure 30A:
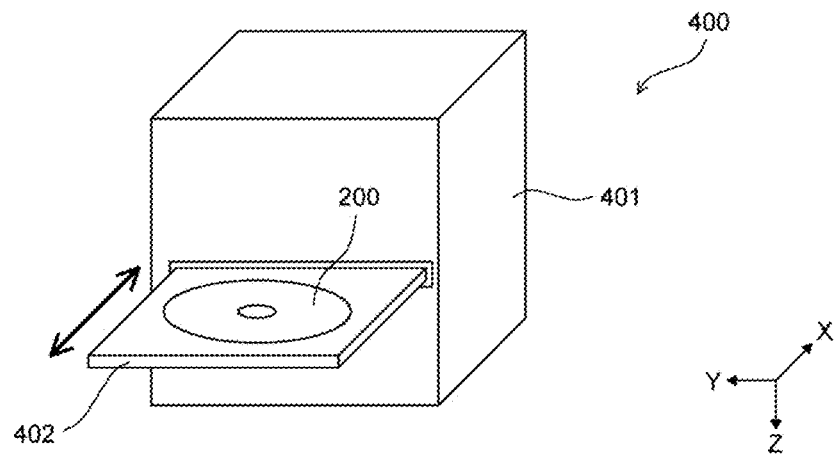
FIG. 30A is a schematic diagram showing an external structure of an analyzer according to Embodiment 3.

In Embodiment 1, as already described with reference to FIG. 2A, the cartridge 200 is mounted to the analyzer 100, with the lid 102 being opened. In Embodiment 3, as shown in FIG. 30A, the cartridge 200 is placed on a tray 402 that is moved outward via a hole provided on a side face of a casing 401, and mounting of the cartridge 200 to an analyzer 400 is performed when the tray 402 is moved inward.

The tray 402 supports only an outer edge of the cartridge 200. After the tray 402 is drawn into the casing 401, the tray 402 is moved to the Z-axis negative side. Thereby, the cartridge 200 is placed on the support member 177. In order to cause the inside of the casing 401 to be a dark space, a structure for closing, from the inside of the casing, the hole for inserting/ejecting the tray 402 provided at the front face of the casing 401, is separately provided. Other components are the same as the specific examples of components of Embodiment 1.

Embodiment 4

Figure 30B:
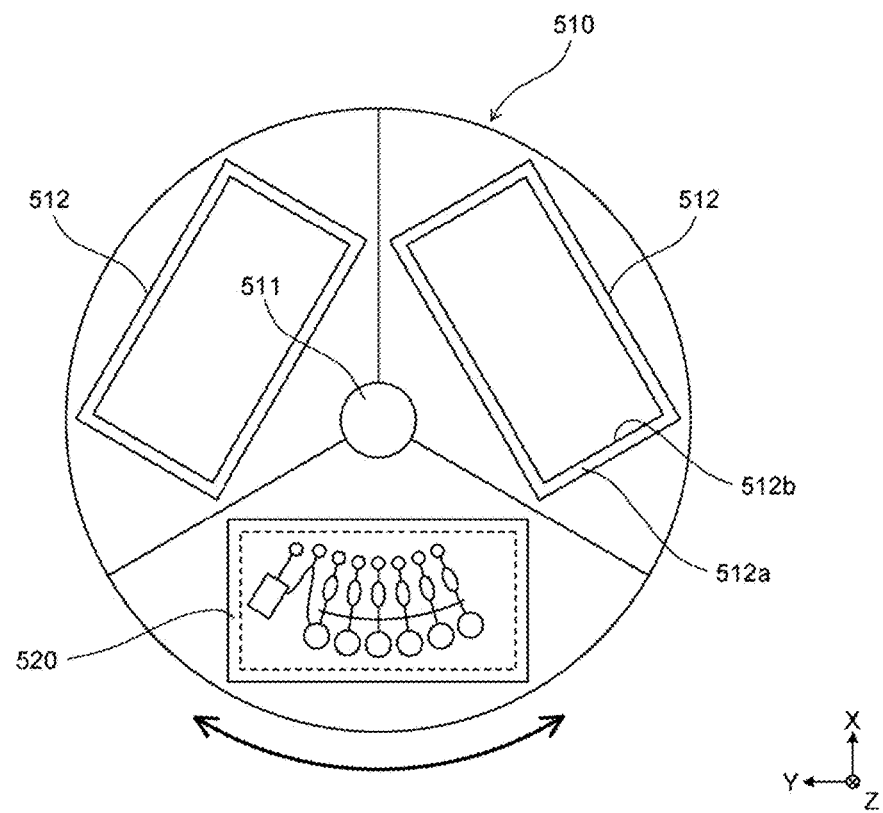
FIG. 30B schematically shows structures of a support member and a cartridge according to Embodiment 4 as viewed from above.

In Embodiment 4, as shown in FIG. 30B, a support member 510 is provided instead of the support member 177, and a cartridge 520 is used instead of the cartridge 200. Other components are the same as the specific examples of components of Embodiment 1.

The support member 510 includes a hole 511, and three mounting portions 512. The hole 511 is provided at the center of the support member 510. The support member 510 is mounted on the rotation shaft 311 via a predetermined member. Thereby, the support member 510 is rotatable around the rotation shaft 311. The three mounting portions 512 are provided in the circumferential direction. Each mounting portion 512 has a face 512a and a hole 512b. The face 512a is one step lower than an upper face of the support member 510. The hole 512b is formed at the center of the face 512a, and penetrates the support member 510 in the vertical direction. The cartridge 520 has a rectangular shape, and a structure similar to that of the cartridge 200.

When analysis is started, an operator infuses a blood specimen into the cartridge 520 and places the cartridge 520 on the mounting portion 512, as in the case of the cartridge 200. Then, as in Embodiment 1, the controller 301 drives the motor 171, the movement mechanism 130, and the detection unit 140. Thereby, as in Embodiment 1, transfer of a complex in the cartridge 520 is reliably performed by the magnet 120. Therefore, as in Embodiment 1, high accuracy of analyzing the test substance by the analyzer 100 can be maintained. Further, in Embodiment 3, since the cartridge 520 can be placed on each of the three mounting portions 512, three cartridges 520 can be simultaneously subjected to analysis.

Embodiment 5

Figure 31A:
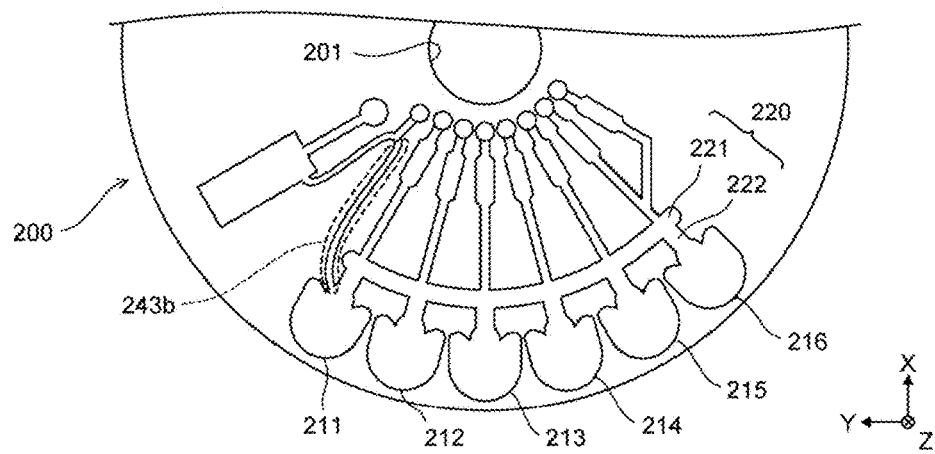
FIG. 31A is a schematic diagram showing a structure of a cartridge according to Embodiment 5 as viewed from above.

In Embodiment 1, as shown in FIG. 2B, the chambers 211 to 216 each have a round shape. In contrast to Embodiment 1, in Embodiment 5, the chambers 211 to 216 each have a shape as shown in FIG. 31A. Other components are the same as the specific examples of components of Embodiment 1.

Figure 31B:
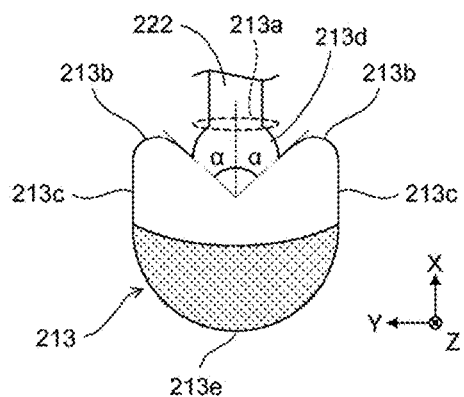
FIGS. 31B and 31C are each an enlarged schematic diagram showing a chamber of the cartridge according to Embodiment 5.
Figure 31C:
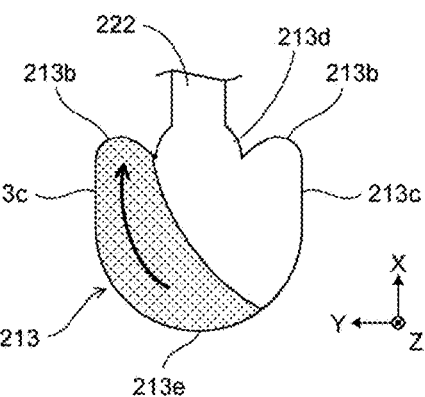

FIGS. 31B and 31C each show an enlarged view of the chamber 213 shown in FIG. 31A. In FIGS. 31A to 31C, the hole 201 of the cartridge 200 is positioned on the X-axis positive side of the chamber 213. That is, the rotation shaft 311 is positioned on the X-axis positive side of the chamber 213. Since the structures of the chambers 211, 212, and 214 to 216 are the same as the structure of the chamber 213, only the structure and effect of the chamber 213 is described below.

As shown in FIG. 31B, the chamber 213 has a symmetrical shape with respect to an extension of the radius of the rotation shaft 311. The chamber 213 is connected to the channel 220 on the rotation shaft 311 side. In addition, the chamber 213 has protruding portions 213b that protrude toward the rotation shaft 311, at opposed sides thereof sandwiching a connection position 213a between the chamber 213 and the channel 220. In other words, the chamber 213 has the protruding portions 213b that protrude in the X-axis direction, at the Y-axis positive side and the Y-axis negative side with respect to the connection position 213a. Each protruding portion 213b is a curved face protruding toward the rotation shaft 311. An angle α is less than 90°, which is formed between an extension of an end portion of the protruding portion 213b on the connection position 213a side, and an extension of the radius of the rotation shaft 311, which passes the center of the connection position 213a.

The chamber 213 has planar wall faces 213c respectively connected to the protruding portions 213b, at opposed sides thereof sandwiching the connection position 213a. Each wall face 213c is connected to an end portion, of the corresponding protruding portion 213b, on the side opposite to the connection position 213a. Specifically, the wall face 213c extends in the radial direction as viewed in the Z-axis direction, that is, extends in the X-axis direction. In addition, the chamber 213 has a protruding portion 213d that protrudes toward the rotation shaft 311, between the two protruding portions 213b. The channel 220 is connected to the protruding portion 213d. In addition, the chamber 213 has an inner wall 213e positioned in a direction away from the rotation shaft 311 in the radial direction. The inner wall 213e has an arc shape as viewed in the Z-axis direction.

The chamber 213 configured as described above provides the following effects.

Even when the cartridge 200 is rotated to agitate the liquid in the chamber 213 by utilizing the centrifugal force and the Euler force as described above, the two protruding portions 213b serve as barriers that inhibit the liquid in the chamber 213 from advancing to the connection position 213a between the chamber 213 and the channel 220. That is, even when the liquid is moved in the chamber 213 by being agitated, an end portion of the liquid in the chamber 213 is trapped in the chamber 213 by the protruding portion 213b as shown in FIG. 31C. Thus, the liquid in the chamber 213 is inhibited from entering the channel 220 during agitation.

When flow of the liquid into the channel 220 is inhibited during agitation as described above, the magnetic particles in the chamber 213 can be moved to the next chamber without being left, whereby appropriate detection can be performed.

Figure 31D:
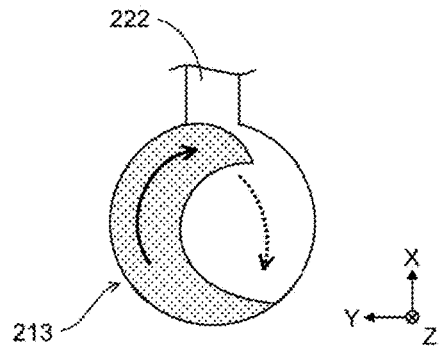
FIGS. 31D and 31E are each an enlarged schematic diagram showing a chamber of a cartridge according to comparative examples.

Even when the liquid in the chamber 213 is greatly shaken during agitation, the liquid in the chamber 213 is received by the protruding portions 213b as shown in FIG. 31C, whereby the liquid is inhibited from further moving along the inner wall of the chamber 213. As shown in FIG. 31D, if the chamber 213 is not provided with the protruding portions 213b, the liquid in the chamber 213 is moved along the inner wall, and a leading end portion of the liquid in the liquid flowing direction is turned in the X-axis negative direction due to a centrifugal force and collides with another portion of the liquid as shown by a dotted arrow. In this case, collision of the liquid causes the liquid to foam. However, if the chamber 213 has the protruding portions 213b, the liquid in the chamber 213 is inhibited from advancing along the inner wall as shown in FIG. 31C, thereby inhibiting foaming of the liquid in the chamber 213 during agitation.

When flow of the liquid into the channel 220 and foaming of the liquid are inhibited during agitation, the rotation speed of the cartridge 200 during agitation can be increased, and the degree of freedom of switching the rotation speed can be increased. On the other hand, when the rotation speed is thus controlled, heat generated from the motor 171 increases. However, since the motor 171 is disposed outside the dark space 340 as described above, even when the heat generated from the motor 171 increases, the temperature inside the dark space 340 is inhibited from being unstable, whereby measurement can be appropriately carried out.

The chamber 213 has the planar wall faces 213c. Therefore, when the liquid comes into contact with the wall faces 213c during agitation, flow of the liquid can be changed, compared with the case where the wall faces are formed in a curved shape, whereby the liquid in the chamber 213 can be effectively agitated. Further, when the wall faces are formed in a curved shape as shown in FIG. 31D, the leading end portion of the liquid in the liquid flowing direction is likely to be turned and collide with another portion of the liquid. However, since the wall faces 213c are formed in a planar shape, the situation as shown in FIG. 31D can be inhibited. Accordingly, the liquid in the chamber 213 can be inhibited from foaming during agitation.

Although the wall faces 213c are formed so as to extend in the radial direction, the wall faces 213c may be formed so as to extend in a direction inclined from the radial direction. However, when the two wall faces 213c are inclined with respect to the radial direction so that the end portions thereof on the X-axis positive side approach each other, collision of the liquid is more likely to occur as in the case shown in FIG. 31D although the liquid in the chamber 213 can be agitated more effectively. When the two wall faces 213c are inclined with respect to the radial direction so that the end portions thereof on the X-axis positive side are away from each other, the effect of agitating the liquid in the chamber 213 is degraded although collision of the liquid is less likely to occur. Therefore, as shown in FIG. 31B, the two wall faces 213c are desirably formed so as to extend in the radial direction.

Figure 31E:
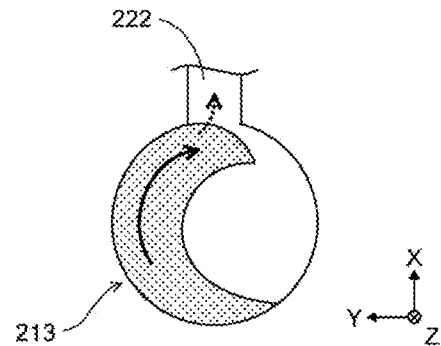

Even when the liquid in the chamber 213 is greatly shaken during agitation and goes over the protruding portion 213b, the liquid is received by the protruding portion 213d, and therefore is less likely to enter the channel 220. As shown in FIG. 31E, if the chamber 213 is not provided with the protruding portion 213d, the greatly shaken liquid enters the channel 220 as shown by a dotted arrow. However, when the chamber 213 is provided with the protruding portion 213d, the liquid in the chamber 213 is reliably inhibited from entering the channel 220 during agitation.

Since each protruding portion 213b is a curved face protruding toward the rotation shaft 311, the magnetic particles are inhibited from remaining in the protruding portion 213b during agitation. Thereby, the magnetic particles in the chamber 213 can be moved to the next chamber without being left. Since the chamber 213 has a symmetrical shape with respect to the radius of the rotation shaft 311, flow of the liquid into the channel 220 and foaming of the liquid can be inhibited in both of the Y-axis positive direction and the Y-axis negative direction. Since the angle α shown in FIG. 31B is smaller than 90°, the end portions of the protruding portions 213b on the connection position 213a side serve as barriers that reliably inhibit flow of the liquid into the channel 220 and foaming of the liquid during agitation.

The shape of the chamber 213 is not limited to the shape shown in FIG. 31B, and may be another shape. For example, the chamber 213 may have any of shapes shown in FIGS. 32A to 32C.

Figure 32A:
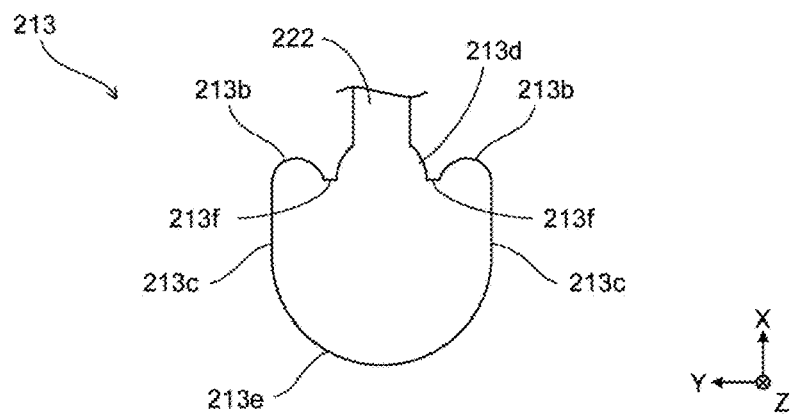
FIGS. 32A to 32C are each a schematic diagram showing a modification of the chamber according to Embodiment 5.

The chamber 213 shown in FIG. 32A has a linear portion 213f between each protruding portion 213b and the protruding portion 213d, compared with FIG. 31B. In this case, the liquid received by each protruding portion 213b is likely to move to the protruding portion 213d along the linear portion 213f due to surface tension. Therefore, it is desirable that the protruding portions 213b and the protruding portion 213d are continuously formed as shown in FIG. 31B.

Figure 32B:
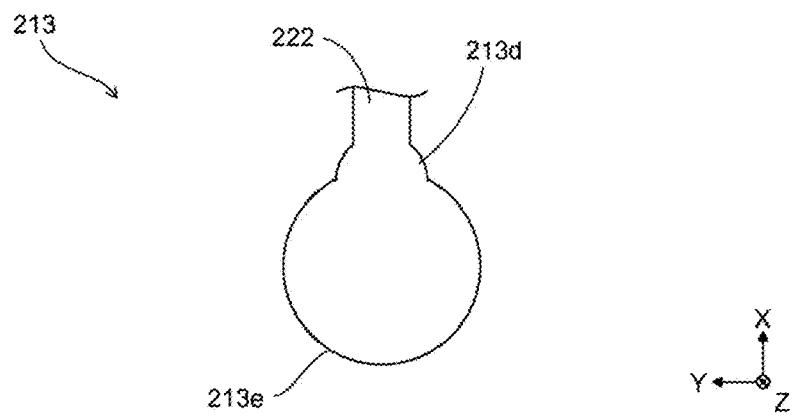

In the chamber 213 shown in FIG. 32B, the protruding portions 213b and the wall faces 213c are omitted compared with FIG. 31B. In this case, when the liquid in the chamber 213 is shaken, the liquid in the chamber 213 is more likely to enter the channel 220 compared with FIG. 31B. However, since the protruding portion 213d is provided, the liquid in the chamber 213 is less likely to enter the channel 220 compared with FIG. 31E.

Figure 32C:
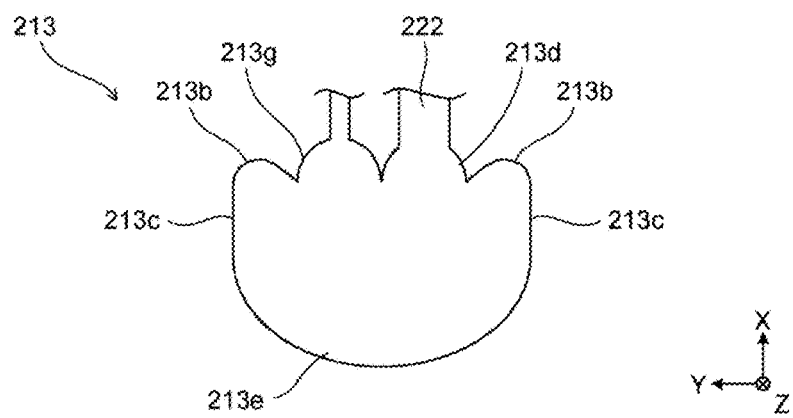

The chamber 213 shown in FIG. 32C is further provided with a protruding portion 213g between the protruding portion 213b on the Y-axis positive side and the protruding portion 213d, compared with FIG. 31B. The protruding portion 213g is connected to, for example, a flow path for passing air therethrough, or a channel other than the channel 220. When the structure shown in FIG. 32C is applied to the chamber 211, the protruding portion 213d is connected to the channel 220, and the protruding portion 213g is connected to the region 243b.

In the chamber 213 shown in FIG. 31B, a flow path for passing air therethrough or a channel other than the channel 220 may be connected to the protruding portion 213d. When another flow path is connected to the protruding portion 213d, molding of the cartridge 200 is facilitated, compared with the case where another flow path is connected to the region 222 of the channel 220.

Figure 33A:
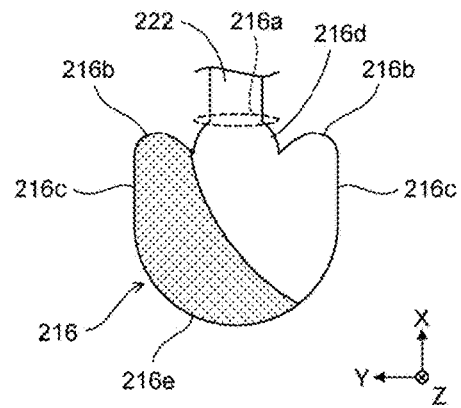
FIGS. 33A and 33B are each a schematic diagram showing a state where a sample storage region is unevenly distributed in the chamber according to Embodiment 5.
Figure 33B:
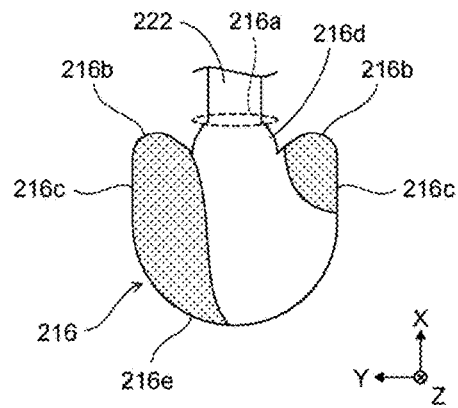

As described above, the structure of the chamber 216 is the same as the structure of the chamber 213. Therefore, as shown in FIGS. 33A and 33B, the chamber 216, like the chamber 213 shown in FIG. 31B, includes protruding portions 216b, wall faces 216c, a protruding portion 216d, and an inner wall 216e. The protruding portions 216b are provided at opposed sides sandwiching a connection position 216a between the chamber 216 and the channel 220.

Since the chamber 216 has such a complicated shape in contrast to the case shown in FIG. 2B, when light generated from the sample S0 in the chamber 216 is detected by the photodetector 144a after agitation, a region where the sample S0 is stored may be unevenly distributed in the chamber 216 as shown in FIGS. 33A and 33B, for example. In the case of FIG. 33A, the sample S0 in the chamber 216 is caught by the protruding portion 216b on the Y-axis positive side and thereby is inclined to the Y-axis positive side in the chamber 216. In the case of FIG. 33B, the sample S0 in the chamber 216 is caught by the two protruding portions 216b and thereby is divided into two parts in the chamber 216.

Figure 33C:
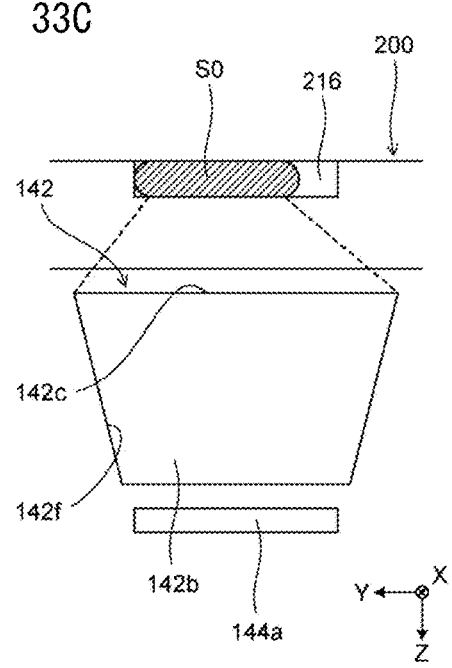
FIGS. 33C and 33D are each a schematic diagram showing a light emitting region of a sample in the chamber according to Embodiment 5 shown in FIGS. 33A and 33B, respectively.
Figure 33D:
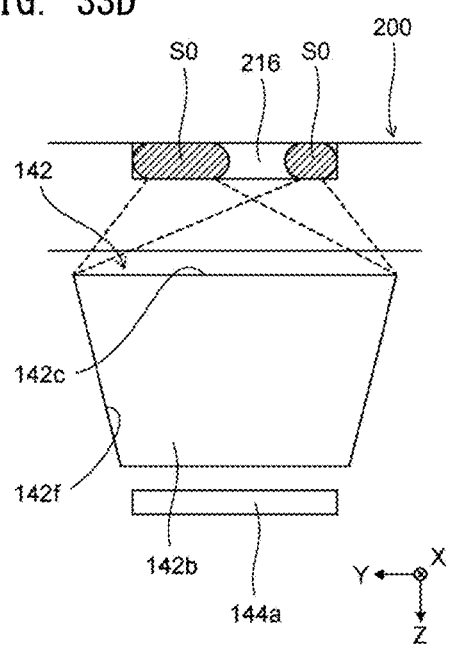

When the position of the sample S0 varies as shown in FIGS. 33A and 33B, the position of the light emitting region of the sample S0 also varies as shown in FIGS. 33C and 33D, respectively. However, as shown in FIGS. 33C and 33D, even when the position of the light emitting region of the sample S0 varies, since the reflection member 142 is disposed between the chamber 216 and the photodetector 144a as described above, variation in the amount of light detected by the photodetector 144a can be inhibited. In addition, the amount of light guided to the photodetector 144a in the case of FIG. 33C can be equalized with the amount of light guided to the photodetector 144a in the case of FIG. 33D. Accordingly, even when the sample S0 has various distribution patterns due to the complicated shape of the chamber 216, variation in the amount of detected light can be inhibited, whereby accuracy of measuring the test substance can be enhanced.

Further, since foaming of the measurement sample in the chamber 216 is also inhibited as in the chamber 213, it is possible to inhibit scattering of light generated from the measurement sample in the chamber 216. Thus, when detection is performed, the amount of light that reaches the photodetector 144a can be increased.

As described above with reference to FIGS. 10A to 10C, when the seal 231a, 232a of the cartridge 200 is pressed by the pressing unit 195, the position of the cartridge 200 is displaced, which may cause displacement of the light emitting region. However, as described above with reference to FIG. 11A, even when the pressing unit 195 presses the seal 231a, 232a, the support member 177 serves as a base to support the cartridge 200. Therefore, displacement of the cartridge 200 is inhibited, whereby the gap between the cartridge 200 and the reflection member 142 can be kept appropriate. Accordingly, variation in the amount of detected light, which is based on displacement of the light emitting region, can be reliably inhibited.

Embodiment 6

Figure 34A:
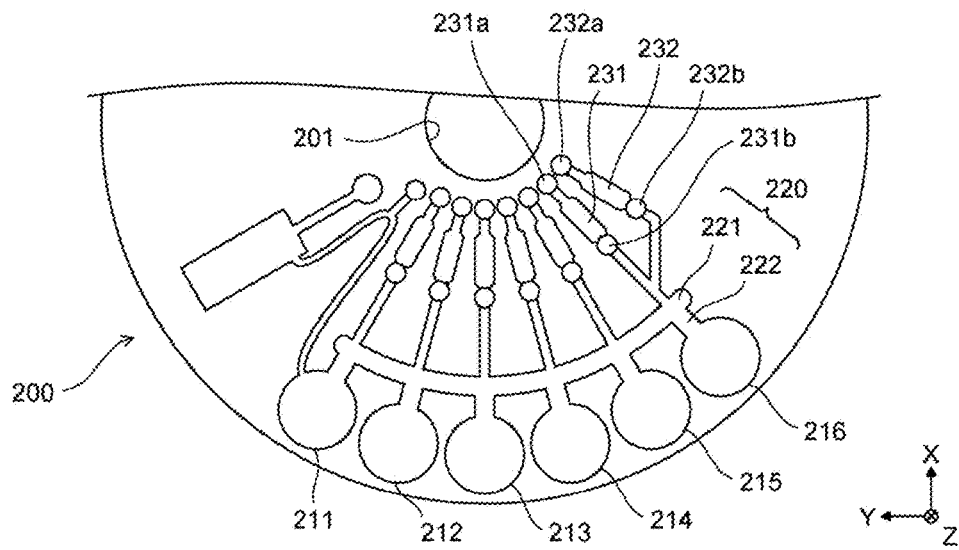
FIG. 34A is a schematic diagram showing a structure of a cartridge according to Embodiment 6 as viewed from above.

In Embodiment 1, a seal is applied to the liquid storage portion 231, 232 at only one position in the radial direction. In contrast, in Embodiment 6, seals are applied to the liquid storage portion 231, 232 at different two positions in the radial direction. Specifically, as shown in FIG. 34A, seals 231a and 231b are respectively applied to inner and outer upper faces, in the radial direction, of the liquid storage portion 231, and seals 232a and 232b are respectively applied to inner and outer upper faces, in the radial direction, of the liquid storage portion 232. In addition, the pressing unit 195 according to Embodiment 6 is configured as shown in FIG. 34B to FIG. 35B. Other components of Embodiment 6 are the same as the specific examples of components of Embodiment 1.

In Embodiment 6, when transferring a reagent stored in the liquid storage portion 231 to a chamber located outward of this liquid storage portion 231, first, the controller 301 drives the motor 171 to rotate the cartridge 200, thereby locating the reagent in the liquid storage portion 231 at the outer peripheral side in the liquid storage portion 231 by a centrifugal force. Subsequently, the controller 301 drives the pressing unit 195 to open the seal 231b positioned outward of the liquid storage portion 231. Thereby, the inside of the liquid storage portion 231 is communicated with the channel 220. Subsequently, the controller 301 drives the pressing unit 195 to open the seal 231a positioned inward of the liquid storage portion 231. Thereby, the inner periphery side of the liquid storage portion 231 is communicated with the outside of the cartridge 200. Then, the controller 301 drives the motor 171 to rotate the cartridge 200, thereby transferring the reagent in the liquid storage portion 231 to the chamber positioned outward of the liquid storage portion 231 by a centrifugal force.

Also when transferring the reagent stored in the liquid storage portion 232 to the chamber 216, the controller 301 performs the same process as described above. That is, the controller 301 performs, in order, rotation of the cartridge 200, opening of the seal 232b, opening of the seal 232a, and rotation of the cartridge 200.

In Embodiment 6, the reagent in the liquid storage portion 231 is hermetically sealed in the liquid storage portion 231 by the seals 231a and 231b, and the reagent in the liquid storage portion 232 is hermetically sealed in the liquid storage portion 232 by the seals 232a and 232b. Thereby, the reagent in the liquid storage portion 231, 232 is inhibited from flowing into the channel 220 and the chambers 211 to 216 before use of the cartridge 200. In addition, when transferring the reagent in the liquid storage portion 231, 232 to the chamber, since the inner side and the outer side of the liquid storage portion 231, 232 are opened, the reagent in the liquid storage portion 231, 232 can be transferred to the corresponding chamber more smoothly compared with Embodiment 1.

Before the seal is opened, the reagent in the liquid storage portion 231, 232 is positioned to the outer peripheral side in advance. Therefore, after the seal is opened, the reagent in the liquid storage portion 231, 232 can be smoothly transferred to the chamber positioned outward of the liquid storage portion 231, 232. In addition, after the seal 231b, 232b on the outer side is opened, the seal 231a, 232a on the inner side is opened. Therefore, the reagent in the liquid storage portion 231, 232 can be smoothly transferred to the chamber positioned outward of the liquid storage portion 231, 232 without returning back to the inner side.

Next, the pressing unit 195 of Embodiment 6 is described.

The pressing unit 195 of Embodiment 6 includes: a moving member 365; and a plurality of cam parts that are mounted to the moving member 365, and cause pin members 366 for opening each of the respective seals to move in the pressing direction. The cam parts are disposed at different positions in the moving direction of the moving member 365 so as to drive the respective pin members 366 in a predetermined order. Specifically, the pressing unit 195 is configured as shown in FIG. 34B to FIG. 35B.

Figure 34B:
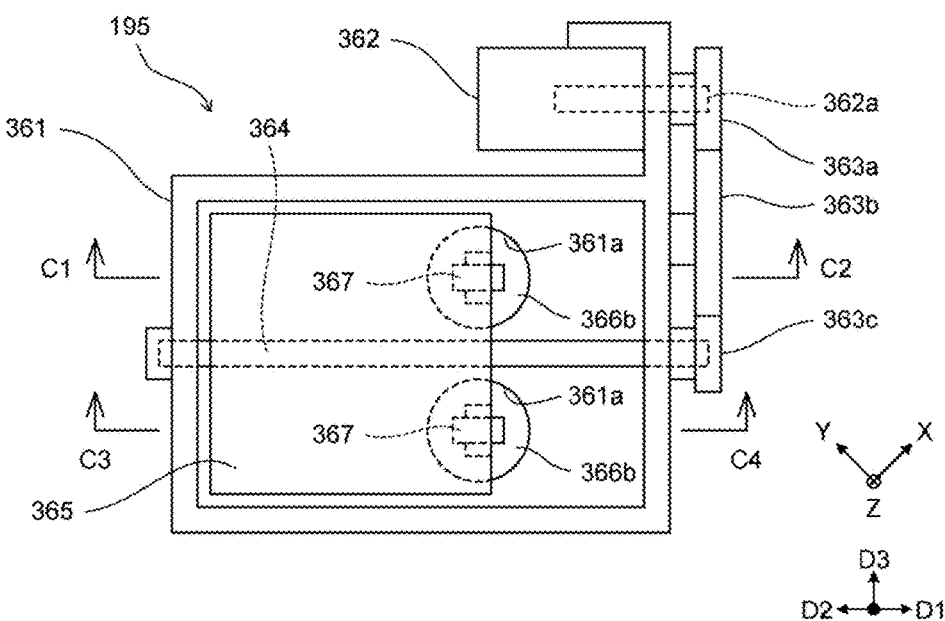
FIG. 34B is a schematic diagram showing a structure of a pressing unit according to Embodiment 6 as viewed from above.
Figure 35A:
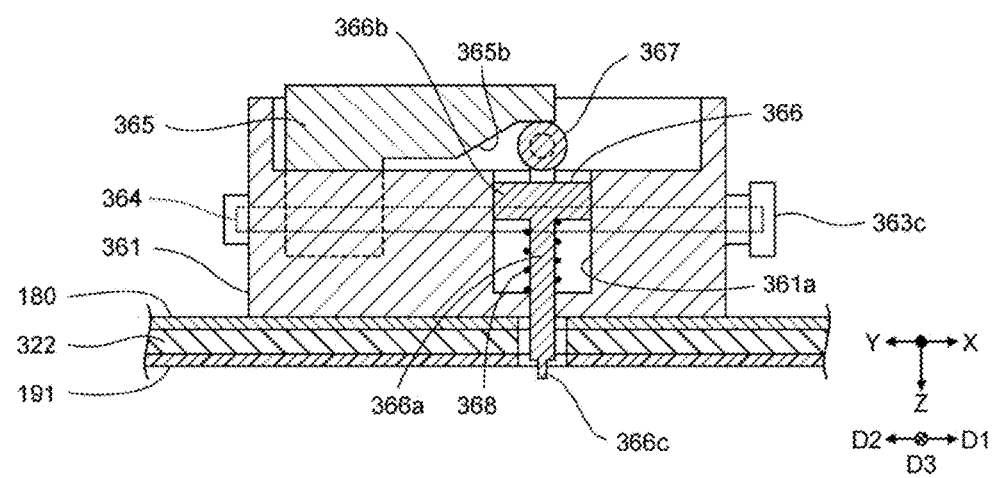
FIGS. 35A and 35B are each a schematic diagram showing a cross-section of the pressing unit according to Embodiment 6 as viewed from the side thereof.
Figure 35B:
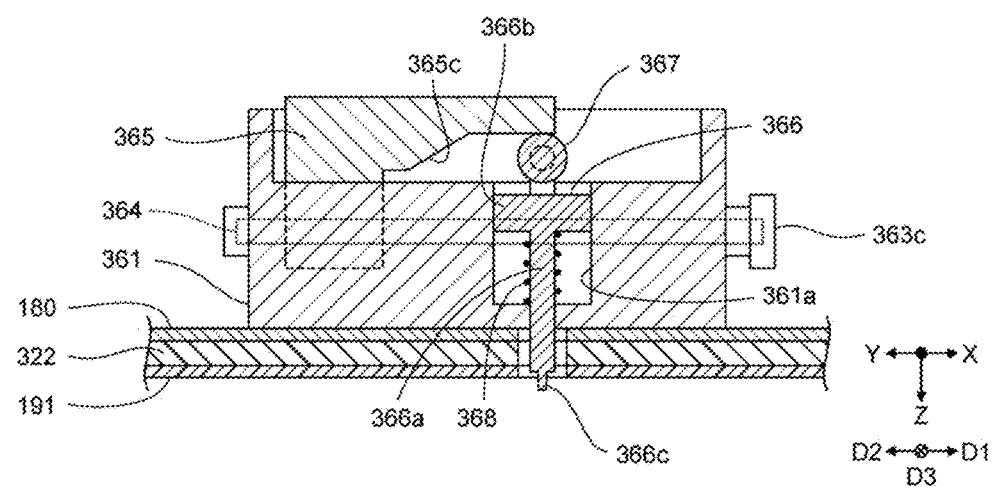
Figure 36:
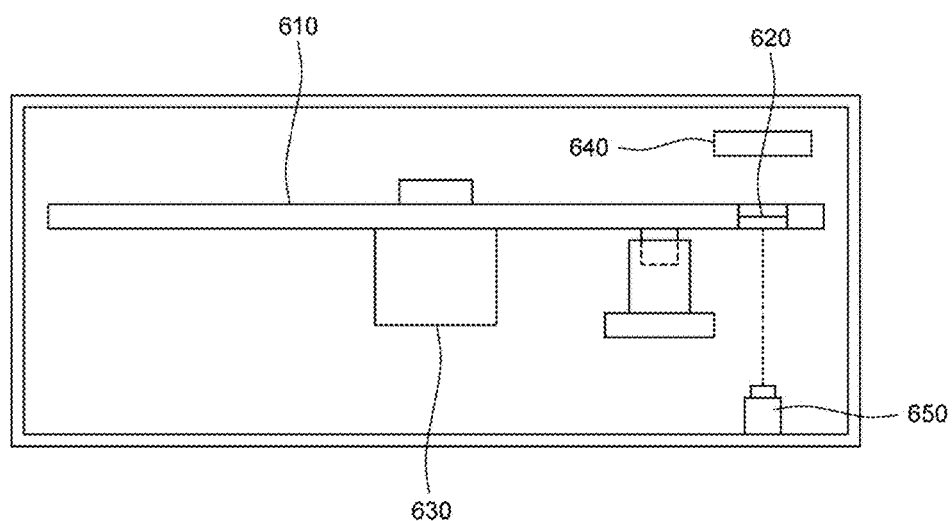
FIG. 36 is a schematic diagram showing a structure according to a related technology.

As shown in FIG. 34B, in Embodiment 6, compared with Embodiment 1, two pin members 366 are disposed in the radial direction. Specifically, two holes 361a are provided in the mount member 361, and the pin members 366 and rollers 367 are disposed at the positions of the two holes 361a. FIG. 35A is a view showing a cross-section C1-C2 in FIG. 34B as viewed in the D3 direction. FIG. 35B is a view showing a cross-section C3-C4 in FIG. 34B as viewed in the D3 direction. As shown in FIGS. 35A and 35B, the pin members 366 are disposed at the positions of the two holes 361a.

As shown in FIGS. 35A and 35B, cam parts 365b and 365c, which are planes inclined with respect to a horizontal plane, are formed on the lower face side of the moving member 365. The cam part 365b is formed at a position corresponding to the roller 367 on the D3 direction side. The cam part 365c is formed at a position corresponding to the roller 367 on the opposite side from the D3 direction side. The positions of the cam parts 365b and 365c are different from each other in the D1-D2 direction. Specifically, the cam part 365b is positioned on the D1 direction side relative to the cam part 365c.

When opening the seals 231a and 231b of the liquid storage portion 231, the controller 301 causes the cartridge 200 to rotate so as to distribute the reagent in the liquid storage portion 231 outward, and thereafter, causes the seals 231a and 231b to be located at a position directly beneath the pin member 366 on the opposite side from the D3 direction and a position directly beneath the pin member 366 on the D3 direction side, respectively.

Then, the controller 301 drives the motor 362 to move the moving member 365 in the D1 direction. At this time, when the moving member 365 is moved in the D1 direction from the state shown in FIGS. 35A and 35B, the cam part 365b comes into contact with the roller 367 before the cam part 365c, and thereafter the cam part 365c comes into contact with the roller 367. Therefore, the pin member 366 on the D3 direction side is moved downward before the pin member 366 on the opposite direction side from the D3 direction. Thus, as described above, the seal 231b on the outer side is first opened and thereafter the seal 231a on the inner side is opened.

When the different cam parts 365b and 365c are provided at the lower face of the moving member 365 and the pin members 366 are provided so as to correspond to the cam parts 365b and 365c as described above, the seals 231b and 231a can be opened in order only by moving the moving member 365 in the D1 direction. The seals 232a and 232b of the liquid storage portion 232 can be opened in a similar manner. Also in this case, the seals 232b and 232a can be opened in order only by moving the moving member 365 in the D1 direction.

In addition to the above, various modifications of the embodiments of the present invention may be made as appropriate without departing from the scope of the technical idea defined by the claims.

What is claimed is:

1. A measurement apparatus comprising:
   a support mechanism configured to support a cartridge in which a chamber is formed, the chamber being configured to receive a measurement sample that generates light, an intensity of which varies depending on an amount of a test substance;
   a photodetector configured to detect the light generated from the measurement sample in the chamber; and
   a reflection member provided between the photodetector and the cartridge supported by the support mechanism, the reflection member having a cylindrical shape with a first opening at one side close to the chamber and a second opening at another side close to the photodetector, the first and second openings being connected by an inner face configured to reflect the light from the measurement sample, thereby guiding the light to the photodetector, wherein
   an area defined by the inner face is decreased from the one side to the another side of the reflection member.

2. The measurement apparatus of claim 1, wherein the cylindrical shape is a circular cone shape, wherein a radius of the first opening is greater than a radius of the second opening.

3. The measurement apparatus of claim 2, wherein
   the support mechanism comprises a support member that supports the cartridge, and a motor that rotates the support member around a rotation shaft, and
   the support mechanism rotates the cartridge supported by the support member to locate the chamber at a detection position of the photodetector.

4. The measurement apparatus of claim 3, wherein
   the cartridge has a liquid storage portion having a seal,
   the measurement apparatus comprises a pressing unit configured to press the seal, and
   the support member is provided at a position opposed to the pressing unit with the cartridge interposed between the support member and the pressing unit.

5. The measurement apparatus of claim 4, wherein the support member is provided from a side where the rotation shaft is provided to the position opposed to the pressing unit.

6. The measurement apparatus of claim 2, wherein the first opening is located at a position spaced apart from a plane including a support face of the support mechanism that supports the cartridge.

7. The measurement apparatus of claim 6, wherein a distance between the first opening and a bottom face of the chamber of the cartridge supported by the support mechanism is not less than 1 mm and not greater than 20 mm.

8. The measurement apparatus of claim 2, wherein the first opening has a size including the chamber located at a detection position of the photodetector, as viewed from the side where the photodetector is provided.

9. The measurement apparatus of claim 2, wherein the inner face is linear at a cross-section along an axis connecting a center of the first opening and a center of the second opening.

10. The measurement apparatus of claim 9, wherein the inner face has an inclination angle not smaller than 5° and not larger than 20° with respect to the axis.

11. The measurement apparatus of claim 2, wherein the inner face has, at a cross-section along an axis connecting a center of the first opening and a center of the second opening, curved portions that protrude to opposite sides from the axis.

12. The measurement apparatus of claim 2, wherein the inner face has, at a cross-section along an axis connecting a center of the first opening and a center of the second opening, curved portions that protrude toward the axis.

13. The measurement apparatus of claim 2, wherein the first opening and the second opening each have a round shape.

14. The measurement apparatus of claim 13, wherein
the first opening has a diameter not smaller than 10.9 mm and not larger than 16.6 mm, and
the second opening has a diameter not smaller than 67% and not larger than 88% of the diameter of the first opening.

15. The measurement apparatus of claim 2, wherein the first opening, the second opening, and the inner face of the reflection member are set such that an amount of light received by a detection face of the photodetector when the measurement sample in the chamber is located at a position displaced toward an edge of the first opening is 90% to 110% of an amount of light received by the detection face when the measurement sample in the chamber is located at a center of the first opening.

16. The measurement apparatus of claim 2, wherein
a plurality of the chambers and a channel that connects the plurality of the chambers are formed in the cartridge, and
the test substance is successively transferred to the plurality of the chambers via the channel, thereby to prepare the measurement sample.

17. The measurement apparatus of claim 16, wherein
the support mechanism comprises a support member that supports the cartridge, and a motor that rotates the support member around a rotation shaft,
each of the chambers is connected to the channel at a side where the rotation shaft is provided, and
each of the chambers has protruding portions that protrude toward the rotation shaft, at opposed sides thereof sandwiching a connection position between the chamber and the channel.

18. The measurement apparatus of claim 17, wherein each of the chambers has planar wall faces connected to the protruding portions, at the opposed sides thereof sandwiching the connection position.

19. A measurement method for measuring a test substance by using a cartridge in which a chamber is formed, the chamber being configured to store a measurement sample that generates light an intensity of which varies depending on an amount of a test substance, the method comprising:
causing the light generated from the measurement sample stored in the chamber to be reflected at an inner face of a reflection member and guided to a photodetector so that a part of the light taken into the reflection member is reflected to a direction in which the light is not received by the photodetector, thereby to reduce an amount of the light received by the photodetector, wherein
in a case where the measurement sample is positioned near a center of a region surrounded by the inner face of the reflection member, a larger amount of light, with respect to the light taken into the reflection member, is reflected to the direction in which the light is not received by the photodetector, than in a case where the measurement sample is positioned near an edge of the region surrounded by the inner face of the reflection member.

20. A measurement apparatus comprising:
a support mechanism configured to support a cartridge in which a chamber is formed, the chamber being configured to receive a measurement sample that generates light, an intensity of which varies depending on an amount of a test substance;
a photodetector configured to detect the light generated from the measurement sample in the chamber; and
a reflection member provided between the photodetector and the cartridge supported by the support mechanism, the reflection member having a circular cone shape with a first opening at one side close to the chamber and a second opening at another side close to the photodetector, wherein a radius of the first opening is greater than a radius of the second opening and the first and second openings being connected by an inner face configured to reflect the light from the measurement sample, thereby guiding the light to the photodetector, wherein
an area defined by the inner face is decreased from the one side to the another side of the reflection member.

* * * * *